US006849413B2

(12) United States Patent
Young et al.

(10) Patent No.: US 6,849,413 B2
(45) Date of Patent: Feb. 1, 2005

(54) PGRP-L POLYNUCLEOTIDES, POLYPEPTIDES, AND ANTIBODIES

(75) Inventors: Paul E. Young, Gaithersburg, MD (US); Steven M. Ruben, Brookeville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 339 days.

(21) Appl. No.: 10/068,956

(22) Filed: Feb. 11, 2002

(65) Prior Publication Data

US 2003/0204065 A1 Oct. 30, 2003

Related U.S. Application Data

(63) Continuation-in-part of application No. PCT/US00/22877, filed on Aug. 18, 2000.
(60) Provisional application No. 60/149,715, filed on Aug. 20, 1999.

(51) Int. Cl.$^7$ ............................................... G01N 33/53
(52) U.S. Cl. .................. 435/7.1; 424/133.1; 424/139.1; 424/141.1; 424/142.1; 424/152.1; 424/130.1; 530/387.1; 530/387.3; 530/387.9; 530/388.1; 530/388.15; 530/388.7; 435/326
(58) Field of Search .................. 424/130.1, 133.1, 424/139.1, 141.1, 142.1, 152.1; 530/387.1, 387.3, 387.9, 388.1, 388.15, 388.7; 435/7.1, 326

(56) References Cited

FOREIGN PATENT DOCUMENTS

WO    WO-00/05367 A2    2/2000

OTHER PUBLICATIONS

Kibardin. Submitted. May 1999. Genbank Accession No. Q9QXZ2.*

Wang et al., "Human Peptidoglycan Recognition Protein–L is an N–Acetylmuramoyl–L–alanine Amidase," *J. Biol. Chem.* 278(49):49044–49052 (Dec. 5, 2003).

Liu et al., "Peptidoglycan Recognition Proteins," *J. Biol. Chem.* 276(37):34686–34694 (Sep. 14, 2001).

Hillier et al., GenBank Accession No. AA121766, "zn95a11.r1 Stratagene fetal retina 937202 *Homo sapiens* cDNA clone IMAGE:565916 5' similar to contains L1.b1 L1 repetitive element;, mRNA sequence". (Feb. 2, 1997).

NCI–CGAP, GenBank Accession No. AA829438, "od27d10.s1 NCI_CGAP_GCB1 *Homo sapiens* cDNA clone IMAGE;1369171 3' similar to contains L1.t3 L1 repetitive element;, mRNA sequence". (Mar. 31, 1998).

De Pauw et al., "Characterization of human serum N–acetyl-muramyl–L–alanine amidase purified by affinity chromatography," *Protein Expr. Purif.* 6(3):371–378 (Jun. 1995).

Ochiai et al., "A Pattern Recognition Protein for Peptidoglycan," *J. Biol. Chem.* 274(17):11854–11858 (Apr. 23, 1999).

Kang et al., A peptidoglycan recognition protein in innate immunity conserved from insects to humans, *Proc. Natl. Acad. Sci. USA* 95:10078–10082 (Aug. 1998).

Rehman et al., "Cloning and expression of peptidoglycan recognition protein (PGRP) in the brain and spleen of rattus norvegicus," *Society for Neuroscience Abstracts*, 25(1–2):1445 (1999), abstract No. 580.4.

International Search Report for International Application No. PCT/US00/22877 dated Feb. 7, 2001.

* cited by examiner

*Primary Examiner*—Jennifer E. Graser
(74) *Attorney, Agent, or Firm*—Human Genome Sciences, Inc.

(57) ABSTRACT

The present invention relates to novel human and murine proteins called PGRP-L, and isolated polynucleotides encoding these proteins. Also provided are vectors, host cells, antibodies, and recombinant methods for producing this human protein. The invention further relates to diagnostic and therapeutic methods useful for diagnosing and treating disorders related to this novel human protein.

15 Claims, 9 Drawing Sheets

```
  1  GACGCGGCTGGCACTGGGTGGGCGCCCACACGCTCGGCCACAACTCCCGGGGCTTCGGCG   60
  1   R  G  W  H  W  V  G  A  H  T  L  G  H  N  S  R  G  F  G  V   20

61  TGGCCATAGTGGGCAACTACACCGCGGCGCTGCCCACCGAGGCCGCTCTGCGCACGGTGC  120
 21   A  I  V  G  N  Y  T  A  A  L  P  T  E  A  A  L  R  T  V  R   40

121  GCGACACGCTCCCGAGTTGTGCGGTGCGCGCCGGCCTCCTGCGGCCAGACTACGCGCTGC  180
 41   D  T  L  P  S  C  A  V  R  A  G  L  L  R  P  D  Y  A  L  L   60

181  TGGGCCACCGCCAGCTGGTGCGCACCGACTGCCCCGGCGACGCGCTCTTCGACCTGCTGC  240
 61   G  H  R  Q  L  V  R  T  D  C  P  G  D  A  L  F  D  L  L  R   80

241  GCACCTGGCCGCACTTCACCGCGGTGAGTCTTCGCAGCCTGCACTACACGGCCCGCCGCC  300
 81   T  W  P  H  F  T  A  V  S  L  R  S  L  H  Y  T  A  R  R  P  100

301  CCTCCGTCTACACAAGCTCCACGAGGCCCCTGCCCCCTGCCTGTAACAGCTGTGCCCGCA  360
101   S  V  Y  T  S  S  T  R  P  L  P  P  A  C  N  S  C  A  R  T  120

361  CAGCCTCAGCCAGGCCCCCAACTTCCCGGCGGCACGTCTATTCAGGAAACCTAGGCCCAG  420
121   A  S  A  R  P  P  T  S  R  R  H  V  Y  S  G  N  L  G  P  A  140

421  CCTTTGCGGGTCACTCTGCGGGCAACATCCCTGATCCTGTGACTTCTGCCTATGCAGCCT  480
141   F  A  G  H  S  A  G  N  I  P  D  P  V  T  S  A  Y  A  A  S  160

481  CAGCTCAGCCCCAGACCCAGCCAGCCTGTCCTTTCCCCAGCTCCTAATACCTCTACCTTT  540
161   A  Q  P  Q  T  Q  P  A  C  P  F  P  S  S                    174

541  CCAGCCAAGGCATGGACCCTGACACCTGCCAACAGCCCCTCTGCCCTCACAACCTCAGCC  600

601  TGGCCTTCATGACTTCTCTACCCAAGTCACAACCTGTCAGGCTGCACCACCTCATCCTGG  660

661  CCCGCCGAACCTTGACCTCACCCCTGCCCCTACCCGAAGGCTCTCTGTCCACACAACATG  720
```

FIG. 1A

```
721  AACCTAGGCTGTGACCTTTTGCCTTCACAACCTCTGTCCAGTCCTTAATCCTGTGTTGCA  780

781  ATTCTCTGTCCAGACAATCTCAACTCTGAGGTTGCTTGTTTCGTCCCTGACTCCTTAACC  840

841  CCTGATGACAACTCTTATGCCAGCACAACTTTGACCTGATGACCTCATCCCAGCCCTTGA  900

901  TCGCCATCACTAAAACAATTTTAGAATCACACCTGGACAATCTCGTGCTACCTACATACT  960

961  GCCACTCCATTTCATTAAGCTATTGACTAGCACATCCATCTCGGCCTATAGTTGGCTTTG  1020

1021 TCCTCACTCTCTCACTTTGGGCCACTGTCCCCTCCCTGATAAAGGGGATATCACCACCGA  1080

1081 TCCCACAGAAATACAAACTACCATCAGAGAATACTATAAACACCTCTATGCAAATAAACT  1140

1041 AGAAAATCTAGAAGAAATGGATAAATTCCTCAACACCCACTACCAAAAAAAAAAAAAAA   1200
```

FIG. 1B

```
  1 GCCGTTATGTGAGGTAAGCAGCTTTCTCCAACAGAAGTTCCTCTCTCCTCAAAGGCCCAG   60

61 AGTGTCCAGGCCAACCAACTGACCAAGAATTACAACTGCTGAAACTGGCCTCCGAGGTTC  120

121 TCTGCTGGGTCTGTGCCCTGGAACTGGAGACCCACCATGAAGGCCTGGGGTGCCCTCTGG  180
  1                                   M  K  A  W  G  A  L  W      8

181 ATCGTGCTTGGATTGCTGCTGTGGCCAGAGCCAGGGGCAGCCTCCTCCTTGCCTCTGCTC  240
  9  I  V  L  G  L  L  L  W  P  E  P  G  A  A  S  S  L  P  L  L   28

241 ATGGACTCCATCATCCAGGCCCTTGCTGAACTTGAGCAAAAGGTACCAGTGACTGAGGCC  300
 29  M  D  S  I  I  Q  A  L  A  E  L  E  Q  K  V  P  V  T  E  A   48

301 AGCATCACTGCCTCTGCATGGATTCTGTCAGCCAAGAACTCCAGCACCCACAATTCCCTT  360
 49  S  I  T  A  S  A  W  I  L  S  A  K  N  S  S  T  H  N  S  L   68

361 CACCAGCGCTTGCTGCTGAAGGCACCAAGCCACAACACTACAGAGCCAGATCCTCACTCT  420
 69  H  Q  R  L  L  L  K  A  P  S  H  N  T  T  E  P  D  P  H  S   88

421 CTCAGCCCGGAGCTTCAAGCACTGATTTCTGAGGTGGCTCAACACGATGTACAGAATGGG  480
 89  L  S  P  E  L  Q  A  L  I  S  E  V  A  Q  H  D  V  Q  N  G  108

481 CGGGAATATGGAGTGGTGCTGGCACCTGATGGCTCCACCGTAGCTGTGAAGCCTCTGCTG  540
109  R  E  Y  G  V  V  L  A  P  D  G  S  T  V  A  V  K  P  L  L  128

541 TTTGGGCTAGAGGCCGGTCTACAGGCACACAGCGTTGCTAACTTGCCTTCAGATTGTCTG  600
129  F  G  L  E  A  G  L  Q  A  H  S  V  A  N  L  P  S  D  C  L  148

601 GCTATCCCCTGTGATACTGGAGACACCTTGGCCAATATTAGAGCCACCTGGCCAGGACTC  660
149  A  I  P  C  D  T  G  D  T  L  A  N  I  R  A  T  W  P  G  L  168

661 ATGGATGCTTTTCCAAATGCCTCTTCTCCAGATGTTGGAGCCACTTTACCAAACGACAAA  720
169  M  D  A  F  P  N  A  S  S  P  D  V  G  A  T  L  P  N  D  K  188
```

FIG. 2A

```
721  GCCAAGACTCCCACCACTGTGGACAGACTCCTGGCAATCACCTTGGCTGGTGACTTAGGT  780
189   A  K  T  P  T  T  V  D  R  L  L  A  I  T  L  A  G  D  L  G   208

781  CTGACCTTCCTCCACAGGTCCCAGACTTGGAGTCCTCCAGGACTGGGAACTGAGGGCTGC  840
209   L  T  F  L  H  R  S  Q  T  W  S  P  P  G  L  G  T  E  G  C   228

841  TGGGACCAGCTTACTGCCCCCAGGGTCTTCACACTGTTGGACCCCCAGGCATCCAGGCTC  900
229   W  D  Q  L  T  A  P  R  V  F  T  L  L  D  P  Q  A  S  R  L   248

901  ACCATGGCTTTCCTCAATGGTGCCTTAGATGGAGCTCTCCTTGGGAACCACTTGAGCCAA  960
249   T  M  A  F  L  N  G  A  L  D  G  A  L  L  G  N  H  L  S  Q   268

961  ATCCCTAGGCCCCACCCACCCCTCAGCCACCTGCTAAGAGAGTACTATGGAGCTGGGGTG  1020
269   I  P  R  P  H  P  P  L  S  H  L  L  R  E  Y  Y  G  A  G  V   288

1021 AATGGAGATCCGGTGTTCCGAAGTAACTTCCGAAGGCAGAACGGTGCTGCTTTGACTTCA  1080
289   N  G  D  P  V  F  R  S  N  F  R  R  Q  N  G  A  A  L  T  S   308

1081 GCCCCTACCCTGGCCCAGCAGGTATGGGAGGCCCTTGTCCTGTTACAGAAACTGGAGCCA  1140
309   A  P  T  L  A  Q  Q  V  W  E  A  L  V  L  L  Q  K  L  E  P   328

1141 GAACACCTACAGTTGCAGAACATTAGCCAAGAGCAGCTGGCTCAGGTAGCCACCTTGGCT  1200
329   E  H  L  Q  L  Q  N  I  S  Q  E  Q  L  A  Q  V  A  T  L  A   348

1201 ACCAAGGAGTTCACTGAGGCTTTCCTGGGATGCCCAGCCATTCACCCCCGCTGCCGTTGG  1260
349   T  K  E  F  T  E  A  F  L  G  C  P  A  I  H  P  R  C  R  W   368

1261 GGAGCGGCTCCCTACCGAGGCCACCCAACACCACTCCGGCTGCCACTTGGATTCTTATAT  1320
369   G  A  A  P  Y  R  G  H  P  T  P  L  R  L  P  L  G  F  L  Y   388

1321 GTGCATCACACATACGTGCCAGCGCCACCCTGCACCACCTTCCAGAGCTGCGCCGCCGAT  1380
389   V  H  H  T  Y  V  P  A  P  P  C  T  T  F  Q  S  C  A  A  D   408
```

FIG. 2B

```
1381 ATGCGCTCCATGCAGCGTTTCCACCAGGATGTGCGCAAGTGGGATGACATCGGCTACAGT 1440
 409  M  R  S  M  Q  R  F  H  Q  D  V  R  K  W  D  D  I  G  Y  S  428

1441 TTCGTGGTAGGCTCCGACGGCTATCTGTACCAGGGCCGTGGCTGGCACTGGGTAGGTGCG 1500
 429  F  V  V  G  S  D  G  Y  L  Y  Q  G  R  G  W  H  W  V  G  A  448

1501 CACACACGCGGCTACAACTCCCGCGGCTTCGGTGTGGCCTTCGTGGGCAACTACACTGGG 1560
 449  H  T  R  G  Y  N  S  R  G  F  G  V  A  F  V  G  N  Y  T  G  468

1561 TCACTGCCCAACGAAGCTGCGCTGAACACGGTGCGCGACGCGCTCCCGAGCTGCGCAATT 1620
 469  S  L  P  N  E  A  A  L  N  T  V  R  D  A  L  P  S  C  A  I  488

1621 CGCGAAGGTCTCTTGCGGCCAGACTACAAGCTGCTTGGCCACCGCCAGCTAGTGCTCACC 1680
 489  R  E  G  L  L  R  P  D  Y  K  L  L  G  H  R  Q  L  V  L  T  508

1681 CACTGCCCCGGGAACGCGCTCTTCAACTTGCTGCGCACCTGGCCTCACTTCACAGAGGTT 1740
 509  H  C  P  G  N  A  L  F  N  L  L  R  T  W  P  H  F  T  E  V  528

1741 GAAAACTAAGAACTCCTTTGAGAGACCCTTGAAGATCCAGGAGGTATTATCCCTGATGAT 1800
 529  E  N  *                                                      531

1801 CCTTTGAGCAACCACAGACCTCCAATAAAGGGACCACTGAAAGGAAAAAAAAAAAAAAAA 1860

1861 AAAAAAAAAAAAAAAA 1876
```

FIG. 2C

```
                    10          20          30          40
                    |           |           |           |
  1  ----------------------------------------------------  hPGRP-L aa Seq.
  1  M K A W G A L W I V L G L L L W P E P G A A S S L P L L M D S I I Q A L A E L E  mPGRP-L aa Seq.

50          60          70          80
                    |           |           |           |
  1  ----------------------------------------------------  hPGRP-L aa Seq.
 41  Q K V P V T E A S I T A S A W I L S A K N S S T H N S L H Q R L L L K A P S H N  mPGRP-L aa Seq.

90         100         110         120
                    |           |           |           |
  1  ----------------------------------------------------  hPGRP-L aa Seq.
 81  T T E P D P H S L S P E L Q A L I S E V A Q H D V Q N G R E Y G V V L A P D G S  mPGRP-L aa Seq.

130         140         150         160
                    |           |           |           |
  1  ----------------------------------------------------  hPGRP-L aa Seq.
121  T V A V K P L L F G L E A G L Q A H S V A N L P S D C L A I P C D T G D T L A N  mPGRP-L aa Seq.

170         180         190         200
                    |           |           |           |
  1  ----------------------------------------------------  hPGRP-L aa Seq.
161  I R A T W P G L M D A F P N A S S P D V G A T L P N D K A K T P T T V D R L L A  mPGRP-L aa Seq.

210         220         230         240
                    |           |           |           |
  1  ----------------------------------------------------  hPGRP-L aa Seq.
201  I T L A G D L G L T F L H R S Q T W S P P G L G T E G C W D Q L T A P R V F T L  mPGRP-L aa Seq.

250         260         270         280
                    |           |           |           |
  1  ----------------------------------------------------  hPGRP-L aa Seq.
241  L D P Q A S R L T M A F L N G A L D G A L L G N H L S Q I P R P H P P L S H L L  mPGRP-L aa Seq.

290         300         310         320
                    |           |           |           |
  1  ----------------------------------------------------  hPGRP-L aa Seq.
281  R E Y Y G A G V N G D P V F R S N F R R Q N G A A L T S A P T L A Q Q V W E A L  mPGRP-L aa Seq.
```

FIG. 3A

```
                                330         340         350         360
                                 |           |           |           |
  1  - - - - - - - - - - - - - - - - - - - - - - - - - - - - - - - - -  hPGRP-L aa Seq.
321  V L L Q K L E P E H L Q L Q N I S Q E Q L A Q V A T L A T K E F T E A F L G C P  mPGRP-L aa Seq.

370         380         390         400
                                 |           |           |           |
  1  - - - - - - - - - - - - - - - - - - - - - - - - - - - - - - - - -  hPGRP-L aa Seq.
361  A I H P R C R W G A A P Y R G H P T P L R L P L G F L Y V H H T Y V P A P P C T  mPGRP-L aa Seq.

410         420         430         440
                                 |           |           |           |
  1  - - - - - - - - - - - - - - - - - - - - - - - - - - - - - - - - -  hPGRP-L aa Seq.
401  T F Q S C A A D M R S M Q R F H Q D V R K W D D I G Y S F V V G S D G Y L Y Q G  mPGRP-L aa Seq.

450         460         470         480
                                 |           |           |           |
  1  R G W H W V G A H T L G H N S R G F G V A I V G N Y T A A L P T E A A L R T V R  hPGRP-L aa Seq.
441  R G W H W V G A H T R G Y N S R G F G V A F V G N Y T G S L P N E A A L N T V R  mPGRP-L aa Seq.

490         500         510         520
                                 |           |           |           |
 41  D T L P S C A V R A G L L R P D Y A L L G H R Q L V R T D C P G D A L F D L L R  hPGRP-L aa Seq.
481  D A L P S C I R E G L L R P D Y K L L G H R Q L V L T H C P G N A L F N L L R  mPGRP-L aa Seq.

530         540         550         560
                                 |           |           |           |
 81  T W P H F T A V S L R S L H Y T A R R P S V Y T S S T R P L P P A C N S C A R T  hPGRP-L aa Seq.
521  T W P H F T E V E - - - - - - - - - - - - - - - - - - - - - - - - - - - - - -  mPGRP-L aa Seq.

570         580         590         600
                                 |           |           |           |
121  A S A R P P T S R R E V Y S G N L G P A F A G H S A G N I P D P V T S A Y A A S  hPGRP-L aa Seq.
530  - - - - - - - - - - - - - - - - - - - - - - - - - - - - - - - - - - - - - - -  mPGRP-L aa Seq.

610
                                 |
161  A Q P Q T Q P A C P F P S S                                          hPGRP-L aa Seq.
530  - - - - - - - - - - - N                    FIG. 3B                  mPGRP-L aa Seq.
```

PGRP-L POLYNUCLEOTIDES, POLYPEPTIDES, AND ANTIBODIES

CROSS-REFERENCE TO RELATED APPLICATIONS

This Application is a Continuation-In-Part of, and claims benefit under 35 U.S.C. § 120 of copending PCT International Application Serial No. PCT/US00/22877 filed Aug. 18, 2000, which International Application is hereby incorporated by reference in its entirety, which claims benefit under 35 U.S.C. § 119(e) based on Provisional Application Ser. No. 60/149,715 filed Aug. 20, 1999, which Provisional Application is hereby incorporated by reference in its entirety.

FIELD OF THE INVENTION

The present invention relates to a novel peptidoglycan recognition binding protein expressed by liver tissue. More specifically, isolated nucleic acid molecules are provided encoding a human and murine peptidoglycan recognition protein-related proteins, referred to herein as PGRP-L (Liver), of FIGS. 1A–B and 2A–C, respectively, having homology to both human peptidoglycan recognition protein (PGRP) as well as murine Tag-7. PGRP-L polypeptides are also provided. Further provided are vectors, host cells and recombinant methods for producing the same. The invention also relates to both the inhibition and enhancement of activities of PGRP-L polypeptides and diagnostic methods for detecting PGRP-L gene expression.

BACKGROUND OF THE INVENTION

Peptidoglycan, as well as lipopolysaccharide (LPS), is a surface component of many bacteria, which elicits a wide range of physiological and immune responses in humans. Specifically, peptidoglycan has been shown to manifest itself clinically by reproducing most of the symptoms of bacterial infection, including fever, acute-phase response, inflammation, septic shock, leukocytosis, sleepiness, malaise, abscess formation, and arthritis (see Dziarski et al., JBC, 273 (15): 8680 (1998)). Furthermore, the type of peptidoglycan (i.e.—the specific stereoisomers or analogs of muramyl dipeptide, N-acetylglucosaminyl-beta(1-4)-N-acteylmuramyl tetrapeptides, etc.), were shown to elicit a broad range of activities, including exhibiting greater pyrogenicity, inducing acute joint inflammation, stimulating macrophages, and causing hemorrhagic necrosis at a primed site (See Kotani et al., Fed Proc, 45(11): 2534 (1986)).

It has been demonstrated in humans that a lipopolysaccharide binding protein exists that was discovered as a trace plasma protein (See Schumann et al., Science, 249(4975): 1429 (1990)). It is thought that one of the modes of action by which this lipopolysaccharide binding protein functions is by forming high-affinity complexes with lipopolysaccharide, that then bind to macrophages and monocytes, inducing the secretion of tumor necrosis factor. Dziarski and Gupta (See Dziarski et al., JBC, 269(3): 2100 (1994)) demonstrated that a 70 kDa receptor protein present on the surface of mouse lymphocytes served to bind heparin, heparinoids, bacterial lipoteichoic acids, peptidoglycan, and lipopolysaccharides.

Recently, Dziarski et al. demonstrated that the CD14, a glycosylphosphatidylinositol-linked protein present on the surface of macrophage and polymorphonuclear leukocytes, bound peptidoglycan and lipopolysaccharide. Furthermore, the binding affinity of CD14 for lipopolysaccharide was significantly increased in the presence of a LPS-binding protein present in plasma. It is thought that the LPS-binding protein functions as a transfer molecule, whereby it binds LPS and presents it to the CD14 receptor (See Dziarski et al., JBC, 273(15): 8680 (1998)).

Yoshida et al. isolated a peptidoglycan binding protein from the hemolymph of the Silkworm, *Bombyx mori*, using column chromatography. This protein was found to have a very specific affinity for peptidoglycan (See Yoshida et al., JBC, 271(23): 13854 (1996)). Additionally, Kang et al. recently cloned a peptidoglycan binding protein from the moth *Trichoplusia ni*. The peptidoglycan binding protein was shown to bind strongly to insoluble peptidoglycan (See Kang et al., PNAS, 95(17): 10078 (1998)). In this study the peptidoglycan binding protein was upregulated by a bacterial infection in *T. ni*. The insect immune system is regarded as a model for innate immunity. Thus, Kang et al were able to clone both mouse and human homologs of the *T. ni* peptidoglycan binding protein. All of these peptidoglycan binding proteins shared regions of homology, as well as four conserved cysteine residues which may function in the tertiary structure of the protein, possibly in helping to form binding domains. Given that peptidoglycan is an integral component of bacterial cell walls, and that it induces many physiological responses from cytokine secretion to inflammation and macrophage activation, it appears as if this family of proteins may be a ubiquitous group involved in the binding and recognition of peptidoglycan, the presentation of antigens (e.g., cell wall components, etc.), and the activation of the immune system, such as the secretion of cytokines, such as TNF.

TNF is noted for its pro-inflammatory actions which result in tissue injury, such as induction of procoagulant activity on vascular endothelial cells (Pober, J. S. et al., *J. Immunol.* 136:1680 (1986)), increased adherence of neutrophils and lymphocytes (Pober, J. S. et al., *J. Immunol.* 138:3319 (1987)), and stimulation of the release of platelet activating factor from macrophages, neutrophils and vascular endothelial cells (Camussi, G. et al., *J. Exp. Med.* 166:1390 (1987)).

Recent evidence implicates TNF in the pathogenesis of many infections (Cerami, A. et al., *Immunol. Today* 9:28 (1988)), immune disorders, neoplastic pathology, e.g., in cachexia accompanying some malignancies (Oliff, A. et al., *Cell* 50:555 (1987)), and in autoimmune pathologies and graft-versus host pathology (Piguet, P.-F. et al., *J. Exp. Med.* 166:1280 (1987)). The association of TNF with cancer and infectious pathologies is often related to the host's catabolic state. A major problem in cancer patients is weight loss, usually associated with anorexia. The extensive wasting which results is known as "cachexia" (Kern, K. A. et al *J. Parent. Enter. Nutr.* 12:286–298 (1988)). Cachexia includes progressive weight loss, anorexia, and persistent erosion of body mass in response to a malignant growth. The cachectic state is thus associated with significant morbidity and is responsible for the majority of cancer mortality. A number of studies have suggested that TNF is an important mediator of the cachexia in cancer, infectious pathology, and in other catabolic states.

TNF is thought to play a central role in the pathophysiological consequences of Gram-negative sepsis and endotoxic shock (Michie, H. R. et al., *Br. J. Surg.* 76:670–671 (1989); Debets, J. M. H. et al., *Second Vienna Shock Forum,* p.463–466 (1989); Simpson, S. Q. et al., *Crit. Care Clin.* 5:27–47 (1989)), including fever, malaise, anorexia, and cachexia. Endotoxin is a potent monocyte/macrophage activator, which stimulates production and secretion of TNF (Kombluth, S. K. et al., *J. Immunol.* 137:2585–2591 (1986)) and other cytokines. Because TNF could mimic many biological effects of endotoxin, it was concluded to be a central mediator responsible for the clinical manifestations of endotoxin-related illness. TNF and other monocyte-derived cytokines mediate the metabolic, neurological and hormonal responses to endotoxin (Michie, H. R. et al., *N. Eng. J. Med.* 318:1481–1486 (1988)). Endotoxin administration to human volunteers produces acute illness with flu-like symptoms including fever, tachycardia, increased metabolic rate and stress hormone release (Revhaug, A. et al., *Arch. Surg.* 123:162–170 (1988)). Elevated levels of circulating TNF have also been found in patients suffering from Gram-negative sepsis (Waage, A. et al., *Lancet* 1:355–357 (1987); Hammerle, A. F. et al., *Second Vienna Shock Forum* p. 715–718 (1989); Debets, J. M. H. et al., *Crit. Care Med.* 17:489–497 (1989); Calandra, T. et al., *J. Infec. Dis.* 161:982–987 (1990)).

Passive immunotherapy directed at neutralizing TNF may have a beneficial effect in Gram-negative sepsis and endotoxemia, based on the increased TNF production and elevated TNF levels in these pathology states, as discussed above. Antibodies to a "modulator" material which was characterized as cachectin (later found to be identical to TNF) were disclosed by Cerami et al. (EPO Patent Publication 0,212,489, Mar. 4, 1987). Such antibodies were said to be useful in diagnostic immunoassays and in therapy of shock in bacterial infections. Rubin et al. (EPO Patent Publication 0,218,868, Apr. 22, 1987) disclosed monoclonal antibodies to human TNF, the hybridomas secreting such antibodies, methods of producing such antibodies, and the use of such antibodies in immunoassay of TNF. Yone et al. (EPO Patent Publication 0,288,088, Oct. 26, 1988) disclosed anti-TNF antibodies, including mAbs, and their utility in immunoassay diagnosis of pathologies, in particular Kawasaki's pathology and bacterial infection. The body fluids of patients with Kawasaki's pathology (infantile acute febrile mucocutaneous lymph node syndrome; Kawasaki, T., *Allergy* 16:178 (1967); Kawasaki, T., *Shonica* (*Pediatrics*) 26:935 (1985)) were said to contain elevated TNF levels, which were related to progress of the pathology (Yone et al., supra).

Kiselev et al. isolated tag7, which is a secreted murine cytokine with remote homology to the TNF family of ligands (Kiselev, S. L., et al, J. Biol. Chem., 273:18633–39 (1998)). It was found that tag7 triggers apoptosis in murine L929 cells in vitro, and thus may be a molecule that possesses significant cytotoxicity in vivo that is realized through apoptosis. Furthermore, tag7 is expressed constitutively in hematopoietic and lymphoid tissues, suggesting that it may play a role in normal immune system function.

Accordingly, there is a need to provide molecules that are involved in pathological conditions. Such novel proteins could be useful in augmenting the immune system in such areas as immune recognition, antigen presentation, and immune system activation. Antibodies or antagonists directed against these proteins may be useful in reducing or eliminating disorders associated with TNF and TNF-like cytokines, such as endotoxic shock and auto-immune disorders, for example.

SUMMARY OF THE INVENTION

The present invention relates to novel polynucleotides and the encoded polypeptides of human and murine PGRP-L (collectively referred to herein as PGRP-L). Moreover, the present invention relates to vectors, host cells, antibodies, and recombinant methods for producing the polypeptides and polynucleotides. Also provided are diagnostic methods for detecting disorders and conditions related to PGRP-L, and therapeutic methods for treating or preventing such disorders or conditions. The invention further relates to screening methods for identifying binding partners of PGRP-L.

BRIEF DESCRIPTION OF THE DRAWINGS

FIGS. 1A–B show the nucleotide sequence (SEQ ID NO:1) and deduced amino acid sequence (SEQ ID NO:2) of human PGRP-L (hPGRP-L). The deduced amino acid sequence includes 174 amino acid residues and has a deduced molecular weight of about 18,595 Da.

FIGS. 2A–C show the nucleotide sequence (SEQ ID NO:3) and deduced amino acid sequence (SEQ ID NO:4) of murine PGRP-L (mPGRP-L). The deduced complete amino acid sequence includes 530 amino acid residues and has a deduced molecular weight of about 57,764 Da. The murine PGRP-L amino acid sequence shares 91% homology with the human PGRP-L amino acid sequence over a stretch of 174 amino acids, as depicted in FIG. 3A-B. The full-length mPGRP-L contains a signal sequence from about amino acid Met-1 to about amino acid Ala-22, with the mature mPGRP-L starting at about amino acid Ser-23.

FIGS. 3A–B show the regions of similarity between the amino acid sequences of the human PGRP-L protein of FIGS. 1A–B (labeled hPGRP-L; SEQ ID NO:2) and the murine PGRP-L protein of FIGS. 2A–C (labeled mPGRP-L; SEQ ID NO:4), as determined by the "Megalign" routine which is part of the computer program called "DNAStar". Identical amino acid residues between these protein sequences are shaded.

Figure 4:
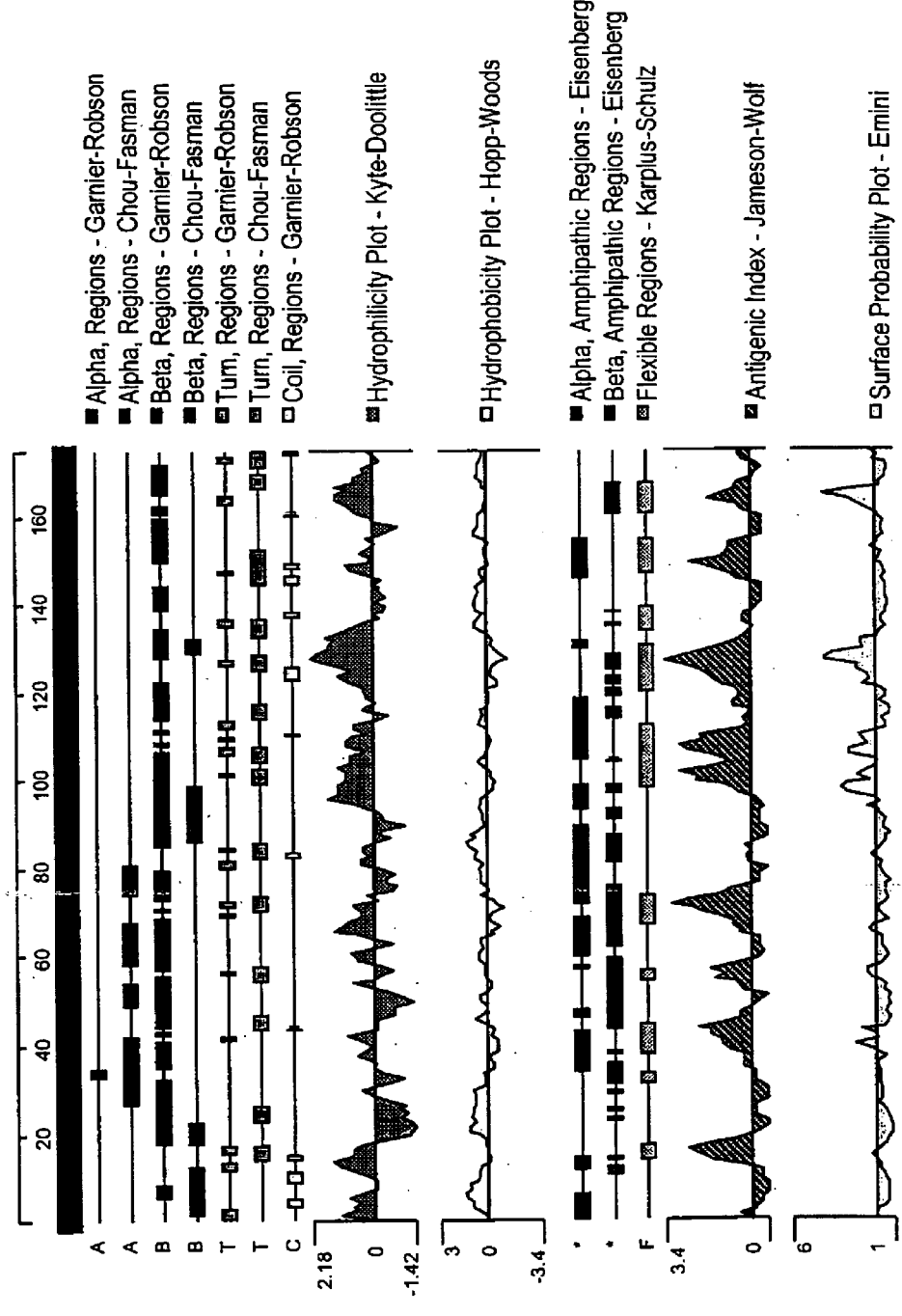
FIG. 4 and Table I show a structural analysis of the human PGRP-L amino acid sequence of FIGS. 1A–B (SEQ ID NO:2), generated using the default parameters of the recited computer programs. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues: Gly-12 to Phe-18; from Ala-34 to Ala-47; from Gly-51 to Tyr-57; from Gln-64 to Leu-75; from Arg-80 to His-84; from Thr-96 to Tyr-133; from Gly-135 to Leu-137; from Ser-145 to Thr-154; from Ala-161 to Pro-167; and from Pro-172 to Ser-174 as depicted in FIGS. 1A–B (SEQ ID NO:2) correspond to the shown highly antigenic regions of the human PGRP-L protein.
Figure 5:
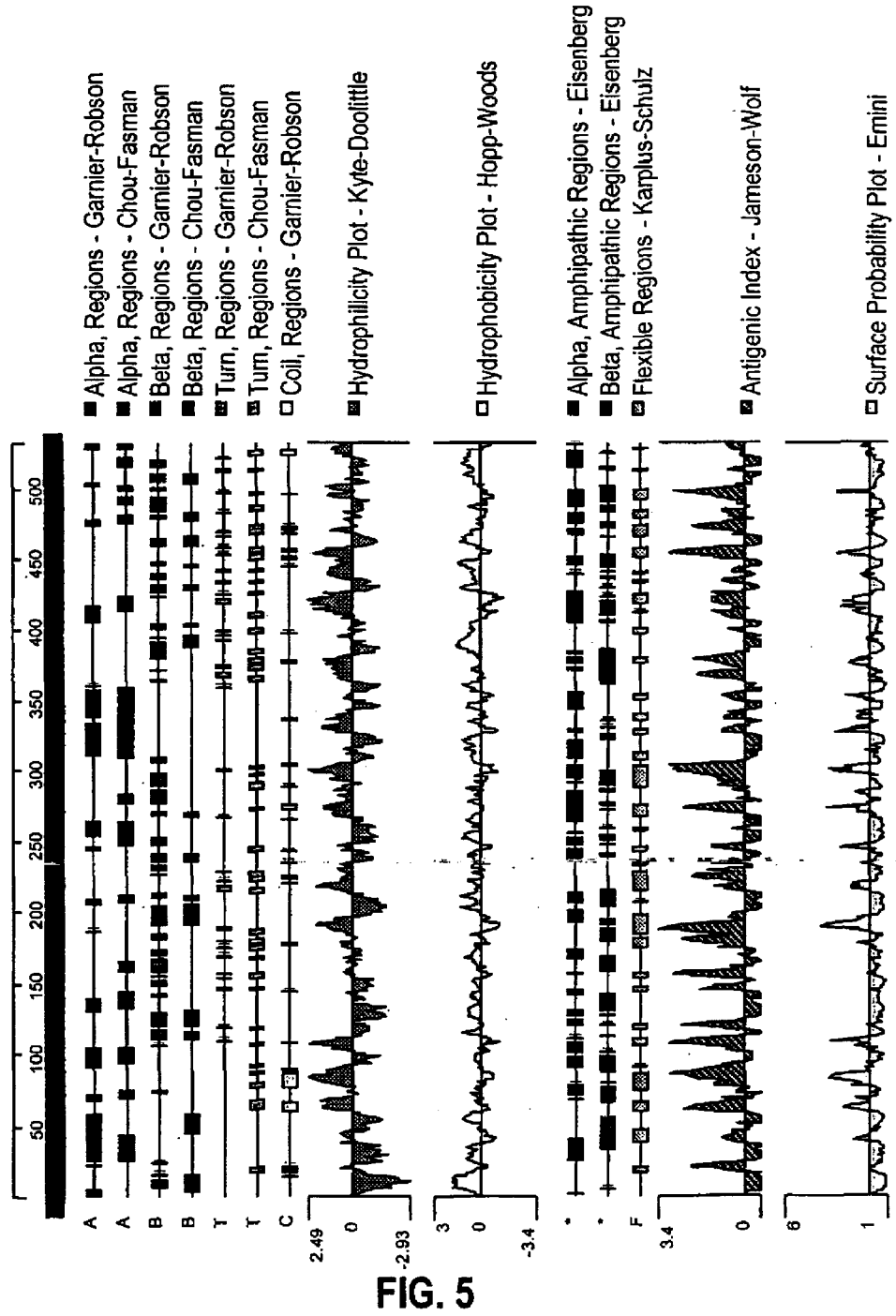
FIG. 5 and Table II show a structural analysis of the murine PGRP-L amino acid sequence of FIGS. 2A–B (SEQ ID NO:4), generated using the default parameters of the recited computer programs. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues: Glu-18 to Ser-24; from Ala-37 to Val-45; from Ala-59 to Leu-68; from Ala-76 to Leu-93; from Ala-101 to Tyr-111; from Ala-116 to Val-122; from Leu-143 to Ala-159; from Phe-172 to Arg-197; from His-213 to Trp-229; from Asp-242 to Ser-246; from Gln-268 to Pro-275; from Val-288 to Ala-305; from Lys-325 to His-330; from Asn-335 to Gln-340; from Ala-348 to Thr-353; from Ile-362 to Leu-382; from Pro-397 to Cys-399; from Ala-406 to Gln-413; from Phe-415 to Gly-426; from Gly-432 to Gly-435; from Gly-440 to Gly-442; from His-449 to Gly-457; from Tyr-466 to Ala-475; from Thr-478 to Pro-484; from Cys-486 to Leu-499; from Pro-511 to Asn-513; and from Thr-521 to Asn-530 as depicted in FIGS. 2A–C (SEQ ID NO:4) correspond to the shown highly antigenic regions of the murine PGRP-L protein.

The data presented in FIGS. 4 and 5 are also represented in tabular form in Tables I and II. The columns are labeled with the headings "Res", "Position", and Roman Numerals I–XIV. The column headings refer to the following features of the amino acid sequences presented in FIGS. 1A–B and 2A–C, and Tables I and II: "Res": amino acid residue of SEQ ID NO:2 and SEQ ID NO:4 and FIGS. 1A–B and 2A–C; "Position": position of the corresponding residue within SEQ ID NO:2 and SEQ ID NO:4 and FIGS. 1A–B and 2A–B; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" PGRP-L protein refers to a protein capable of being directed to the ER, secretory vesicles, or the extracellular space as a result of a signal sequence, as well as a PGRP-L protein released into the extracellular space without necessarily containing a signal sequence. If the PGRP-L secreted protein is released into the extracellular space, the PGRP-L secreted protein can undergo extracellular processing to produce a "mature" PGRP-L protein. Release into the extracellular space can occur by many mechanisms, including exocytosis and proteolytic cleavage.

As used herein, a human PGRP-L "polynucleotide" refers to a molecule having a nucleic acid sequence contained in SEQ ID NO:1 or the cDNA contained within the clone HPJEV37, deposited with the ATCC. For example, the human PGRP-L polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a human PGRP-L "polypeptide" refers to a molecule having the translated amino acid sequence generated from the polynucleotide as broadly defined.

In specific embodiments, the polynucleotides of the invention are less than 1200 bp, 800 bp, 600 bp, 400 bp, 200 bp, 100 bp, or 50 bp in length. In a further embodiment, polynucleotides of the invention comprise at least 15 contiguous nucleotides of PGRP-L coding sequence, but do not comprise all or a portion of any PGRP-L intron. In another embodiment, the nucleic acid comprising PGRP-L coding sequence does not contain coding sequences of a genomic flanking gene (i.e., 5' or 3' to the PGRP-L gene in the genome).

In the present invention, the human PGRP-L sequence shown in FIGS. 1A–B (SEQ ID NO:1) was generated by overlapping sequences of the deposited clone (contig analysis). A representative clone containing all or most of the sequence shown in FIGS. 1A–B (SEQ ID NO:1) was deposited with the American Type Culture Collection ("ATCC") on Aug. 7, 2000, and was given the ATCC Deposit Number PTA-2330. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A PGRP-L "polynucleotide" also includes those polynucleotides capable of hybridizing, under stringent hybridization conditions, to sequences disclosed in FIGS. 1A–B (SEQ ID NO:1), the complement thereof, sequences disclosed in FIGS. 2A–B (SEQ ID NO:3), the complement thereof, or the cDNA within the deposited clone. "Stringent hybridization conditions" refers to an overnight incubation at 42 degree C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65 degree C.

Also contemplated are polynucleotides that hybridize to the PGRP-L polynucleotides at moderately high stringency hybridization conditions. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37 degree C. in a solution comprising 6×SSPE (20×SSPE=3M NaCl; 0.2M NaH$_2$PO$_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo-dT as a primer).

The PGRP-L polynucleotide can be composed of any polyribonucleotide or polydeoxribonucleotide, which may be unmodified RNA or DNA or modified RNA or DNA. For example, PGRP-L polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the PGRP-L polynucleotides can be composed of triple-stranded regions comprising RNA or DNA or both RNA and DNA. PGRP-L polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

PGRP-L polypeptides can be composed of amino acids joined to each other by peptide bonds or modified peptide bonds, i.e., peptide isosteres, and may contain amino acids other than the 20 gene-encoded amino acids. The PGRP-L polypeptides may be modified by either natural processes, such as post-translational processing, or by chemical modification techniques which are well known in the art. Such modifications are well described in basic texts and in more detailed monographs, as well as in voluminous research literature. Modifications can occur anywhere in the PGRP-L polypeptide, including the peptide backbone, the amino acid side-chains and the carboxyl termini. It will be appreciated that the same type of modification may be present in the same or varying degrees at several sites in a given PGRP-L polypeptide. Also, a given PGRP-L polypeptide may contain many types of modifications. PGRP-L polypeptides may be branched, for example, as a result of ubiquitination, and they may be cyclic, with or without branching. Cyclic, branched, and branched cyclic PGRP-L polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:1" refers to the human PGRP-L polynucleotide sequence while "SEQ ID NO:2" refers to the human PGRP-L polypeptide sequence.

A PGRP-L polypeptide "having biological activity" refers to polypeptides exhibiting activity similar, but not necessarily identical to, an activity of a PGRP-L polypeptide (e.g., a human PGRP-L polypeptide and/or a murine PGRP-L polypeptide), including mature forms, as measured in a particular biological assay, with or without dose dependency. In the case where dose dependency does exist, it need not be identical to that of the PGRP-L polypeptide, but rather substantially similar to the dose-dependence in a given activity as compared to the PGRP-L polypeptide (i.e., the candidate polypeptide will exhibit greater activity or not more than about 25-fold less and, preferably, not more than about tenfold less activity, and most preferably, not more than about three-fold less activity relative to the PGRP-L polypeptide.)

PGRP-L Polynucleotides and Polypeptides

The protein encoded by the nucleotide sequence shown in FIGS. 2A–B (SEQ ID NO:3) is a full-length murine PGRP-L (mPGRP-L) protein. The predicted molecular weight of the murine PGRP-L protein is about 57.8 kDa.

Clone HPJEV37 was isolated from a human PC3 Prostate derived cell line cDNA library. This clone contains the entire coding region identified in FIGS. 1A–B. The deposited clone contains a cDNA having a total of approximately 1200 nucleotides, which encodes a predicted open reading frame of 174 amino acid residues. (See FIGS. 1A–B.) The open reading frame begins at an Arginine residue encoded by nucleotides 3 to 5, and ends at a stop codon encoded by nucleotides 525 to 527. The protein encoded by the nucleotide sequence disclosed in FIGS. 1A–B (SEQ ID NO:1) is a partial amino acid sequence of the full-length human PGRP-L protein. As described in more detail infra, it would be routine for one skilled in the art to isolate the full-length cDNA encoding the full-length human PGRP-L protein. The predicted molecular weight of the partial human PGRP-L protein is about 18.6 kDa.

Subsequent Northern analysis demonstrated strong expression of hPGRP-L in liver tissue. A single primary transcript of approximately 2–2.5 kb is observed, with a minor transcript of approximately 1.0 kb that likely represents an unprocessed RNA precursor or alternative splice variant. The expression of the major 2–2.5 kb transcript is highest in liver tissue.

The HPGRP-L nucleotide sequence identified as SEQ ID NO:1 was assembled from partially homologous ("overlapping") sequences obtained from the deposited clone. The overlapping sequences were assembled into a single contiguous sequence of high redundancy resulting in a final sequence shown in FIGS. 1A–B (SEQ ID NO:1).

Therefore, SEQ ID NO:1 and the translated SEQ ID NO:2, and SEQ ID NO:3 and the translated SEQ ID NO:4, are sufficiently accurate and otherwise suitable for a variety of uses well known in the art and described further below. For instance, SEQ ID NO:1 or SEQ ID NO:3 are useful for designing nucleic acid hybridization probes that will detect nucleic acid sequences contained in SEQ ID NO:1, SEQ ID NO:3 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2 or SEQ ID NO:4 may be used to generate antibodies, which bind specifically to hPGRP-L and/or mPGRP-L.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2, but also a sample of plasmid DNA containing a human cDNA of hPGRP-L deposited with the ATCC. The nucleotide sequence of the deposited hPGRP-L clone can readily be determined by sequencing the deposited clone in accordance with known methods. The predicted hPGRP-L amino acid sequence can then be verified from such deposits. Moreover, the amino acid sequence of the protein encoded by the deposited clone can also be directly determined by peptide sequencing or by expressing the protein in a suitable host cell containing the deposited human PGRP-L cDNA, collecting the protein, and determining its sequence.

The present invention relates to polynucleotides comprising, or alternatively, consisting of a polynucleotide sequence encoding the hPGRP-L polypeptide shown in FIGS. 1A–B, the polynucleotide coding sequence shown in FIGS. 1A–B (SEQ ID NO:1), the PGRP polypeptide shown in FIGS. 2A–B, the polynucleotide coding sequence shown in FIGS. 2A–B (SEQ ID NO:3), and the complementary strand thereto. Polypeptides encoded by these polynucleotides are also encompassed by the invention.

The present invention also relates to the hPGRP-L gene corresponding to SEQ ID NO:1, SEQ ID NO:2, or the deposited clone. The hPGRP-L gene can be isolated in accordance with known methods using the sequence information disclosed herein. Such methods include preparing probes or primers from the disclosed sequence and identifying or amplifying the hPGRP-L gene from appropriate sources of genomic material.

Also provided in the present invention are allelic variants, species homologs and orthologs of PGRP-L. Species homologs may be isolated and identified by making suitable probes or primers from the sequences provided herein and screening a suitable nucleic acid source for the desired homologue.

The PGRP-L polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The PGRP-L polypeptides of the invention may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

PGRP-L polypeptides are preferably provided in an isolated form, and preferably are substantially purified. A recombinantly produced version of a PGRP-L polypeptide, including the secreted polypeptide, can be substantially purified by the one-step method described in Smith and Johnson, Gene 67:31–40 (1988). PGRP-L polypeptides also can be purified from natural or recombinant sources using antibodies of the invention raised against the PGRP-L protein in methods, which are well known in the art.

Several methods are available for the identification of the 5' or 3' portions of the human PGRP-L gene, which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7): 1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the human PGRP-L gene of interest is used to PCR amplify the 5' portion of the human PGRP-L full-length gene, respectively. This amplified product may then be sequenced and used to generate the full-length gene.

This above method starts with total RNA isolated from the desired source, although poly-A+ RNA can be used. The RNA preparation can then be treated with phosphatase if necessary to eliminate 5' phosphate groups on degraded or damaged RNA, which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA, which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the human PGRP-L gene.

Alternatively, a genomic clone comprising the human PGRP-L coding exons can be isolated by screening a human genomic library as discussed infra. Once positive clones have been identified, the DNA inserts contained in the genomic clone can be isolated, and the DNA sequenced. Once the DNA sequence has been determined, the utilization of a number of computer-based DNA sequence analysis programs, such as, for example, BLAST and GRAIL, will allow the identification of the coding exons and the non-coding introns associated with the human PGRP-L gene, and hence the identification of any 5' portion of the human PGRP-L full-length gene which may not have been previously present in the deposited clone.

Polynucleotide and Polypeptide Fragments

The present invention is further directed to fragments of the isolated nucleic acid molecules described herein. By a fragment of an isolated nucleic acid molecule having, for example, the nucleotide sequence of the deposited cDNA (clone HPJEV37), a nucleotide sequence encoding the polypeptide sequence encoded by the deposited cDNA, a nucleotide sequence encoding the polypeptide sequence depicted in FIGS. 1A–B (SEQ ID NO:2), the nucleotide sequence shown in FIGS. 1A–B (SEQ ID NO:1), or the complementary strand thereto, a nucleotide sequence encoding the polypeptide sequence depicted in FIGS. 2A–B (SEQ ID NO:4), the nucleotide sequence shown in FIGS. 2A–B (SEQ ID NO:3), or the complementary strand thereto, is intended PGRP-L polynucleotides at least 15 nt, and more preferably at least about 20 nt, still more preferably at least 30 nt, and even more preferably, at least about 40, 50, 100, 150, 200, 250, 300, 325, 350, 375, 400, 450, 500, 550, or 600 nt in length. These fragments have numerous uses that include, but are not limited to, diagnostic probes and primers as discussed herein. Of course, larger fragments, such as those of 601–1500 nt in length are also useful according to the present invention as are fragments corresponding to most, if not all, of the nucleotide sequences of the deposited cDNA (clone HPJEV37) as shown in FIGS. 1A–B (SEQ ID NO:1), as shown in FIGS. 2A–B, or the complementary strand thereto. By a fragment at least 20 nt in length, for example, is intended fragments which include 20 or more contiguous bases from, for example, the nucleotide sequence of the deposited cDNA, or the nucleotide sequence as shown in FIGS. 1A–B (SEQ ID NO:1), or the nucleotide sequence as shown in FIGS. 2A–B (SEQ ID NO:3). In this context "about" includes the particularly recited ranges, larger or smaller by several (5, 4, 3, 2, or 1) nucleotides, at either terminus or at both termini. Polypeptides encoded by these polynucleotides are also encompassed by the invention.

Moreover, representative examples of hPGRP-L (clone HPJEV37) polynucleotide fragments include, for example, fragments having a sequence from about nucleotide number 3–53, 54–104, 105–152, 153–200, 201–251, 252–302, 303–350, 351–401, 402–452, and/or 453–514 to the end of SEQ ID NO:1 (FIGS. 1A–B) or the complementary strand thereto, or the cDNA contained in the deposited clone. Moreover, representative examples of polynucleotide fragments of the sequence disclosed in FIGS. 2A–B, include for example, fragments having a sequence from about nucleotide number 157–198, 199–258, 259–309, 310–360, 361–411, 412–459, 460–510, 511–561, 562–609, 610–660, 661–711, 712–762, 763–813, 814–864, 865–915, 916–966, 967–1017, 1018–1068, 1069–1119, 1120–1170, 1171–1221, 1222–1272, 1273–1323, 1324–1374, 1375–1425, 1426–1476, 1477–1527, 1528–1578, 1579–1629, 1630–1680, 1681–1731, 1732–1746, and/or 1423–1503, of the sequence disclosed in FIGS. 2A–B, or the complementary strand thereto. In this context "about" includes the particularly recited ranges, larger or smaller by several (5, 4, 3, 2, or 1) nucleotides, at either terminus or at both termini. Polypeptides encoded by these polynucleotides are also encompassed by the invention. The invention also encompasses polynucleotides that hybridize to one or more of the above-recited polynucleotides under moderately high stringency hybridization conditions and/or stringent hybridization conditions. Polypeptides encoded by these polynucleotide fragments and polynucleotides are also encompassed by the invention.

Preferably, the polynucleotide fragments of the invention encode a polypeptide, which demonstrates a PGRP-L functional activity. By a polypeptide demonstrating a PGRP-L "functional activity" is meant, a polypeptide capable of displaying one or more known functional activities associated with a PGRP-L protein. Such functional activities include, but are not limited to, apoptosis (e.g., see Examples 38 and 39), peptidoglycan binding (e.g., see Example 37), biological activity, antigenicity [ability to bind (or compete with a PGRP-L polypeptide for binding) to an anti-PGRP-L antibody], immunogenicity (ability to generate antibody which binds to a PGRP-L polypeptide), ability to form multimers with PGRP-L polypeptides of the invention, and ability to bind to a receptor or ligand for a PGRP-L polypeptide.

The functional activity of PGRP-L polypeptides, and fragments, variants, derivatives, and analogs thereof, can be assayed by various methods.

For example, in one embodiment where one is assaying for the ability to bind or compete with PGRP-L polypeptide for binding to anti-PGRP-L antibody (e.g., anti-hPGRP-L and/or anti-mPGRP-L), various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a PGRP-L ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of PGRP-L binding to its substrates (signal transduction) can be assayed.

In addition, assays described herein (see Examples) and otherwise known in the art may routinely be applied to measure the ability of PGRP-L polypeptides and fragments, variants derivatives and analogs thereof to elicit PGRP-L related biological activity (either in vitro or in vivo). Other methods will be known to the skilled artisan and are within the scope of the invention.

The present invention is further directed to fragments of the PGRP-L polypeptide described herein. By a fragment of an isolated PGRP-L polypeptide, for example, encoded by the deposited cDNA (clone HPJEV37), the polypeptide sequence depicted in FIGS. 1A–B (SEQ ID NO:2), and/or the polypeptide sequence depicted in FIGS. 2A–B (SEQ ID NO:4), is intended to encompass polypeptide fragments contained in SEQ ID NO:2, SEQ ID NO:4, and/or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161–174 of the amino acid sequence disclosed in FIGS. 1A–B (SEQ ID NO:2). Representative examples of polypeptide fragments of the invention, include, for example, fragments from about amino acid number 1–20, 21–40, 41–60, 61–80, 81–100, 102–120, 121–140, 141–160, or 161–200, 201–250, 251–300, 301–350, 351–400, 401–450, 451–500, and/or 500–530 of the amino acid sequence disclosed in FIGS. 2A–B (SEQ ID NO:4). Moreover, polypeptide fragments can be at least 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes. Polynucleotides encoding these polypeptides are also encompassed by the invention.

Even if deletion of one or more amino acids from the N-terminus of a protein results in modification of loss of one or more biological functions of the protein, other functional activities (e.g., biological activities, ability to multimerize, ability to bind PGRP-L ligand) may still be retained. For example, the ability of shortened PGRP-L muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an PGRP-L mutein with a large number of deleted N-terminal amino acid residues may retain some biological or immunogenic activities. In fact, peptides composed of as few as six PGRP-L amino acid residues may often evoke an immune response.

Accordingly, preferred polypeptide fragments include the hPGRP-L protein shown in FIGS. 1A–B having a continuous series of deleted residues from the amino or the carboxy terminus, or both. For example, any number of amino acids, ranging from 1–60, can be deleted from the amino terminus of the hPGRP-L polypeptide shown in FIGS. 1A–B. Similarly, any number of amino acids, ranging from 1–30, can be deleted from the carboxy terminus of the hPGRP-L protein shown in FIGS. 1A–B. Furthermore, any combination of the above amino and carboxy terminus deletions are preferred. Similarly, polynucleotide fragments encoding these hPGRP-L polypeptide fragments are also preferred.

Particularly, N-terminal deletions of the hPGRP-L polypeptide shown in FIGS. 1A–B can be described by the general formula m to PGRP-L, where m is an integer from 2 to 173, where m corresponds to the position of the amino acid residue identified in FIGS. 1A–B (SEQ ID NO:2). More in particular, the invention provides polynucleotides encoding polypeptides comprising, or alternatively consisting of, the amino acid sequence of residues of: G-2 to S-174; W-3 to S-174; H-4 to S-174; W-5 to S-174; V-6 to S-174; G-7 to S-174; A-8 to S-174; H-9 to S-174; T-10 to S-174; L-11 to S-174; G-12 to S-174; H-13 to S-174; N-14 to S-174; S-15 to S-174; R-16 to S-174; G-17 to S-174; F-18 to S-174; G-19 to S-174; V-20 to S-174; A-21 to S-174; I-22 to S-174; V-23 to S-174; G-24 to S-174; N-25 to S-174; Y-26 to S-174; T-27 to S-174; A-28 to S-174; A-29 to S-174; L-30 to S-174; P-31 to S-174; T-32 to S-174; E-33 to S-174; A-34 to S-174; A-35 to S-174; L-36 to S-174; R-37 to S-174; T-38 to S-174; V-39 to S-174; R-40 to S-174; D-41 to S-174; T-42 to S-174; L-43 to S-174; P-44 to S-174; S-45 to S-174; C-46 to S-174; A-47 to S-174; V-48 to S-174; R-49 to S-174; A-50 to S-174; G-51 to S-174; L-52 to S-174; L-53 to S-174; R-54 to S-174; P-55 to S-174; D-56 to S-174; Y-57 to S-174; A-58 to S-174; L-59 to S-174; L-60 to S-174; G-61 to S-174; H-62 to S-174; R-63 to S-174; Q-64 to S-174; L-65 to S-174; V-66 to S-174; R-67 to S-174; T-68 to S-174; D-69 to S-174; C-70 to S-174; P-71 to S-174; G-72 to S-174; D-73 to S-174; A-74 to S-174; L-75 to S-174; F-76 to S-174; D-77 to S-174; L-78 to S-174; L-79 to S-174; R-80 to S-174; T-81 to S-174; W-82 to S-174; P-83 to S-174; H-84 to S-174; F-85 to S-174; T-86 to S-174; A-87 to S-174; V-88 to S-174; S-89 to S-174; L-90 to S-174; R-91 to S-174; S-92 to S-174; L-93 to S-174; H-94 to S-174; Y-95 to S-174; T-96 to S-174; A-97 to S-174; R-98 to S-174; R-99 to S-174; P-100 to S-174; S-101 to S-174; V-102 to S-174; Y-103 to S-174; T-104 to S-174; S-105 to S-174; S-106 to S-174; T-107 to S-174; R-108 to S-174; P-109 to S-174; L-110 to S-174; P-111 to S-174; P-112 to S-174; A-113 to S-174; C-114 to S-174; N-115 to S-174; S-116 to S-174; C-117 to S-174; A-118 to S-174; R-119 to S-174; T-120 to S-174; A-121 to S-174; S-122 to S-174; A-123 to S-174; R-124 to S-174; P-125 to S-174; P-126 to S-174; T-127 to S-174; S-128 to S-174; R-129 to S-174; R-130 to S-174; H-131 to S-174; V-132 to S-174; Y-133 to S-174; S-134 to S-174; G-135 to S-174; N-136 to S-174; L-137 to S-174; G-138 to S-174; P-139 to S-174; A-140 to S-174; F-141 to S-174; A-142 to S-174; G-143 to S-174; H-144 to S-174; S-145 to S-174; A-146 to S-174; G-147 to S-174; N-148 to S-174; I-149 to S-174; P-150 to S-174; D-151 to S-174; P-152 to S-174; V-153 to S-174; T-154 to S-174; S-155 to S-174; A-156 to S-174; Y-157 to S-174; A-158 to S-174; A-159 to S-174; S-160 to S-174; A-161 to S-174; Q-162 to S-174; P-163 to S-174; Q-164 to S-174; T-165 to S-174; Q-166 to S-174; P-167 to S-174; A-168 to S-174; C-169 to S-174; of FIGS. 1A–B (SEQ ID NO:2). Polypeptides encoded by these polynucleotides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind PGRP-L ligand) may still be retained. For example, the ability of the shortened PGRP-L mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an PGRP-L mutein with a large number of deleted C-terminal amino acid residues may retain some biological or immunogenic activities. In fact, peptides composed of as few as six PGRP-L amino acid residues may often evoke an immune response.

Accordingly, the present invention further provides polypeptides having one or more residues deleted from the carboxy terminus of the amino acid sequence of the hPGRP-L polypeptide shown in FIGS. 1A–B (SEQ ID NO:2), as described by the general formula 1-n, where n is an integer from 2 to 173, where n corresponds to the position of amino acid residue identified in FIGS. 1A–B (SEQ ID NO:2). More in particular, the invention provides polynucleotides encoding polypeptides comprising, or alternatively consisting of, the amino acid sequence of residues of R-1 to S-173; R-1 to P-172; R-1 to F-171; R-1 to P-170; R-1 to C-169; R-1 to A-168; R-1 to P-167; R-1 to Q-166; R-1 to T-165; R-1 to Q-164; R-1 to P-163; R-1 to Q-162; R-1 to A-161; R-1 to S-160; R-1 to A-159; R-1 to A-158; R-1 to Y-157; R-1 to A-156; R-1 to S-155; R-1 to T-154; R-1 to V-153; R-1 to P-152; R-1 to D-151; R-1 to P-150; R-1 to I-149; R-1 to N-148; R-1 to G-147; R-1 to A-146; R-1 to S-145; R-1 to H-144; R-1 to G-143; R-1 to A-142; R-1 to F-141; R-1 to A-140; R-1 to P-139; R-1 to G-138; R-1 to L-137; R-1 to N-136; R-1 to G-135; R-1 to S-134; R-1 to Y-133; R-1 to V-132; R-1 to H-131; R-1 to R-130; R-1 to R-129; R-1 to S-128; R-1 to T-127; R-1 to P-126; R-1 to P-125; R-1 to R-124; R-1 to A-123; R-1 to S-122; R-1 to A-121; R-1 to T-120; R-1 to R-119; R-1 to A-118; R-1 to C-117; R-1 to S-116; R-1 to N-115; R-1 to C-114; R-1 to A-113; R-1 to P-112; R-1 to P-111; R-1 to L-110; R-1 to P-109; R-1 to R-108; R-1 to T-107; R-1 to S-106; R-1 to S-105; R-1 to T-104; R-1 to Y-103; R-1 to V-102; R-1 to S-101; R-1 to P-100; R-1 to R-99; R-1 to R-98; R-1 to A-97; R-1 to T-96; R-1 to Y-95; R-1 to H-94; R-1 to L-93; R-1 to S-92; R-1 to R-91; R-1 to L-90; R-1 to S-89; R-1 to V-88; R-1 to A-87; R-1 to T-86; R-1 to F-85; R-1 to H-84; R-1 to P-83; R-1 to W-82; R-1 to T-81; R-1 to R-80; R-1 to L-79; R-1 to L-78; R-1 to D-77; R-1 to F-76; R-1 to L-75; R-1 to A-74; R-1 to D-73; R-1 to G-72; R-1 to P-71; R-1 to C-70; R-1 to D-69; R-1 to T-68; R-1 to R-67; R-1 to V-66; R-1 to L-65; R-1 to Q-64; R-1 to R-63; R-1 to H-62; R-1 to G-61; R-1 to L-60; R-1 to L-59; R-1 to A-58; R-1 to Y-57; R-1 to D-56; R-1 to P-55; R-1 to R-54; R-1 to L-53; R-1 to L-52; R-1 to G-51; R-1 to A-50; R-1 to R-49; R-1 to V-48; R-1 to A-47; R-1 to C-46; R-1 to S-45; R-1 to P-44; R-1 to L-43; R-1 to T-42; R-1 to D-41; R-1 to R-40; R-1 to V-39; R-1 to T-38; R-1 to R-37; R-1 to L-36; R-1 to A-35; R-1 to A-34; R-1 to E-33; R-1 to T-32; R-1 to P-31; R-1 to L-30; R-1 to A-29; R-1 to A-28; R-1 to T-27; R-1 to Y-26; R-1 to N-25; R-1 to G-24; R-1 to V-23; R-1 to I-22; R-1 to A-21; R-1 to V-20; R-1 to G-19; R-1 to F-18; R-1 to G-17; R-1 to R-16; R-1 to S-15; R-1 to N-14; R-1 to H-13; R-1 to G-12; R-1 to L-11; R-1 to T-10; R-1 to H-9; R-1 to A-8; R-1 to G-7; of FIGS. 1A–B (SEQ ID NO:2). Polypeptides encoded by these polynucleotides are also encompassed by the invention.

In addition, any of the above listed N- or C-terminal deletions can be combined to produce a N- and C-terminal deleted hPGRP-L polynucleotide or polypeptide. The invention also provides polypeptides having one or more amino acids deleted from both the amino and the carboxyl termini, which may be described generally as having residues m-n of SEQ ID NO:2, where n and m are integers as described above. Polynucleotides encoding these polypeptides are also encompassed by the invention.

Also included are a nucleotide sequence encoding a polypeptide consisting of a portion of the hPGRP-L amino acid sequence encoded by the cDNA clone contained in ATCC Deposit No. PTA-2330, where this portion excludes any integer of amino acid residues from 1 to about 164 amino acids from the amino terminus of the complete amino acid sequence encoded by the cDNA clone contained in ATCC Deposit No. PTA-2330, or any integer of amino acid residues from 1 to about 164 amino acids from the carboxy terminus, or any combination of the above amino terminal and carboxy terminal deletions, of the complete amino acid sequence encoded by the cDNA clone contained in ATCC Deposit No. PTA-2330. Polynucleotides encoding all of the above deletion mutant polypeptide forms also are provided.

The present application is also directed to proteins containing polypeptides at least 80%, 85%, 90%, 95%, 96%, 97%, 98% or 99% identical to the HPGRP-L polypeptide sequence set forth herein as m-n. In preferred embodiments, the application is directed to proteins containing polypeptides at least 80%, 85%, 90%, 95%, 96%, 97%, 98% or 99% identical to polypeptides having the amino acid sequence of the specific hPGRP-L N- and C-terminal deletions recited herein. Polynucleotides encoding these polypeptides are also encompassed by the invention.

Furthermore, C-terminal deletions of the mPGRP-L polypeptide shown in FIGS. 2A–C can be described by the general formula 1-n, where n is an integer from 2 to 530, where n corresponds to the position of amino acid residue identified in FIGS. 2A–C (SEQ ID NO:4). More in particular, the invention provides polynucleotides encoding polypeptides comprising, or alternatively consisting of, the amino acid sequence of residues of: M-1 to E-529; M-1 to V-528; M-1 to E-527; M-1 to T-526; M-1 to F-525; M-1 to H-524; M-1 to P-523; M-1 to W-522; M-1 to T-521; M-1 to R-520; M-1 to L-519; M-1 to L-518; M-1 to N-517; M-1 to F-516; M-1 to L-515; M-1 to A-514; M-1 to N-513; M-1 to G-512; M-1 to P-511; M-1 to C-510; M-1 to H-509; M-1 to T-508; M-1 to L-507; M-1 to V-506; M-1 to L-505; M-1 to Q-504; M-1 to R-503; M-1 to H-502; M-1 to G-501; M-1 to L-500; M-1 to L-499; M-1 to K-498; M-1 to Y-497; M-1 to D-496; M-1 to P-495; M-1 to R-494; M-1 to L-493; M-1 to L-492; M-1 to G-491; M-1 to E-490; M-1 to R-489;M-1 to I-488; M-1 to A-487; M-1 to C-486; M-1 to S-485; M-1 to P-484; M-1 to L-483; M-1 to A-482; M-1 to D-481; M-1 to R-480; M-1 to V-479; M-1 to T-478; M-1 to N-477; M-1 to L-476; M-1 to A-475; M-1 to A-474; M-1 to E-473; M-1 to N-472; M-1 to P-471; M-1 to L-470; M-1 to S-469; M-1 to G-468; M-1 to T-467; M-1 to Y-466; M-1 to N-465; M-1 to G-464; M-1 to V-463; M-1 to F-462; M-1 to A-461; M-1 to V-460; M-1 to G-459; M-1 to F-458; M-1 to G457; M-1 to R-456; M-1 to S-455; M-1 to N-454; M-1 to Y-453; M-1 to G-452; M-1 to R-451; M-1 to T-450; M-1 to H-449; M-1 to A-448; M-1 to G-447; M-1 to V-446; M-1 to W-445; M-1 to H-444; M-1 to W-443; M-1 to G-442; M-1 to R-441; M-1 to G-440; M-1 to Q-439; M-1 to Y-438; M-1 to L-437; M-1 to Y-436; M-1 to G-435; M-1 to D-434; M-1 to S-433; M-1 to G-432; M-1 to V-431; M-1 to V-430; M-1 to F-429; M-1 to S-428; M-1 to Y-427; M-1 to G-426; M-1 to I-425; M-1 to D-424; M-1 to D-423; M-1 to W-422; M-1 to K-421; M-1 to R-420; M-1 to V-419; M-1 to D-418; M-1 to Q-417; M-1 to H-416; M-1 to F-415; M-1 to R-414; M-1 to Q-413; M-1 to M-412; M-1 to S-411; M-1 to R-410; M-1 to M-409; M-1 to D-408; M-1 to A-407; M-1 to A-406; M-1 to C-405; M-1 to S-404; M-1 to Q-403; M-1 to F-402; M-1 to T-401; M-1 to T-400; M-1 to C-399; M-1 to P-398; M-1 to P-397; M-1 to A-396; M-1 to P-395; M-1 to V-394; M-1 to Y-393; M-1 to T-392; M-1 to H-391; M-1 to H-390; M-1 to V-389; M-1 to Y-388; M-1 to L-387; M-1 to F-386; M-1 to G-385; M-1 to L-384; M-1 to P-383; M-1 to L-382; M-1 to R-381; M-1 to L-380; M-1 to P-379; M-1 to T-378; M-1 to P-377; M-1 to H-376; M-1 to G-375; M-1 to R-374; M-1 to Y-373; M-1 to P-372; M-1 to A-371; M-1 to A-370; M-1 to G-369; M-1 to W-368; M-1 to R-367; M-1 to C-366; M-1 to R-365; M-1 to P-364; M-1 to H-363; M-1 to I-362; M-1 to A-361; M-1 to P-360; M-1 to C-359; M-1 to G-358; M-1 to L-357; M-1 to F-356; M-1 to A-355; M-1 to E-354; M-1 to T-353; M-1 to F-352; M-1 to E-351; M-1 to K-350; M-1 to T-349; M-1 to A-348; M-1 to L-347; M-1 to T-346; M-1 to A-345; M-1 to V-344; M-1 to Q-343; M-1 to A-342; M-1 to L-341; M-1 to Q-340; M-1 to E-339; M-1 to Q-338; M-1 to S-337; M-1 to I-336; M-1 to N-335; M-1 to Q-334; M-1 to L-333; M-1 to Q-332; M-1 to L-331; M-1 to H-330; M-1 to E-329; M-1 to P-328; M-1 to E-327; M-1 to L-326; M-1 to K-325; M-1 to Q-324; M-1 to L-323; M-1 to L-322; M-1 to V-321; M-1 to L-320; M-1 to A-319; M-1 to E-318; M-1 to W-317; M-1 to V-316; M-1 to Q-315; M-1 to Q-314; M-1 to A-313; M-1 to L-312; M-1 to T-311; M-1 to P-310; M-1 to A-309; M-1 to S-308; M-1 to T-307; M-1 to L-306; M-1 to A-305; M-1 to A-304; M-1 to G-303; M-1 to N-302; M-1 to Q-301; M-1 to R-300; M-1 to R-299; M-1 to F-298; M-1 to N-297; M-1 to S-296; M-1 to R-295; M-1 to F-294; M-1 to V-293; M-1 to P-292; M-1 to D-291; M-1 to G-290; M-1 to N-289; M-1 to V-288; M-1 to G-287; M-1 to A-286; M-1 to G-285; M-1 to Y-284; M-1 to Y-283; M-1 to E-282; M-1 to R-281; M-1 to L-280; M-1 to L-279; M-1 to H-278; M-1 to S-277; M-1 to L-276; M-1 to P-275; M-1 to P-274; M-1 to H-273; M-1 to P-272; M-1 to R-271; M-1 to P-270; M-1 to I-269; M-1 to Q-268; M-1 to S-267; M-1 to L-266; M-1 to H-265; M-1 to N-264; M-1 to G-263; M-1 to L-262; M-1 to L-261; M-1 to A-260; M-1 to G-259; M-1 to D-258; M-1 to L-257; M-1 to A-256; M-1 to G-255; M-1 to N-254; M-1 to L-253; M-1 to F-252; M-1 to A-251; M-1 to M-250; M-1 to T-249; M-1 to L-248; M-1 to R-247; M-1 to S-246; M-1 to A-245; M-1 to Q-244; M-1 to P-243; M-1 to D-242; M-1 to L-241; M-1 to L-240; M-1 to T-239; M-1 to F-238; M-1 to V-237; M-1 to R-236; M-1 to P-235; M-1 to A-234; M-1 to T-233; M-1 to L-232; M-1 to Q-231; M-1 to D-230; M-1 to W-229; M-1 to C-228; M-1 to G-227; M-1 to E-226; M-1 to T-225; M-1 to G-224; M-1 to L-223; M-1 to G-222; M-1 to P-221; M-1 to P-220; M-1 to S-219; M-1 to W-218; M-1 to T-217; M-1 to Q-216; M-1 to S-215; M-1 to R-214; M-1 to H-213; M-1 to L-212; M-1 to F-211; M-1 to T-210; M-1 to L-209; M-1 to G-208; M-1 to L-207; M-1 to D-206; M-1 to G-205; M-1 to A-204; M-1 to L-203; M-1 to T-202; M-1 to I-201; M-1 to A-200; M-1 to L-199; M-1 to L-198; M-1 to R-197; M-1 to D-196; M-1 to V-195; M-1 to T-194; M-1 to T-193; M-1 to P-192; M-1 to T-191; M-1 to K-190; M-1 to A-189; M-1 to K-188; M-1 to D-187; M-1 to N-186; M-1 to P-185; M-1 to L-184; M-1 to T-183; M-1 to A-182; M-1 to G-181; M-1 to V-180; M-1 to D-179; M-1 to P-178; M-1 to S-177; M-1 to S-176; M-1 to A-175; M-1 to N-174; M-1 to P-173; M-1 to F-172; M-1 to A-171; M-1 to D-170; M-1 to M-169; M-1 to L-168; M-1 to G-167; M-1 to P-166; M-1 to W-165; M-1 to T-164; M-1 to A-163; M-1 to R-162; M-1 to I-161; M-1 to N-160; M-1 to A-159; M-1 to L-158; M-1 to T-157; M-1 to D-156; M-1 to G-155; M-1 to T-154; M-1 to D-153; M-1 to C-152; M-1 to P-151; M-1 to I-150; M-1 to A-149; M-1 to L-148; M-1 to C-147; M-1 to D-146; M-1 to S-145; M-1 to P-144; M-1 to L-143; M-1 to N-142; M-1 to A-141; M-1 to V-140; M-1 to S-139; M-1 to H-138; M-1 to A-137; M-1 to Q-136; M-1 to L-135; M-1 to G-134; M-1 to A-133; M-1 to E-132; M-1 to L-131; M-1 to G-130; M-1 to F-129; M-1 to L-128; M-1 to L-127; M-1 to P-126; M-1 to K-125; M-1 to V-124; M-1 to A-123; M-1 to V-122; M-1 to T-121; M-1 to S-120; M-1 to G-119; M-1 to D-118; M-1 to P-117; M-1 to A-116; M-1 to L-115; M-1 to V-114; M-1 to V-113; M-1 to G-112; M-1 to Y-111; M-1 to E-110; M-1 to R-109; M-1 to G-108; M-1 to N-107; M-1 to Q-106; M-1 to V-105; M-1 to D-104; M-1 to H-103; M-1 to Q-102; M-1 to A-101; M-1 to V-100; M-1 to E-99; M-1 to S-98; M-1 to I-97; M-1 to L-96; M-1 to A-95; M-1 to Q-94; M-1 to L-93; M-1 to E-92; M-1 to P-91; M-1 to S-90; M-1 to L-89; M-1 to S-88; M-1 to H-87; M-1 to P-86; M-1 to D-85; M-1 to P-84; M-1 to E-83; M-1 to T-82; M-1 to T-81; M-1 to N-80; M-1 to H-79; M-1 to S-78; M-1 to P-77; M-1 to A-76; M-1 to K-75; M-1 to L-74; M-1 to L-73; M-1 to L-72; M-1 to R-71; M-1 to Q-70; M-1 to H-69; M-1 to L-68; M-1 to S-67; M-1 to N-66; M-1 to H-65; M-1 to T-64; M-1 to S-63; M-1 to S-62; M-1 to N-61; M-1 to K-60; M-1 to A-59; M-1 to S-58; M-1 to L-57; M-1 to I-56; M-1 to W-55; M-1 to A-54; M-1 to S-53; M-1 to A-52; M-1 to T-51; M-1 to I-50; M-1 to S-49; M-1 to A-48; M-1 to E-47; M-1 to T-46; M-1 to V-45; M-1 to P-44; M-1 to V-43; M-1 to K-42; M-1 to Q-41; M-1 to E-40; M-1 to L-39; M-1 to E-38; M-1 to A-37; M-1 to L-36; M-1 to A-35; M-1 to Q-34; M-1 to I-33; M-1 to I-32; M-1 to S-31; M-1 to D-30; M-1 to M-29; M-1 to L-28; M-1 to L-27; M-1 to P-26; M-1 to L-25; M-1 to S-24; M-1 to S-23; M-1 to A-22; M-1 to A-21; M-1 to G-20; M-1 to P-19; M-1 to E-18; M-1 to P-17; M-1 to W-16; M-1 to L-15; M-1 to L-14; M-1 to L-13; M-1 to G-12; M-1 to L-11; M-1 to V-10; M-1 to I-9; M-1 to W-8; M-1 to L-7; of FIGS. 2A–C (SEQ ID NO:4). Polypeptides encoded by these polynucleotides are also encompassed by the invention.

The present application is also directed to proteins containing polypeptides at least 80%, 85%, 90%, 95%, 96%, 97%, 98% or 99% identical to the mPGRP-L polypeptide sequence set forth herein as 1-n. In preferred embodiments, the application is directed to proteins containing polypeptides at least 80%, 85%, 90%, 95%, 96%, 97%, 98% or 99% identical to polypeptides having the amino acid sequence of the specific mPGRP-L C-terminal deletions recited herein. Polynucleotides encoding these polypeptides are also encompassed by the invention.

Among the especially preferred fragments of the invention are fragments characterized by structural or functional attributes of PGRP-L. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of PGRP-L, FIGS. 1A–B (SEQ ID NO:2), and FIGS. 2A–C (SEQ ID NO:4). Certain preferred regions are those set out in FIG. 4 and/or 5 and include, but are not limited to, regions of the aforementioned types identified by analysis of the amino acid sequence depicted in FIGS. 1A–B (SEQ ID NO:2), and FIGS. 2A–C (SEQ ID NO:4), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic regions; Hopp-Woods predicted hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of PGRP-L. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of PGRP-L.

The data representing the structural or functional attributes of PGRP-L set forth in FIG. 4 and/or 5 (Tables I and II, respectively), as described above, was generated using the various modules and algorithms of the DNA*STAR set on default parameters. In a preferred embodiment, the data presented in columns VIII, IX, XIII, and XIV of Tables I and/or II can be used to determine regions of PGRP-L which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIGS. 4 and 5, but may, as shown in Tables I and II, be represented or identified by using tabular representations of the data. The DNA*STAR computer algorithm used to generate FIGS. 4 and 5 was used to present the data in Tables I and II in a tabular format. The tabular format of the data in Tables I and II may be used to easily determine specific boundaries of a preferred region.

The above-mentioned preferred regions set out in Tables I and II include, but are not limited to, regions of the aforementioned types identified by analysis of the amino acid sequence set out in FIGS. 1A–B and FIGS. 2A–C, respectively. As set out in Table I and in Table II, such preferred regions include Garnier-Robson alpha-regions, beta-regions, turn-regions, and coil-regions, Chou-Fasman alpha-regions, beta-regions, and coil-regions, Kyte-Doolittle hydrophilic regions, Hopp-Woods hydrophobic regions, Eisenberg alpha- and beta-amphipathic regions, Karplus-Schulz flexible regions, Emini surface-forming regions and Jameson-Wolf regions of high antigenic index.

TABLE 1

| Res | Position | I | II | III | IV | V | VI | VII | VIII | IX | X | XI | XII | XIII | XIV |
|---|---|---|---|---|---|---|---|---|---|---|---|---|---|---|---|
| Arg | 1 | . | . | . | . | . | T | . | . | 1.10 | 0.13 | * | . | . | 0.45 | 1.04 |
| Gly | 2 | . | . | . | . | B | T | . | . | 0.63 | 0.61 | * | . | . | -0.20 | 0.85 |
| Trp | 3 | . | . | . | . | B | T | . | . | 0.68 | 0.83 | * | . | . | -0.20 | 0.50 |
| His | 4 | . | . | . | . | B | . | . | C | 0.48 | 0.83 | * | . | . | -0.40 | 0.25 |
| Trp | 5 | . | . | . | . | B | . | . | C | 0.83 | 1.33 | * | . | . | -0.40 | 0.26 |
| Val | 6 | . | . | . | B | B | . | . | . | 0.41 | 1.40 | * | . | . | -0.60 | 0.33 |
| Gly | 7 | . | . | . | B | B | . | . | . | -0.06 | 0.97 | . | . | . | -0.60 | 0.35 |
| Ala | 8 | . | . | . | B | B | . | . | . | -0.11 | 1.16 | . | . | . | -0.60 | 0.28 |
| His | 9 | . | . | . | . | B | . | . | C | -0.11 | 0.67 | . | . | . | -0.40 | 0.37 |
| Thr | 10 | . | . | . | . | B | . | . | C | 0.18 | 0.53 | . | . | . | -0.40 | 0.51 |
| Leu | 11 | . | . | . | . | B | . | . | C | 0.73 | 0.50 | . | * | . | -0.40 | 0.80 |
| Gly | 12 | . | . | . | . | B | T | . | . | 1.19 | 0.39 | * | * | . | 0.35 | 0.79 |
| His | 13 | . | . | . | . | . | T | . | . | 1.43 | -0.11 | * | . | . | 1.55 | 1.07 |
| Asn | 14 | . | . | . | . | . | T | C | . | 0.77 | -0.17 | * | * | F | 1.95 | 1.29 |
| Ser | 15 | . | . | . | . | . | T | C | . | 0.73 | -0.07 | . | . | F | 2.20 | 1.13 |
| Arg | 16 | . | . | . | . | T | T | . | . | 0.69 | -0.07 | . | . | F | 2.50 | 0.82 |
| Gly | 17 | . | . | . | . | T | T | . | . | 0.44 | 0.07 | . | . | F | 1.65 | 0.38 |
| Phe | 18 | . | . | . | B | B | . | . | . | -0.41 | 0.17 | . | . | . | 0.45 | 0.29 |
| Gly | 19 | . | . | . | B | B | . | . | . | -1.27 | 0.47 | . | . | . | -0.10 | 0.10 |
| Val | 20 | . | . | . | B | B | . | . | . | -1.31 | 1.11 | . | . | . | -0.35 | 0.08 |
| Ala | 21 | . | . | . | B | B | . | . | . | -1.42 | 1.11 | . | . | . | -0.60 | 0.09 |
| Ile | 22 | . | . | . | B | B | . | . | . | -1.32 | 0.73 | . | . | . | -0.60 | 0.14 |
| Val | 23 | . | . | . | B | . | . | T | . | -0.93 | 1.06 | . | * | . | -0.20 | 0.30 |
| Gly | 24 | . | . | . | B | . | . | T | . | -1.18 | 0.90 | . | . | . | -0.20 | 0.43 |
| Asn | 25 | . | . | . | B | . | . | T | . | -0.91 | 0.90 | . | * | . | -0.20 | 0.62 |
| Tyr | 26 | . | . | . | B | . | . | T | . | -1.13 | 0.71 | . | . | . | -0.20 | 0.84 |
| Thr | 27 | . | A | B | . | . | . | . | . | -0.46 | 0.76 | . | . | . | -0.60 | 0.70 |
| Ala | 28 | . | A | B | . | . | . | . | . | 0.09 | 0.76 | . | . | . | -0.60 | 0.67 |
| Ala | 29 | . | A | B | . | . | . | . | . | 0.43 | 0.84 | . | * | . | -0.60 | 0.62 |
| Leu | 30 | . | A | B | . | . | . | . | . | -0.16 | 0.09 | . | . | . | -0.30 | 0.75 |
| Pro | 31 | . | A | B | . | . | . | . | . | -0.50 | 0.10 | . | * | F | -0.15 | 0.75 |
| Thr | 32 | . | A | B | . | . | . | . | . | -1.00 | 0.10 | . | * | F | -0.15 | 0.75 |
| Glu | 33 | A | A | . | . | . | . | . | . | -0.30 | 0.29 | . | * | F | -0.15 | 0.75 |
| Ala | 34 | A | A | . | . | . | . | . | . | -0.02 | -0.40 | * | * | . | 0.30 | 0.94 |
| Ala | 35 | . | A | B | . | . | . | . | . | -0.07 | -0.34 | * | * | . | 0.30 | 0.94 |
| Leu | 36 | . | A | B | . | . | . | . | . | 0.26 | -0.19 | * | . | . | 0.30 | 0.40 |
| Arg | 37 | . | A | B | . | . | . | . | . | 0.57 | -0.19 | * | . | . | 0.30 | 0.78 |
| Thr | 38 | . | A | B | . | . | . | . | . | 0.26 | -0.69 | * | * | F | 0.90 | 1.30 |
| Val | 39 | . | A | B | . | . | . | . | . | 0.03 | -0.70 | * | . | F | 1.11 | 2.27 |
| Arg | 40 | . | A | B | . | . | . | . | . | 0.41 | -0.70 | * | . | F | 1.17 | 0.96 |
| Asp | 41 | . | A | . | . | T | . | . | . | 0.92 | -0.27 | * | . | F | 1.63 | 1.02 |
| Thr | 42 | . | . | B | . | . | . | . | . | 0.14 | -0.37 | * | . | F | 1.64 | 1.85 |
| Leu | 43 | . | . | . | . | . | T | C | . | -0.13 | -0.44 | . | * | F | 2.10 | 0.51 |
| Pro | 44 | . | . | B | . | . | T | . | . | -0.13 | 0.06 | . | * | F | 1.09 | 0.31 |
| Ser | 45 | . | . | B | . | . | T | . | . | -0.13 | 0.70 | . | * | . | 0.43 | 0.16 |
| Cys | 46 | . | . | B | . | . | T | . | . | -0.72 | 0.21 | * | * | . | 0.52 | 0.37 |
| Ala | 47 | . | . | B | . | . | . | . | . | -0.76 | 0.03 | * | * | . | 0.11 | 0.24 |
| Val | 48 | . | . | B | . | . | . | . | . | -0.76 | 0.03 | . | * | . | -0.10 | 0.18 |
| Arg | 49 | . | A | B | . | . | . | . | . | -1.36 | 0.33 | . | * | . | -0.30 | 0.28 |
| Ala | 50 | . | A | B | . | . | . | . | . | -0.94 | 0.44 | . | * | . | -0.60 | 0.23 |
| Gly | 51 | . | A | B | . | . | . | . | . | -0.49 | -0.06 | . | * | . | 0.30 | 0.60 |
| Leu | 52 | . | A | B | . | . | . | . | . | 0.10 | -0.27 | . | * | . | 0.46 | 0.47 |
| Leu | 53 | . | A | B | . | . | . | . | . | 0.71 | -0.27 | . | * | . | 0.62 | 0.78 |
| Arg | 54 | . | . | B | . | . | T | . | . | 0.01 | -0.01 | . | * | F | 1.48 | 1.24 |
| Pro | 55 | . | . | B | . | . | T | . | . | -0.21 | 0.06 | . | * | F | 1.04 | 1.51 |
| Asp | 56 | . | . | . | . | T | T | . | . | -0.68 | 0.06 | . | * | F | 1.60 | 1.51 |
| Tyr | 57 | . | . | B | . | . | T | . | . | -0.21 | 0.06 | . | * | . | 0.74 | 0.64 |
| Ala | 58 | . | A | B | . | . | . | . | . | 0.57 | 0.49 | . | * | . | -0.12 | 0.41 |
| Leu | 59 | . | A | B | . | . | . | . | . | 0.57 | 0.56 | . | * | . | -0.28 | 0.33 |
| Leu | 60 | . | A | B | . | . | . | . | . | 0.78 | 0.56 | * | . | . | -0.44 | 0.42 |
| Gly | 61 | . | A | B | . | . | . | . | . | -0.03 | 0.20 | * | . | . | -0.30 | 0.71 |
| His | 62 | . | A | B | . | . | . | . | . | -0.64 | 0.39 | * | * | . | -0.30 | 0.71 |
| Arg | 63 | . | A | B | . | . | . | . | . | 0.06 | 0.34 | * | * | . | -0.30 | 0.64 |
| Gln | 64 | . | A | B | . | . | . | . | . | 0.56 | -0.34 | * | * | . | 0.45 | 1.27 |
| Leu | 65 | . | A | B | . | . | . | . | . | 1.37 | -0.29 | * | * | . | 0.45 | 1.35 |
| Val | 66 | . | A | B | . | . | . | . | . | 1.04 | -0.79 | * | * | . | 0.75 | 1.15 |
| Arg | 67 | . | A | B | . | . | . | . | . | 0.87 | -0.21 | * | * | F | 0.76 | 0.36 |
| Thr | 68 | . | . | B | . | . | . | . | . | 0.41 | -0.19 | * | * | F | 1.27 | 0.67 |
| Asp | 69 | . | . | . | . | . | T | . | . | 0.41 | -0.44 | . | * | F | 1.98 | 0.89 |
| Cys | 70 | . | . | B | . | . | T | . | . | 0.63 | -1.09 | . | * | F | 2.39 | 0.76 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 71 | . | . | . | . | T | T | . | 0.68 | −0.59 | . | * | F | 3.10 | 0.53 |
| Gly | 72 | . | . | . | . | T | T | . | −0.13 | −0.39 | * | * | F | 2.49 | 0.26 |
| Asp | 73 | . | . | B | . | . | T | . | 0.18 | 0.40 | * | * | F | 1.18 | 0.42 |
| Ala | 74 | . | A | B | . | . | . | . | −0.63 | −0.17 | * | * | . | 0.92 | 0.46 |
| Leu | 75 | . | A | B | . | . | . | . | −0.78 | 0.09 | * | * | . | 0.01 | 0.38 |
| Phe | 76 | . | A | B | . | . | . | . | −0.46 | 0.34 | * | . | . | −0.30 | 0.19 |
| Asp | 77 | . | A | B | . | . | . | . | −0.42 | 0.34 | * | . | . | −0.30 | 0.36 |
| Leu | 78 | . | A | B | . | . | . | . | −0.71 | 0.33 | * | . | . | −0.30 | 0.64 |
| Leu | 79 | . | A | B | . | . | . | . | −0.33 | 0.56 | * | . | . | −0.60 | 0.77 |
| Arg | 80 | . | A | . | . | . | T | . | 0.44 | 0.20 | * | . | . | 0.10 | 0.72 |
| Thr | 81 | . | . | . | . | . | T | . | 0.44 | 0.70 | * | * | . | 0.15 | 1.18 |
| Trp | 82 | . | . | . | . | . | T | C | 0.13 | 0.80 | * | * | . | 0.15 | 1.24 |
| Pro | 83 | . | . | . | . | . | T | C | 0.36 | 0.60 | * | * | . | 0.00 | 0.91 |
| His | 84 | . | . | . | . | T | T | . | 0.31 | 1.10 | * | * | . | 0.20 | 0.64 |
| Phe | 85 | . | . | B | . | . | T | . | −0.10 | 1.26 | * | * | . | −0.20 | 0.45 |
| Thr | 86 | . | . | B | B | . | . | . | −0.60 | 0.73 | * | * | . | −0.60 | 0.39 |
| Ala | 87 | . | . | B | B | . | . | . | −0.20 | 0.99 | * | * | . | −0.60 | 0.24 |
| Val | 88 | . | . | B | B | . | . | . | −0.29 | 0.49 | * | . | . | −0.60 | 0.54 |
| Ser | 89 | . | . | B | B | . | . | . | −1.07 | 0.09 | * | . | . | −0.30 | 0.50 |
| Leu | 90 | . | . | B | B | . | . | . | −0.40 | 0.29 | . | . | . | −0.30 | 0.41 |
| Arg | 91 | . | . | B | B | . | . | . | −0.33 | 0.29 | . | * | . | −0.30 | 0.75 |
| Ser | 92 | . | . | B | B | . | . | . | −0.06 | 0.40 | * | * | . | −0.30 | 0.87 |
| Leu | 93 | . | . | B | B | . | . | . | 0.21 | 0.50 | * | . | . | −0.45 | 1.53 |
| His | 94 | . | . | B | B | . | . | . | 0.62 | 0.31 | * | . | . | −0.30 | 0.79 |
| Tyr | 95 | . | . | B | B | . | . | . | 1.54 | 0.31 | * | . | . | −0.15 | 1.15 |
| Thr | 96 | . | . | B | B | . | . | . | 1.22 | −0.07 | * | . | . | 0.45 | 2.73 |
| Ala | 97 | . | . | B | B | . | . | . | 1.22 | −0.33 | * | * | . | 0.73 | 3.11 |
| Arg | 98 | . | . | B | B | . | . | . | 1.18 | −0.44 | * | * | F | 1.16 | 2.66 |
| Arg | 99 | . | . | B | . | . | T | . | 0.97 | −0.56 | . | . | F | 2.14 | 1.37 |
| Pro | 100 | . | . | B | . | . | T | . | 0.90 | −0.29 | . | . | F | 2.12 | 2.12 |
| Ser | 101 | . | . | B | . | T | T | . | 0.91 | −0.30 | . | . | F | 2.80 | 1.56 |
| Val | 102 | . | . | B | . | . | T | . | 1.20 | 0.09 | . | . | F | 1.52 | 1.07 |
| Tyr | 103 | . | . | B | . | . | . | . | 0.78 | 0.47 | . | . | F | 0.87 | 0.93 |
| Thr | 104 | . | . | B | . | . | T | . | 0.78 | 0.53 | * | . | F | 1.07 | 1.00 |
| Ser | 105 | . | . | B | . | . | . | . | 0.78 | 0.14 | * | . | F | 1.52 | 2.63 |
| Ser | 106 | . | . | B | . | T | T | . | 0.27 | −0.07 | * | . | F | 2.52 | 2.60 |
| Thr | 107 | . | . | . | . | T | T | . | 0.91 | −0.14 | * | . | F | 2.80 | 1.48 |
| Arg | 108 | . | . | B | . | . | . | . | 0.94 | −0.20 | * | . | F | 1.92 | 1.71 |
| Pro | 109 | . | . | . | . | T | . | . | 0.67 | −0.16 | * | . | F | 2.04 | 1.98 |
| Leu | 110 | . | . | . | . | . | . | C | 0.30 | −0.04 | * | . | F | 1.56 | 1.38 |
| Pro | 111 | . | . | B | . | . | . | . | 0.60 | 0.04 | * | . | F | 0.33 | 0.38 |
| Pro | 112 | . | . | . | . | T | . | . | 0.61 | 0.44 | * | . | F | 0.15 | 0.39 |
| Ala | 113 | . | . | . | . | T | . | . | −0.17 | 0.40 | * | . | . | 0.30 | 0.64 |
| Cys | 114 | . | . | B | . | . | T | . | −0.54 | 0.29 | * | * | . | 0.10 | 0.22 |
| Asn | 115 | . | . | B | . | . | T | . | 0.38 | 0.36 | * | * | . | 0.10 | 0.14 |
| Ser | 116 | . | . | B | . | . | T | . | 0.28 | −0.07 | * | * | . | 0.70 | 0.28 |
| Cys | 117 | . | . | B | . | . | T | . | −0.10 | −0.09 | * | . | . | 0.70 | 0.76 |
| Ala | 118 | . | . | B | . | . | . | . | 0.19 | −0.16 | * | . | . | 0.50 | 0.48 |
| Arg | 119 | . | . | B | . | . | . | . | 0.27 | −0.17 | . | * | . | 0.50 | 0.48 |
| Thr | 120 | . | . | B | . | . | . | . | 0.38 | −0.06 | . | * | F | 0.65 | 0.90 |
| Ala | 121 | . | . | B | . | . | . | . | 0.47 | −0.63 | . | . | F | 1.10 | 1.74 |
| Ser | 122 | . | . | B | . | . | . | . | 0.92 | −0.70 | . | * | F | 1.44 | 1.37 |
| Ala | 123 | . | . | . | . | . | . | C | 1.20 | −0.27 | * | . | F | 1.68 | 1.47 |
| Arg | 124 | . | . | . | . | . | . | C | 0.79 | −0.27 | . | . | F | 2.02 | 2.10 |
| Pro | 125 | . | . | . | . | . | T | C | 1.21 | −0.39 | . | * | F | 2.56 | 2.10 |
| Pro | 126 | . | . | . | . | . | T | . | 1.91 | −0.77 | . | * | F | 3.40 | 4.07 |
| Thr | 127 | . | . | . | . | . | T | T | 2.18 | −1.27 | . | * | F | 3.06 | 4.07 |
| Ser | 128 | . | . | B | . | . | . | T | 1.91 | −0.77 | . | * | F | 2.32 | 3.58 |
| Arg | 129 | . | . | B | B | . | . | . | 1.56 | −0.56 | . | . | F | 1.58 | 1.72 |
| Arg | 130 | . | . | B | B | . | . | . | 1.47 | −0.23 | * | . | F | 0.94 | 1.86 |
| His | 131 | . | . | B | B | . | . | . | 1.33 | −0.33 | * | . | . | 0.45 | 1.86 |
| Val | 132 | . | . | B | B | . | . | . | 1.64 | −0.29 | . | . | . | 0.30 | 0.94 |
| Tyr | 133 | . | . | B | . | . | T | . | 1.13 | 0.11 | . | . | . | 0.10 | 0.77 |
| Ser | 134 | . | . | B | . | . | T | . | 0.68 | 0.80 | . | . | F | −0.05 | 0.47 |
| Gly | 135 | . | . | . | . | T | T | . | 0.36 | 0.73 | . | * | F | 0.35 | 0.63 |
| Asn | 136 | . | . | . | . | T | T | . | −0.20 | 0.51 | . | . | F | 0.35 | 0.62 |
| Leu | 137 | . | . | . | . | . | . | C | −0.04 | 0.26 | . | . | F | 0.25 | 0.47 |
| Gly | 138 | . | . | . | . | . | . | C | −0.39 | 0.66 | . | * | F | −0.05 | 0.41 |
| Pro | 139 | . | . | B | . | . | . | . | −0.43 | 0.73 | . | . | F | −0.25 | 0.26 |
| Ala | 140 | . | . | B | . | . | . | . | −0.12 | 0.76 | . | . | . | −0.40 | 0.31 |
| Phe | 141 | . | . | B | . | . | . | . | −0.42 | 0.57 | . | . | . | −0.40 | 0.42 |
| Ala | 142 | . | . | B | . | . | . | . | −0.20 | 0.53 | . | . | . | −0.40 | 0.37 |
| Gly | 143 | . | . | B | . | . | . | . | −0.20 | 0.60 | . | . | . | −0.40 | 0.37 |
| His | 144 | . | . | B | . | . | . | . | 0.01 | 0.53 | . | . | . | −0.40 | 0.42 |
| Ser | 145 | . | . | . | . | T | . | C | −0.29 | 0.14 | . | . | . | 0.54 | 0.67 |
| Ala | 146 | . | . | . | . | T | . | C | 0.20 | 0.33 | * | . | . | 0.78 | 0.47 |
| Gly | 147 | . | . | . | . | T | T | . | 0.79 | 0.33 | * | . | F | 1.37 | 0.54 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| Asn | 148 | . | . | . | . | . | T | C | 0.92 | −0.17 | * | . | F | 2.01 | 0.67 |
| Ile | 149 | . | . | . | . | . | T | C | 0.10 | −0.13 | * | . | F | 2.40 | 1.02 |
| Pro | 150 | . | . | B | . | . | T | . | 0.09 | 0.01 | * | . | F | 1.21 | 0.77 |
| Asp | 151 | . | . | B | . | . | T | . | 0.38 | 0.07 | * | . | F | 0.97 | 0.69 |
| Pro | 152 | . | . | B | . | . | T | . | 0.13 | 0.06 | * | . | F | 0.88 | 1.31 |
| Val | 153 | . | . | B | . | . | . | . | −0.11 | −0.13 | * | . | F | 0.89 | 0.86 |
| Thr | 154 | . | . | B | . | . | . | . | 0.19 | 0.20 | * | . | F | 0.05 | 0.81 |
| Ser | 155 | . | . | B | . | . | . | . | −0.19 | 0.70 | . | . | . | −0.40 | 0.53 |
| Ala | 156 | . | . | B | . | . | . | . | −0.49 | 0.77 | . | . | . | −0.40 | 0.72 |
| Tyr | 157 | . | . | B | . | . | . | . | −0.87 | 0.51 | . | . | . | −0.40 | 0.67 |
| Ala | 158 | . | . | B | . | . | . | . | −0.01 | 0.53 | . | . | . | −0.40 | 0.50 |
| Ala | 159 | . | . | B | . | . | . | . | 0.09 | 0.54 | . | . | . | −0.40 | 0.86 |
| Ser | 160 | . | . | . | . | . | . | C | 0.39 | 0.47 | . | . | . | −0.08 | 0.85 |
| Ala | 161 | . | . | B | . | . | . | . | 0.67 | 0.11 | . | * | F | 0.44 | 1.45 |
| Gln | 162 | . | . | B | . | . | . | . | 0.91 | 0.10 | . | * | F | 0.56 | 2.08 |
| Pro | 163 | . | . | . | . | T | . | . | 1.29 | −0.00 | . | * | F | 1.68 | 2.68 |
| Gln | 164 | . | . | . | . | T | . | . | 1.29 | 0.04 | . | * | F | 1.20 | 4.11 |
| Thr | 165 | . | . | B | . | . | . | . | 0.92 | 0.04 | . | * | F | 0.68 | 2.40 |
| Gln | 166 | . | . | B | . | . | T | . | 1.30 | 0.21 | . | * | F | 0.61 | 0.83 |
| Pro | 167 | . | . | B | . | . | T | . | 0.60 | 0.21 | . | * | F | 0.49 | 0.74 |
| Ala | 168 | . | . | B | . | . | T | . | 0.60 | 0.60 | . | . | . | −0.08 | 0.45 |
| Cys | 169 | . | . | B | . | . | T | . | 0.30 | 0.54 | . | . | . | −0.20 | 0.40 |
| Pro | 170 | . | . | B | . | . | . | . | 0.31 | 0.53 | . | . | . | −0.40 | 0.34 |
| Phe | 171 | . | . | B | . | . | T | . | −0.08 | 0.49 | . | . | . | −0.20 | 0.46 |
| Pro | 172 | . | . | . | . | T | T | . | −0.26 | 0.41 | . | . | . | 0.35 | 1.09 |
| Ser | 173 | . | . | . | . | T | T | . | −0.06 | 0.27 | . | . | . | 0.50 | 0.90 |
| Ser | 174 | . | . | . | . | . | T | C | 0.22 | 0.27 | . | . | . | 0.45 | 1.33 |

TABLE II

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | 0.17 | 0.31 | . | . | . | −0.10 | 0.79 |
| Lys | 2 | A | . | . | . | . | . | . | −0.03 | 0.31 | . | . | . | −0.10 | 0.61 |
| Ala | 3 | A | . | . | . | . | . | . | −0.46 | 0.39 | * | . | . | −0.10 | 0.48 |
| Trp | 4 | A | . | . | B | . | . | . | −0.36 | 0.64 | . | * | . | −0.60 | 0.40 |
| Gly | 5 | A | . | . | B | . | . | . | −0.86 | 0.94 | . | . | . | −0.60 | 0.21 |
| Ala | 6 | A | . | . | B | . | . | . | −1.11 | 1.63 | . | * | . | −0.60 | 0.15 |
| Leu | 7 | A | . | . | B | . | . | . | −1.97 | 1.77 | . | . | . | −0.60 | 0.10 |
| Trp | 8 | . | . | B | B | . | . | . | −1.72 | 1.54 | . | . | . | −0.60 | 0.09 |
| Ile | 9 | . | . | B | B | . | . | . | −2.24 | 1.54 | . | . | . | −0.60 | 0.08 |
| Val | 10 | . | . | B | B | . | . | . | −2.71 | 1.73 | . | . | . | −0.60 | 0.08 |
| Leu | 11 | . | . | B | B | . | . | . | −2.93 | 1.73 | . | . | . | −0.60 | 0.07 |
| Gly | 12 | . | . | B | B | . | . | . | −2.41 | 1.50 | . | . | . | −0.60 | 0.08 |
| Leu | 13 | . | . | B | B | . | . | . | −2.33 | 1.73 | . | . | . | −0.60 | 0.11 |
| Leu | 14 | . | . | . | B | . | . | C | −1.44 | 1.51 | . | . | . | −0.40 | 0.21 |
| Leu | 15 | . | . | . | B | . | . | C | −0.80 | 0.83 | . | . | . | −0.40 | 0.36 |
| Trp | 16 | . | . | B | B | . | . | . | −0.33 | 0.83 | . | . | . | −0.60 | 0.68 |
| Pro | 17 | . | . | B | B | . | . | . | −0.58 | 0.57 | . | . | F | −0.24 | 0.81 |
| Glu | 18 | . | . | . | . | . | T | C | −0.36 | 0.39 | . | . | F | 0.87 | 1.00 |
| Pro | 19 | . | . | . | . | . | T | C | 0.16 | 0.20 | . | . | F | 1.08 | 0.96 |
| Gly | 20 | . | . | . | . | T | T | . | 0.67 | −0.33 | . | . | F | 2.09 | 0.83 |
| Ala | 21 | . | . | . | . | . | T | C | 0.14 | −0.37 | . | . | F | 2.10 | 0.64 |
| Ala | 22 | A | . | . | . | . | . | . | 0.14 | 0.31 | . | . | . | 0.74 | 0.34 |
| Ser | 23 | A | . | . | . | . | . | . | −0.67 | 0.31 | . | . | . | 0.53 | 0.54 |
| Ser | 24 | . | . | B | . | . | . | . | −1.27 | 0.57 | . | . | . | 0.02 | 0.44 |
| Leu | 25 | . | A | B | . | . | . | . | −1.52 | 0.76 | . | . | . | −0.39 | 0.36 |
| Pro | 26 | A | A | . | . | . | . | . | −0.93 | 0.87 | * | . | . | −0.60 | 0.26 |
| Leu | 27 | A | A | . | . | . | . | . | −0.64 | 0.49 | * | . | . | −0.60 | 0.33 |
| Leu | 28 | A | A | . | . | . | . | . | −1.23 | 0.49 | * | . | . | −0.60 | 0.53 |
| Met | 29 | A | A | . | . | . | . | . | −1.82 | 0.49 | * | . | . | −0.60 | 0.24 |
| Asp | 30 | A | A | . | . | . | . | . | −1.01 | 0.74 | * | * | . | −0.60 | 0.21 |
| Ser | 31 | A | A | . | . | . | . | . | −1.39 | 0.46 | * | . | . | −0.60 | 0.43 |
| Ile | 32 | A | A | . | . | . | . | . | −1.39 | 0.27 | * | . | . | −0.30 | 0.44 |
| Ile | 33 | A | A | . | . | . | . | . | −1.17 | 0.34 | * | . | . | −0.30 | 0.22 |
| Gln | 34 | A | A | . | . | . | . | . | −0.57 | 0.84 | * | * | . | −0.60 | 0.16 |
| Ala | 35 | A | A | . | . | . | . | . | −1.38 | 0.46 | * | . | . | −0.60 | 0.41 |
| Leu | 36 | A | A | . | . | . | . | . | −1.08 | 0.46 | * | * | . | −0.60 | 0.48 |
| Ala | 37 | A | A | . | . | . | . | . | −0.19 | −0.23 | * | * | . | 0.30 | 0.48 |
| Glu | 38 | A | A | . | . | . | . | . | 0.74 | −0.23 | * | * | . | 0.30 | 0.82 |
| Leu | 39 | A | A | . | . | . | . | . | −0.11 | −0.73 | * | * | F | 0.75 | 1.98 |
| Glu | 40 | A | A | . | . | . | . | . | 0.27 | −0.77 | * | * | F | 0.90 | 1.46 |
| Gln | 41 | A | A | . | . | . | . | . | 0.22 | −0.84 | * | * | F | 0.90 | 1.30 |
| Lys | 42 | A | A | . | . | . | . | . | 0.50 | −0.20 | . | * | F | 0.60 | 1.17 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 43 | A | A | . | . | . | . | . | 0.50 | −0.40 | . | * | F | 0.45 | 0.98 |
| Pro | 44 | A | A | . | . | . | . | . | 0.72 | −0.40 | . | * | F | 0.45 | 0.98 |
| Val | 45 | A | . | . | B | . | . | . | 0.42 | −0.30 | . | * | F | 0.45 | 0.49 |
| Thr | 46 | A | . | . | B | . | . | . | −0.47 | 0.09 | . | . | F | −0.15 | 0.89 |
| Glu | 47 | A | . | . | B | . | . | . | −0.82 | 0.13 | . | * | F | −0.15 | 0.40 |
| Ala | 48 | A | . | . | B | . | . | . | −0.56 | 0.19 | . | * | F | −0.15 | 0.78 |
| Ser | 49 | A | . | . | B | . | . | . | −0.64 | 0.04 | . | * | . | −0.30 | 0.55 |
| Ile | 50 | A | . | . | B | . | . | . | −0.38 | −0.06 | . | * | . | 0.30 | 0.43 |
| Thr | 51 | A | . | . | B | . | . | . | −0.36 | 0.44 | . | * | . | −0.60 | 0.43 |
| Ala | 52 | A | . | . | B | . | . | . | −1.24 | 0.86 | . | * | . | −0.60 | 0.33 |
| Ser | 53 | A | . | . | B | . | . | . | −1.47 | 1.16 | . | * | . | −0.60 | 0.33 |
| Ala | 54 | A | . | . | B | . | . | . | −1.47 | 1.16 | . | . | . | −0.60 | 0.19 |
| Trp | 55 | A | . | . | B | . | . | . | −1.17 | 1.06 | . | * | . | −0.60 | 0.25 |
| Ile | 56 | A | . | . | B | . | . | . | −0.81 | 1.06 | . | . | . | −0.60 | 0.19 |
| Leu | 57 | A | . | . | B | . | . | . | −0.22 | 0.67 | . | . | . | −0.36 | 0.38 |
| Ser | 58 | A | . | . | B | . | . | . | −0.22 | 0.57 | . | . | . | −0.12 | 0.58 |
| Ala | 59 | . | . | . | . | . | . | C | 0.07 | 0.04 | . | . | F | 1.12 | 1.10 |
| Lys | 60 | . | . | . | . | . | . | C | 0.04 | −0.26 | . | . | F | 1.96 | 1.79 |
| Asn | 61 | . | . | . | . | . | T | C | 0.90 | −0.46 | . | . | F | 2.40 | 1.93 |
| Ser | 62 | . | . | . | . | . | T | C | 1.71 | −0.34 | . | . | F | 2.16 | 2.60 |
| Ser | 63 | . | . | . | . | . | T | C | 1.71 | −0.44 | . | . | F | 1.92 | 2.09 |
| Thr | 64 | . | . | . | . | . | T | C | 1.49 | −0.06 | . | . | F | 1.68 | 1.74 |
| His | 65 | . | . | . | . | . | T | C | 1.41 | 0.23 | . | . | F | 0.84 | 1.07 |
| Asn | 66 | . | . | . | . | . | T | C | 1.41 | 0.34 | . | * | F | 0.60 | 1.09 |
| Ser | 67 | . | . | B | . | . | T | . | 1.82 | 0.36 | * | * | F | 0.40 | 1.31 |
| Leu | 68 | A | . | . | . | . | T | . | 1.31 | −0.13 | * | * | . | 0.85 | 1.88 |
| His | 69 | A | A | . | . | . | . | . | 0.81 | 0.06 | * | * | . | −0.30 | 0.96 |
| Gln | 70 | A | A | . | . | . | . | . | 0.03 | 0.34 | . | * | . | −0.30 | 0.59 |
| Arg | 71 | A | A | . | . | . | . | . | 0.08 | 0.64 | * | * | . | −0.60 | 0.59 |
| Leu | 72 | . | A | B | . | . | . | . | −0.21 | −0.04 | * | * | . | 0.30 | 0.87 |
| Leu | 73 | . | A | B | . | . | . | . | 0.39 | −0.04 | * | * | . | 0.30 | 0.51 |
| Leu | 74 | . | A | B | . | . | . | . | 0.12 | −0.01 | * | * | . | 0.30 | 0.40 |
| Lys | 75 | . | A | B | . | . | . | . | 0.09 | 0.37 | * | * | F | −0.15 | 0.65 |
| Ala | 76 | . | . | . | . | . | T | C | −0.02 | 0.19 | * | * | F | 0.60 | 1.08 |
| Pro | 77 | . | . | . | . | . | T | C | 0.48 | −0.10 | * | * | F | 1.20 | 2.10 |
| Ser | 78 | . | . | . | . | . | T | C | 0.98 | −0.30 | * | . | F | 1.20 | 1.52 |
| His | 79 | . | . | . | . | . | T | C | 1.79 | 0.19 | . | * | F | 0.60 | 2.17 |
| Asn | 80 | . | . | . | . | . | . | C | 1.53 | −0.31 | . | . | F | 1.00 | 2.42 |
| Thr | 81 | . | . | . | . | . | . | C | 2.12 | −0.31 | . | . | F | 1.30 | 2.80 |
| Thr | 82 | . | . | . | . | . | . | C | 2.12 | −0.70 | . | . | F | 1.90 | 3.43 |
| Glu | 83 | . | . | . | . | . | . | C | 2.39 | −0.77 | . | . | F | 2.20 | 3.30 |
| Pro | 84 | . | . | . | . | . | . | C | 2.12 | −0.67 | . | . | F | 2.50 | 3.11 |
| Asp | 85 | . | . | . | . | . | T | C | 1.31 | −0.77 | . | . | F | 3.00 | 2.89 |
| Pro | 86 | . | . | . | . | . | T | C | 1.32 | −0.57 | . | . | F | 2.70 | 1.38 |
| His | 87 | . | . | . | . | T | T | . | 1.42 | −0.19 | . | . | F | 2.30 | 1.19 |
| Ser | 88 | . | . | . | . | . | T | C | 1.42 | −0.19 | . | * | . | 1.65 | 1.10 |
| Leu | 89 | . | . | . | . | . | . | C | 0.82 | −0.19 | . | * | . | 1.15 | 1.24 |
| Ser | 90 | . | . | . | . | . | T | C | 0.82 | 0.07 | . | * | F | 0.45 | 0.75 |
| Pro | 91 | A | . | . | . | . | T | . | 0.44 | −0.03 | * | * | F | 0.85 | 0.97 |
| Glu | 92 | A | . | . | . | . | T | . | −0.33 | 0.09 | * | * | . | 0.25 | 1.19 |
| Leu | 93 | A | . | . | . | . | T | . | −0.92 | 0.09 | * | * | . | 0.10 | 0.73 |
| Gln | 94 | A | A | . | . | . | . | . | −0.41 | 0.39 | * | * | . | −0.30 | 0.33 |
| Ala | 95 | A | A | . | . | . | . | . | −0.11 | 0.34 | * | * | . | −0.30 | 0.26 |
| Leu | 96 | A | A | . | . | . | . | . | −0.76 | 0.34 | * | * | . | −0.30 | 0.54 |
| Ile | 97 | A | A | . | . | . | . | . | −1.34 | 0.30 | * | * | . | −0.30 | 0.23 |
| Ser | 98 | A | A | . | . | . | . | . | −0.53 | 0.40 | * | . | . | −0.30 | 0.23 |
| Glu | 99 | A | A | . | . | . | . | . | −0.57 | 0.30 | . | . | . | −0.30 | 0.48 |
| Val | 100 | A | A | . | . | . | . | . | 0.02 | 0.11 | . | . | . | −0.30 | 0.94 |
| Ala | 101 | A | A | . | . | . | . | . | −0.02 | −0.57 | * | * | . | 0.75 | 1.17 |
| Gln | 102 | A | A | . | . | . | . | . | 0.87 | −0.31 | * | . | . | 0.60 | 0.50 |
| His | 103 | A | A | . | . | . | . | . | 1.17 | 0.09 | * | . | . | 0.45 | 1.17 |
| Asp | 104 | A | A | . | . | . | . | . | 0.82 | −0.16 | * | . | . | 1.35 | 1.86 |
| Val | 105 | . | . | B | . | . | T | . | 1.79 | −0.23 | * | . | F | 2.20 | 1.07 |
| Gln | 106 | . | . | . | . | . | T | C | 2.38 | −0.63 | * | . | F | 3.00 | 1.53 |
| Asn | 107 | . | . | . | . | . | T | C | 2.13 | −1.13 | * | . | F | 2.70 | 1.59 |
| Gly | 108 | . | . | . | . | T | T | . | 1.82 | −0.37 | . | . | F | 2.30 | 3.36 |
| Arg | 109 | . | . | . | . | . | T | . | 0.97 | −0.59 | . | . | F | 2.10 | 1.92 |
| Glu | 110 | . | . | B | B | . | . | . | 0.97 | −0.34 | * | . | F | 0.75 | 0.89 |
| Tyr | 111 | . | . | B | B | . | . | . | 0.16 | −0.10 | * | . | . | 0.30 | 0.66 |
| Gly | 112 | . | . | B | B | . | . | . | −0.43 | 0.16 | . | * | . | −0.30 | 0.28 |
| Val | 113 | . | . | B | B | . | . | . | −0.30 | 0.66 | . | . | . | −0.60 | 0.16 |
| Val | 114 | . | . | B | B | . | . | . | −0.41 | 1.09 | . | . | . | −0.60 | 0.16 |
| Leu | 115 | . | . | B | B | . | . | . | −0.76 | 0.33 | . | . | . | −0.05 | 0.27 |
| Ala | 116 | . | . | B | . | . | . | T | −0.81 | 0.33 | . | . | . | 0.60 | 0.36 |
| Pro | 117 | . | . | B | . | . | . | T | −0.78 | 0.07 | . | . | F | 1.00 | 0.65 |
| Asp | 118 | . | . | . | . | T | T | . | −0.78 | −0.09 | . | . | F | 2.40 | 1.14 |
| Gly | 119 | . | . | . | . | T | T | . | −0.51 | −0.13 | . | . | F | 2.50 | 0.84 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 120 | . | . | B | B | . | . | . | −0.56 | −0.13 | * | * | F | 1.45 | 0.55 |
| Thr | 121 | . | . | B | B | . | . | . | 0.08 | 0.09 | * | . | F | 0.60 | 0.24 |
| Val | 122 | . | . | B | B | . | . | . | 0.08 | 0.09 | * | . | . | 0.20 | 0.49 |
| Ala | 123 | . | . | B | B | . | . | . | −0.73 | 0.09 | * | . | . | −0.05 | 0.57 |
| Val | 124 | . | . | B | B | . | . | . | −1.20 | 0.39 | . | . | . | −0.30 | 0.33 |
| Lys | 125 | . | . | B | B | . | . | . | −1.60 | 0.59 | * | . | . | −0.60 | 0.36 |
| Pro | 126 | . | . | B | B | . | . | . | −1.63 | 0.73 | . | . | . | −0.60 | 0.31 |
| Leu | 127 | . | . | B | B | . | . | . | −1.59 | 0.66 | * | * | . | −0.60 | 0.41 |
| Leu | 128 | . | . | B | B | . | . | . | −1.00 | 0.70 | * | . | . | −0.60 | 0.17 |
| Phe | 129 | . | A | . | B | . | . | . | −0.73 | 0.70 | * | . | . | −0.60 | 0.19 |
| Gly | 130 | A | . | . | B | . | . | . | −1.12 | 0.77 | * | * | . | −0.60 | 0.23 |
| Leu | 131 | A | A | . | . | . | . | . | −1.72 | 0.51 | . | * | . | −0.60 | 0.28 |
| Glu | 132 | A | A | . | . | . | . | . | −0.91 | 0.51 | . | . | . | −0.60 | 0.27 |
| Ala | 133 | A | A | . | . | . | . | . | −0.69 | 0.13 | . | * | . | −0.30 | 0.47 |
| Gly | 134 | A | A | . | . | . | . | . | −0.02 | 0.20 | . | * | . | −0.30 | 0.57 |
| Leu | 135 | A | A | . | . | . | . | . | 0.02 | 0.01 | . | * | . | −0.30 | 0.45 |
| Gln | 136 | A | A | . | . | . | . | . | −0.02 | 0.40 | . | * | . | −0.30 | 0.60 |
| Ala | 137 | A | A | . | . | . | . | . | −0.61 | 0.54 | . | * | . | −0.60 | 0.45 |
| His | 138 | A | A | . | . | . | . | . | −0.02 | 0.61 | . | * | . | −0.60 | 0.55 |
| Ser | 139 | . | A | B | . | . | . | . | −0.49 | 0.33 | . | * | . | −0.30 | 0.51 |
| Val | 140 | . | A | B | . | . | . | . | 0.11 | 0.61 | . | * | . | −0.60 | 0.42 |
| Ala | 141 | . | A | B | . | . | . | . | −0.19 | 0.54 | * | * | . | −0.47 | 0.47 |
| Asn | 142 | . | A | B | . | . | . | . | 0.40 | 0.43 | * | . | . | −0.34 | 0.47 |
| Leu | 143 | . | A | . | . | . | . | C | −0.23 | 0.04 | * | . | F | 0.59 | 1.06 |
| Pro | 144 | . | . | . | . | T | T | . | −0.74 | −0.03 | * | . | F | 1.77 | 0.56 |
| Ser | 145 | . | . | . | . | T | T | . | −0.48 | 0.16 | * | . | F | 1.30 | 0.29 |
| Asp | 146 | . | . | . | . | T | T | . | −0.78 | 0.26 | . | . | F | 1.17 | 0.35 |
| Cys | 147 | . | . | B | . | . | T | . | −0.99 | 0.26 | . | . | . | 0.49 | 0.16 |
| Leu | 148 | . | . | B | . | . | . | . | −0.84 | 0.26 | . | . | . | 0.16 | 0.19 |
| Ala | 149 | . | . | B | . | . | . | . | −0.63 | 0.44 | . | . | . | −0.27 | 0.06 |
| Ile | 150 | . | . | B | . | . | . | . | −0.64 | 0.44 | . | . | . | −0.40 | 0.19 |
| Pro | 151 | . | . | B | . | . | . | . | −0.99 | 0.36 | . | . | . | 0.18 | 0.32 |
| Cys | 152 | . | . | B | . | . | . | . | −0.32 | 0.10 | . | . | . | 0.46 | 0.32 |
| Asp | 153 | . | . | . | . | T | T | . | 0.18 | −0.40 | . | . | F | 2.09 | 0.76 |
| Thr | 154 | . | . | B | . | . | T | . | −0.04 | −0.60 | . | . | F | 2.27 | 0.71 |
| Gly | 155 | . | . | . | . | T | T | . | 0.26 | −0.34 | * | . | F | 2.80 | 1.09 |
| Asp | 156 | . | . | . | . | T | T | . | 0.47 | −0.41 | * | . | F | 2.37 | 0.66 |
| Thr | 157 | . | A | B | . | . | . | . | 0.24 | −0.01 | . | * | F | 1.29 | 0.73 |
| Leu | 158 | . | A | B | . | . | . | . | 0.36 | 0.19 | . | * | . | 0.26 | 0.52 |
| Ala | 159 | . | A | B | . | . | . | . | 0.08 | −0.24 | . | * | . | 0.58 | 0.61 |
| Asn | 160 | . | A | B | . | . | . | . | 0.11 | 0.26 | . | * | . | −0.30 | 0.43 |
| Ile | 161 | . | A | B | . | . | . | . | −0.18 | 0.26 | . | * | . | −0.30 | 0.75 |
| Arg | 162 | . | A | B | . | . | . | . | −0.08 | 0.49 | . | * | . | −0.60 | 0.78 |
| Ala | 163 | . | A | B | . | . | . | . | 0.39 | 0.41 | . | * | . | −0.60 | 0.75 |
| Thr | 164 | . | A | B | . | . | . | . | 0.17 | 0.44 | . | * | . | −0.45 | 1.05 |
| Trp | 165 | . | . | . | . | . | T | C | −0.43 | 0.44 | * | * | . | 0.00 | 0.44 |
| Pro | 166 | . | . | B | . | . | T | . | 0.46 | 1.06 | * | * | . | −0.20 | 0.43 |
| Gly | 167 | . | . | . | . | T | T | . | −0.24 | 0.56 | * | . | . | 0.20 | 0.50 |
| Leu | 168 | . | . | B | . | . | T | . | −0.36 | 0.57 | . | . | . | −0.20 | 0.48 |
| Met | 169 | . | . | B | . | . | . | . | −0.26 | 0.44 | * | . | . | −0.40 | 0.27 |
| Asp | 170 | . | . | B | . | . | . | . | 0.03 | 0.44 | * | . | . | −0.40 | 0.42 |
| Ala | 171 | . | . | B | . | . | . | . | −0.34 | 0.41 | * | . | . | −0.40 | 0.82 |
| Phe | 172 | . | . | B | . | . | T | . | −0.30 | 0.23 | * | . | . | 0.10 | 0.84 |
| Pro | 173 | . | . | . | . | . | T | C | 0.21 | −0.00 | * | . | F | 1.05 | 0.68 |
| Asn | 174 | . | . | . | . | T | T | . | 0.60 | 0.39 | . | . | F | 0.65 | 0.90 |
| Ala | 175 | . | . | . | . | . | T | C | 0.60 | 0.31 | . | . | F | 0.85 | 1.60 |
| Ser | 176 | . | . | . | . | . | . | C | 0.33 | −0.47 | . | . | F | 1.50 | 1.73 |
| Ser | 177 | . | . | . | . | . | T | C | 0.69 | −0.26 | . | . | F | 1.80 | 0.80 |
| Pro | 178 | . | . | . | . | . | T | C | 0.31 | −0.23 | . | . | F | 2.05 | 0.78 |
| Asp | 179 | . | . | . | . | T | T | . | 0.00 | −0.23 | . | * | F | 2.50 | 0.59 |
| Val | 180 | . | . | B | . | . | T | . | −0.22 | −0.13 | . | * | F | 1.85 | 0.63 |
| Gly | 181 | . | . | B | . | . | . | . | −0.13 | 0.17 | * | . | . | 0.65 | 0.34 |
| Ala | 182 | . | . | B | . | . | . | . | 0.17 | 0.17 | . | * | . | 0.74 | 0.31 |
| Thr | 183 | . | . | B | . | . | . | . | 0.38 | 0.57 | . | * | . | 0.53 | 0.68 |
| Leu | 184 | . | . | B | . | . | T | . | 0.42 | −0.07 | . | * | F | 2.02 | 1.14 |
| Pro | 185 | A | . | . | . | . | T | . | 0.69 | −0.50 | . | * | F | 2.66 | 2.27 |
| Asn | 186 | . | . | . | . | T | T | . | 1.08 | −0.50 | . | * | F | 3.40 | 1.59 |
| Asp | 187 | . | . | . | . | T | T | . | 1.36 | −0.99 | . | * | F | 3.06 | 3.85 |
| Lys | 188 | . | . | . | . | T | . | . | 1.46 | −1.19 | . | * | F | 2.52 | 3.59 |
| Ala | 189 | . | . | . | . | T | . | . | 1.96 | −1.19 | . | * | F | 2.18 | 3.45 |
| Lys | 190 | . | . | B | B | . | . | . | 1.86 | −1.10 | . | * | F | 1.24 | 2.98 |
| Thr | 191 | . | . | B | B | . | . | . | 1.00 | −0.61 | . | * | F | 0.90 | 2.15 |
| Pro | 192 | . | . | B | B | . | . | . | 1.00 | 0.03 | * | * | F | 0.00 | 1.58 |
| Thr | 193 | . | . | B | B | . | . | . | 1.07 | −0.47 | * | * | F | 0.60 | 1.32 |
| Thr | 194 | . | . | B | B | . | . | . | 0.84 | −0.47 | * | . | F | 0.60 | 1.79 |
| Val | 195 | . | . | B | B | . | . | . | −0.01 | −0.27 | * | . | F | 0.45 | 0.96 |
| Asp | 196 | . | . | B | B | . | . | . | −0.29 | −0.01 | * | . | F | 0.45 | 0.55 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 197 | . | . | B | B | . | . | . | −0.97 | −0.00 | * | . | F | 0.45 | 0.38 |
| Leu | 198 | . | . | B | B | . | . | . | −0.97 | 0.20 | * | . | . | −0.30 | 0.36 |
| Leu | 199 | . | . | B | B | . | . | . | −1.47 | 0.04 | * | . | . | −0.30 | 0.31 |
| Ala | 200 | . | . | B | B | . | . | . | −1.20 | 0.73 | * | . | . | −0.60 | 0.13 |
| Ile | 201 | . | . | B | B | . | . | . | −1.54 | 1.23 | . | . | . | −0.60 | 0.16 |
| Thr | 202 | . | . | B | B | . | . | . | −1.66 | 0.97 | . | * | . | −0.60 | 0.19 |
| Leu | 203 | . | . | B | B | . | . | . | −1.66 | 0.29 | . | * | . | −0.30 | 0.32 |
| Ala | 204 | . | . | B | B | . | . | . | −1.19 | 0.47 | . | * | . | −0.60 | 0.38 |
| Gly | 205 | A | . | . | B | . | . | . | −1.41 | 0.21 | . | * | . | −0.30 | 0.26 |
| Asp | 206 | A | A | . | . | . | . | . | −0.83 | 0.41 | * | * | F | −0.45 | 0.26 |
| Leu | 207 | A | A | . | B | . | . | . | −1.22 | 0.21 | . | * | . | −0.30 | 0.37 |
| Gly | 208 | A | A | . | B | . | . | . | −1.22 | 0.50 | * | * | . | −0.60 | 0.32 |
| Leu | 209 | . | A | B | B | . | . | . | −0.67 | 0.76 | * | * | . | −0.60 | 0.16 |
| Thr | 210 | . | A | B | B | . | . | . | −0.21 | 1.26 | * | * | . | −0.60 | 0.26 |
| Phe | 211 | . | A | B | B | . | . | . | −0.51 | 0.57 | * | * | . | −0.60 | 0.52 |
| Leu | 212 | . | A | B | B | . | . | . | 0.30 | 0.53 | * | * | . | −0.60 | 0.84 |
| His | 213 | . | . | B | . | . | T | . | 0.33 | 0.24 | * | * | . | 0.25 | 1.01 |
| Arg | 214 | . | . | . | . | . | T | T | 0.86 | 0.24 | . | * | F | 0.80 | 1.69 |
| Ser | 215 | . | . | . | . | . | T | T | 0.87 | 0.37 | . | . | F | 0.80 | 2.15 |
| Gln | 216 | . | . | . | . | . | T | T | 1.36 | 0.07 | . | . | F | 0.80 | 2.12 |
| Thr | 217 | . | . | . | . | . | T | . | 1.96 | −0.00 | . | . | F | 1.20 | 1.67 |
| Trp | 218 | . | . | . | . | . | T | . | 1.64 | 0.43 | . | . | F | 0.30 | 1.93 |
| Ser | 219 | . | . | . | . | . | . | C | 0.72 | 0.47 | . | . | F | 0.31 | 1.10 |
| Pro | 220 | . | . | . | . | . | T | C | 0.68 | 0.76 | . | . | F | 0.57 | 0.63 |
| Pro | 221 | . | . | . | . | . | T | T | 0.37 | 0.70 | . | . | F | 0.98 | 0.59 |
| Gly | 222 | . | . | . | . | . | T | T | 0.68 | 0.27 | . | . | F | 1.49 | 0.64 |
| Leu | 223 | . | . | . | . | . | T | C | 0.62 | −0.11 | . | . | F | 2.10 | 0.72 |
| Gly | 224 | . | . | . | . | . | T | C | 0.26 | −0.11 | . | . | F | 1.89 | 0.46 |
| Thr | 225 | . | . | . | . | . | T | C | 0.18 | 0.03 | . | . | F | 1.08 | 0.25 |
| Glu | 226 | . | . | B | . | . | . | T | 0.39 | 0.51 | . | . | F | 0.37 | 0.32 |
| Gly | 227 | . | . | . | . | . | T | T | 0.73 | −0.17 | . | . | F | 1.46 | 0.53 |
| Cys | 228 | . | . | . | . | T | . | . | 0.73 | −0.20 | . | . | . | 0.90 | 0.64 |
| Trp | 229 | . | . | B | . | . | . | . | 0.77 | −0.00 | . | . | . | 0.50 | 0.30 |
| Asp | 230 | . | . | B | . | . | . | . | 0.49 | 0.49 | . | . | . | −0.35 | 0.44 |
| Gln | 231 | . | . | B | . | . | . | . | 0.28 | 0.56 | . | . | . | −0.30 | 0.84 |
| Leu | 232 | . | . | B | . | . | . | . | 0.73 | 0.41 | . | . | F | 0.05 | 1.23 |
| Thr | 233 | . | . | B | . | . | . | . | 0.54 | −0.50 | . | . | F | 1.30 | 1.45 |
| Ala | 234 | . | . | . | . | . | . | C | 0.13 | 0.14 | . | . | F | 0.50 | 0.62 |
| Pro | 235 | . | . | B | B | . | . | . | −0.18 | 0.53 | . | . | F | −0.25 | 0.65 |
| Arg | 236 | . | . | B | B | . | . | . | −0.99 | 0.33 | * | . | . | −0.15 | 0.65 |
| Val | 237 | . | . | B | B | . | . | . | −0.99 | 0.53 | * | . | . | −0.50 | 0.53 |
| Phe | 238 | . | . | B | B | . | . | . | −0.68 | 0.71 | * | . | . | −0.55 | 0.28 |
| Thr | 239 | . | . | B | B | . | . | . | −0.30 | 0.29 | * | * | . | −0.30 | 0.24 |
| Leu | 240 | . | . | B | B | . | . | . | −0.09 | 0.71 | * | * | . | −0.60 | 0.50 |
| Leu | 241 | . | . | B | B | . | . | . | −0.79 | 0.47 | * | * | . | −0.45 | 1.01 |
| Asp | 242 | . | . | . | . | . | T | C | −0.23 | 0.19 | * | . | F | 0.45 | 0.70 |
| Pro | 243 | A | . | . | . | . | T | . | 0.58 | 0.09 | . | . | F | 0.40 | 1.14 |
| Gln | 244 | A | . | . | . | . | T | . | 0.08 | −0.60 | * | . | F | 1.30 | 2.72 |
| Ala | 245 | A | . | . | . | . | T | . | 0.58 | −0.60 | . | . | F | 1.30 | 1.34 |
| Ser | 246 | A | A | . | . | . | . | . | 0.79 | −0.11 | * | * | F | 0.60 | 1.25 |
| Arg | 247 | . | A | B | . | . | . | . | 0.20 | 0.07 | * | * | . | −0.30 | 0.72 |
| Leu | 248 | . | A | B | . | . | . | . | −0.29 | 0.17 | * | . | . | −0.30 | 0.72 |
| Thr | 249 | . | A | B | . | . | . | . | −1.10 | 0.46 | * | . | . | −0.60 | 0.46 |
| Met | 250 | . | A | B | . | . | . | . | −0.51 | 0.76 | * | * | . | −0.60 | 0.19 |
| Ala | 251 | . | A | B | . | . | . | . | −0.56 | 1.16 | * | * | . | −0.60 | 0.38 |
| Phe | 252 | . | A | B | . | . | . | . | −1.26 | 0.90 | * | * | . | −0.60 | 0.26 |
| Leu | 253 | A | A | . | . | . | . | . | −1.26 | 0.91 | . | * | . | −0.60 | 0.27 |
| Asn | 254 | A | A | . | . | . | . | . | −0.94 | 0.99 | . | * | . | −0.60 | 0.22 |
| Gly | 255 | A | A | . | . | . | . | . | −0.69 | 0.49 | * | . | . | −0.60 | 0.42 |
| Ala | 256 | A | A | . | . | . | . | . | −0.69 | 0.13 | * | * | . | −0.30 | 0.50 |
| Leu | 257 | A | A | . | . | . | . | . | −0.80 | −0.06 | . | . | F | 0.45 | 0.32 |
| Asp | 258 | A | A | . | . | . | . | . | −0.80 | 0.23 | . | * | F | −0.15 | 0.26 |
| Gly | 259 | A | A | . | . | . | . | . | −1.14 | 0.49 | * | * | . | −0.60 | 0.21 |
| Ala | 260 | A | A | . | . | . | . | . | −0.80 | 0.41 | . | . | . | −0.60 | 0.26 |
| Leu | 261 | A | A | . | . | . | . | . | −0.24 | 0.13 | . | . | . | −0.30 | 0.25 |
| Leu | 262 | A | A | . | . | . | . | . | −0.24 | 0.63 | . | . | . | −0.60 | 0.34 |
| Gly | 263 | A | A | . | . | . | . | . | −0.54 | 0.89 | . | . | . | −0.60 | 0.28 |
| Asn | 264 | . | . | . | . | T | . | . | −0.20 | 0.77 | * | . | . | 0.00 | 0.45 |
| His | 265 | . | . | . | . | . | . | C | −0.50 | 0.49 | * | . | . | −0.20 | 0.95 |
| Leu | 266 | . | . | B | B | . | . | . | 0.10 | 0.49 | * | . | . | −0.60 | 0.67 |
| Ser | 267 | . | . | . | B | T | . | . | 1.02 | 0.49 | * | . | F | −0.05 | 0.65 |
| Gln | 268 | . | . | B | B | . | . | . | 1.16 | 0.09 | * | . | F | 0.09 | 0.93 |
| Ile | 269 | . | . | B | B | . | . | . | 1.12 | 0.01 | * | . | F | 0.48 | 1.75 |
| Pro | 270 | . | . | B | B | . | . | . | 0.94 | −0.17 | * | . | F | 1.32 | 1.77 |
| Arg | 271 | . | . | . | . | . | T | C | 1.54 | −0.13 | * | * | F | 2.16 | 1.58 |
| Pro | 272 | . | . | . | . | . | T | C | 1.03 | −0.10 | * | * | F | 2.40 | 3.49 |
| His | 273 | . | . | . | . | . | T | C | 0.73 | −0.10 | * | . | F | 2.16 | 1.86 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 274 | . | . | . | . | . | T | C | 1.59 | −0.14 | * | . | F | 1.92 | 1.27 |
| Pro | 275 | . | . | . | . | . | . | C | 0.99 | 0.36 | * | * | F | 0.88 | 1.12 |
| Leu | 276 | . | A | B | . | . | . | . | 0.07 | 0.61 | * | * | . | −0.36 | 0.68 |
| Ser | 277 | . | A | B | . | . | . | . | 0.39 | 0.80 | * | . | . | −0.60 | 0.36 |
| His | 278 | . | A | B | . | . | . | . | 0.42 | 0.37 | * | . | . | −0.30 | 0.46 |
| Leu | 279 | . | A | B | . | . | . | . | 0.39 | −0.06 | * | . | . | 0.30 | 0.96 |
| Leu | 280 | . | A | B | . | . | . | . | 0.36 | 0.01 | * | . | . | −0.15 | 1.13 |
| Arg | 281 | . | A | B | . | . | . | . | 0.82 | 0.39 | * | . | . | −0.15 | 1.30 |
| Glu | 282 | . | A | B | . | . | . | . | 0.53 | 0.31 | * | . | . | −0.15 | 1.56 |
| Tyr | 283 | . | A | B | . | . | . | . | 0.22 | 0.13 | * | . | . | −0.15 | 1.91 |
| Tyr | 284 | . | . | B | . | . | . | . | 0.18 | −0.13 | * | * | . | 0.50 | 0.96 |
| Gly | 285 | . | . | . | . | T | T | . | 0.99 | 0.51 | * | * | . | 0.20 | 0.41 |
| Ala | 286 | . | . | B | . | . | T | . | 0.53 | 0.91 | . | * | . | −0.20 | 0.42 |
| Gly | 287 | . | . | B | . | . | T | . | 0.53 | 0.59 | * | * | . | −0.20 | 0.27 |
| Val | 288 | . | . | . | . | . | T | C | 0.57 | −0.17 | . | . | F | 1.05 | 0.45 |
| Asn | 289 | . | . | B | . | . | T | . | −0.04 | −0.17 | . | * | F | 0.85 | 0.69 |
| Gly | 290 | . | . | B | . | . | T | . | −0.40 | −0.03 | * | * | F | 0.85 | 0.52 |
| Asp | 291 | . | . | B | . | . | T | . | 0.30 | 0.33 | * | * | F | 0.25 | 0.61 |
| Pro | 292 | . | . | B | . | . | T | . | 0.34 | −0.31 | * | * | F | 1.05 | 0.74 |
| Val | 293 | . | . | B | . | . | . | . | 1.20 | −0.33 | . | * | F | 1.05 | 1.00 |
| Phe | 294 | . | . | B | . | . | . | . | 0.50 | −0.36 | * | * | F | 1.25 | 0.96 |
| Arg | 295 | . | . | B | . | . | T | . | 0.96 | 0.43 | * | * | F | 0.75 | 0.54 |
| Ser | 296 | . | . | B | . | . | T | . | 1.07 | −0.00 | * | * | F | 2.00 | 1.42 |
| Asn | 297 | . | . | B | . | . | T | . | 1.28 | −0.64 | * | * | F | 2.10 | 3.21 |
| Phe | 298 | . | . | . | . | T | T | . | 2.13 | −1.03 | * | * | F | 2.60 | 2.84 |
| Arg | 299 | . | . | . | . | T | . | . | 2.49 | −0.63 | * | * | F | 2.50 | 3.41 |
| Arg | 300 | . | . | . | . | T | T | . | 1.79 | −0.59 | * | * | F | 2.80 | 2.10 |
| Gln | 301 | . | . | . | . | T | T | . | 1.50 | −0.49 | * | . | F | 2.60 | 2.45 |
| Asn | 302 | . | . | . | . | . | T | C | 0.69 | −0.77 | * | . | F | 3.00 | 1.26 |
| Gly | 303 | . | . | . | . | . | T | C | 1.08 | −0.09 | * | . | F | 2.25 | 0.53 |
| Ala | 304 | . | . | . | . | . | . | C | 0.67 | 0.40 | . | . | . | 1.00 | 0.44 |
| Ala | 305 | . | . | B | . | . | . | . | −0.03 | 0.39 | . | . | . | 0.50 | 0.37 |
| Leu | 306 | . | . | B | . | . | . | . | −0.24 | 0.49 | . | . | . | −0.10 | 0.38 |
| Thr | 307 | . | . | B | . | . | . | . | −0.56 | 0.49 | . | . | F | −0.25 | 0.58 |
| Ser | 308 | . | . | B | . | . | . | . | −1.02 | 0.47 | . | . | F | −0.25 | 0.82 |
| Ala | 309 | . | A | B | . | . | . | . | −1.02 | 0.66 | * | . | F | −0.45 | 0.82 |
| Pro | 310 | A | A | . | . | . | . | . | −0.43 | 0.47 | * | . | F | −0.45 | 0.58 |
| Thr | 311 | A | A | . | . | . | . | . | 0.38 | 0.39 | * | . | F | −0.15 | 0.75 |
| Leu | 312 | A | A | . | . | . | . | . | −0.17 | 0.40 | * | . | F | 0.00 | 1.28 |
| Ala | 313 | A | A | . | . | . | . | . | −0.16 | 0.54 | * | . | . | −0.60 | 0.61 |
| Gln | 314 | A | A | . | . | . | . | . | 0.43 | 1.03 | * | . | . | −0.60 | 0.45 |
| Gln | 315 | A | A | . | . | . | . | . | 0.06 | 0.54 | * | . | . | −0.60 | 0.94 |
| Val | 316 | A | A | . | . | . | . | . | −0.44 | 0.36 | * | . | . | −0.30 | 0.94 |
| Trp | 317 | A | A | . | . | . | . | . | −0.49 | 0.54 | * | . | . | −0.60 | 0.45 |
| Glu | 318 | A | A | . | . | . | . | . | −0.71 | 0.79 | * | . | . | −0.60 | 0.19 |
| Ala | 319 | A | A | . | . | . | . | . | −1.52 | 1.07 | * | . | . | −0.60 | 0.21 |
| Leu | 320 | A | A | . | . | . | . | . | −1.52 | 1.11 | * | . | . | −0.60 | 0.17 |
| Val | 321 | A | A | . | . | . | . | . | −0.62 | 0.60 | * | . | . | −0.60 | 0.17 |
| Leu | 322 | A | A | . | . | . | . | . | −1.14 | 0.60 | . | * | . | −0.60 | 0.33 |
| Leu | 323 | A | A | . | . | . | . | . | −1.14 | 0.79 | * | . | . | −0.60 | 0.33 |
| Gln | 324 | A | A | . | . | . | . | . | −0.77 | 0.10 | . | * | . | −0.30 | 0.77 |
| Lys | 325 | A | A | . | . | . | . | . | 0.04 | −0.11 | . | * | F | 0.60 | 1.45 |
| Leu | 326 | A | A | . | . | . | . | . | 0.87 | −0.80 | . | . | F | 0.90 | 3.04 |
| Glu | 327 | A | A | . | . | . | . | . | 0.87 | −0.99 | * | . | F | 0.90 | 2.39 |
| Pro | 328 | A | A | . | . | . | . | . | 1.68 | −0.70 | * | . | F | 0.75 | 0.98 |
| Glu | 329 | A | A | . | . | . | . | . | 0.87 | −0.30 | . | * | F | 0.60 | 2.07 |
| His | 330 | A | A | . | . | . | . | . | 0.82 | −0.30 | . | * | . | 0.30 | 0.98 |
| Leu | 331 | A | A | . | . | . | . | . | 1.63 | 0.10 | . | . | . | −0.15 | 1.10 |
| Gln | 332 | A | A | . | . | . | . | . | 0.74 | 0.07 | . | . | . | −0.15 | 1.02 |
| Leu | 333 | A | A | . | . | . | . | . | 0.66 | 0.76 | . | . | . | −0.60 | 0.53 |
| Gln | 334 | A | A | . | . | . | . | . | 0.66 | 0.64 | . | . | . | −0.60 | 0.86 |
| Asn | 335 | . | A | . | . | . | . | C | 0.69 | 0.36 | . | * | F | 0.05 | 0.86 |
| Ile | 336 | . | A | . | . | . | . | C | 1.50 | −0.04 | . | . | F | 0.80 | 1.80 |
| Ser | 337 | . | A | . | . | . | . | C | 0.69 | −0.33 | . | . | F | 0.80 | 1.80 |
| Gln | 338 | A | A | . | . | . | . | . | 0.91 | −0.04 | . | . | F | 0.45 | 0.92 |
| Glu | 339 | A | A | . | . | . | . | . | 0.91 | 0.06 | . | . | F | 0.00 | 1.33 |
| Gln | 340 | A | A | . | . | . | . | . | 0.06 | −0.23 | . | . | F | 0.60 | 1.72 |
| Leu | 341 | A | A | . | . | . | . | . | 0.36 | 0.03 | . | . | . | −0.30 | 0.74 |
| Ala | 342 | A | A | . | . | . | . | . | 0.34 | 0.13 | . | . | . | −0.30 | 0.43 |
| Gln | 343 | A | A | . | . | . | . | . | −0.47 | 0.61 | * | . | . | −0.60 | 0.36 |
| Val | 344 | A | A | . | . | . | . | . | −1.06 | 0.90 | * | . | . | −0.60 | 0.36 |
| Ala | 345 | A | A | . | . | . | . | . | −1.37 | 0.71 | * | . | . | −0.60 | 0.36 |
| Thr | 346 | A | A | . | . | . | . | . | −0.51 | 0.70 | * | . | . | −0.60 | 0.30 |
| Leu | 347 | A | A | . | . | . | . | . | 0.08 | 0.30 | * | . | . | −0.30 | 0.80 |
| Ala | 348 | A | A | . | . | . | . | . | −0.62 | −0.34 | * | . | . | 0.45 | 1.38 |
| Thr | 349 | A | A | . | . | . | . | . | −0.08 | −0.06 | * | . | F | 0.45 | 0.83 |
| Lys | 350 | A | A | . | . | . | . | . | 0.51 | −0.06 | * | . | F | 0.60 | 1.45 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 351 | A | A | . | . | . | . | . | 0.23 | −0.74 | * | . | F | 0.90 | 2.48 |
| Phe | 352 | A | A | . | . | . | . | . | 0.34 | −0.74 | * | . | F | 0.90 | 1.74 |
| Thr | 353 | A | A | . | . | . | . | . | 0.12 | −0.44 | * | . | F | 0.45 | 0.75 |
| Glu | 354 | A | A | . | . | . | . | . | 0.09 | 0.24 | * | . | . | −0.30 | 0.36 |
| Ala | 355 | A | A | . | . | . | . | . | −0.62 | 0.67 | * | . | . | −0.60 | 0.41 |
| Phe | 356 | A | A | . | . | . | . | . | −0.83 | 0.46 | . | . | . | −0.60 | 0.15 |
| Leu | 357 | A | A | . | . | . | . | . | −0.72 | 0.40 | . | . | . | −0.30 | 0.14 |
| Gly | 358 | . | A | . | . | T | . | . | −1.30 | 0.90 | . | . | . | −0.20 | 0.14 |
| Cys | 359 | A | . | . | . | . | . | . | −1.33 | 1.09 | . | . | . | −0.40 | 0.11 |
| Pro | 360 | . | . | . | . | T | . | . | −0.96 | 0.80 | . | * | . | 0.00 | 0.18 |
| Ala | 361 | . | . | . | . | T | . | . | −0.14 | 0.54 | . | * | . | 0.00 | 0.28 |
| Ile | 362 | . | . | B | . | . | . | . | 0.00 | 0.11 | . | * | . | 0.05 | 1.03 |
| His | 363 | . | . | B | . | . | T | . | 0.46 | 0.11 | . | * | . | 0.28 | 0.36 |
| Pro | 364 | . | . | B | . | . | T | . | 0.83 | −0.31 | . | * | . | 1.06 | 0.70 |
| Arg | 365 | . | . | . | . | T | T | . | 0.70 | 0.10 | . | * | . | 1.19 | 1.04 |
| Cys | 366 | . | . | . | . | T | T | . | 0.70 | −0.16 | . | * | . | 1.82 | 0.76 |
| Arg | 367 | . | . | . | . | T | . | . | 1.00 | −0.16 | . | * | . | 1.80 | 0.50 |
| Trp | 368 | . | . | . | . | T | . | . | 0.82 | −0.09 | . | * | . | 1.62 | 0.26 |
| Gly | 369 | . | . | . | . | T | . | . | 0.79 | 0.34 | . | * | . | 0.84 | 0.74 |
| Ala | 370 | . | . | . | . | . | . | C | 0.79 | 0.53 | . | * | . | 0.16 | 0.59 |
| Ala | 371 | . | . | B | . | . | T | . | 1.11 | 0.53 | * | * | . | 0.13 | 1.10 |
| Pro | 372 | . | . | . | . | T | T | . | 0.97 | 0.04 | * | * | . | 0.65 | 1.10 |
| Tyr | 373 | . | . | . | . | T | T | . | 1.04 | 0.11 | . | * | . | 0.65 | 1.48 |
| Arg | 374 | . | . | . | . | T | T | . | 1.08 | 0.04 | . | * | . | 0.85 | 2.27 |
| Gly | 375 | . | . | . | . | . | T | . | 1.46 | 0.03 | . | * | F | 1.00 | 2.11 |
| His | 376 | . | . | . | . | . | T | C | 1.23 | 0.03 | * | * | F | 1.20 | 2.09 |
| Pro | 377 | . | . | . | . | . | T | C | 1.56 | −0.04 | * | * | F | 1.85 | 0.88 |
| Thr | 378 | . | . | B | . | . | T | . | 0.99 | −0.04 | * | * | F | 2.00 | 1.74 |
| Pro | 379 | . | . | B | . | . | T | . | 0.67 | 0.21 | * | * | F | 1.20 | 1.05 |
| Leu | 380 | . | . | B | . | . | . | . | 0.20 | 0.14 | * | * | . | 0.65 | 1.05 |
| Arg | 381 | . | . | B | . | . | . | . | −0.11 | 0.40 | . | * | . | 0.30 | 0.60 |
| Leu | 382 | . | . | B | . | . | T | . | −0.60 | 0.34 | * | * | . | 0.30 | 0.39 |
| Pro | 383 | . | . | B | . | . | T | . | −1.10 | 0.70 | * | * | . | −0.20 | 0.40 |
| Leu | 384 | . | . | B | . | . | T | . | −1.13 | 0.70 | * | * | . | −0.20 | 0.17 |
| Gly | 385 | . | . | B | . | . | T | . | −1.18 | 1.46 | * | * | . | −0.20 | 0.32 |
| Phe | 386 | . | . | B | B | . | . | . | −1.32 | 1.41 | * | * | . | −0.60 | 0.16 |
| Leu | 387 | . | . | B | B | . | . | . | −0.54 | 1.49 | . | . | . | −0.60 | 0.26 |
| Tyr | 388 | . | . | B | B | . | . | . | −0.64 | 1.30 | . | . | . | −0.60 | 0.35 |
| Val | 389 | . | . | B | B | . | . | . | −0.08 | 1.36 | . | . | . | −0.60 | 0.59 |
| His | 390 | . | . | B | B | . | . | . | −0.59 | 1.33 | . | . | . | −0.45 | 1.12 |
| His | 391 | . | . | B | B | . | . | . | −0.10 | 1.29 | . | . | . | −0.60 | 0.53 |
| Thr | 392 | . | . | . | B | T | . | . | 0.12 | 0.96 | . | . | . | −0.05 | 1.10 |
| Tyr | 393 | . | . | B | B | . | . | . | 0.16 | 0.81 | . | . | . | −0.60 | 0.82 |
| Val | 394 | . | . | B | B | . | . | . | 0.80 | 0.74 | . | . | . | −0.60 | 0.93 |
| Pro | 395 | . | . | . | B | T | . | . | 0.17 | 0.67 | . | . | . | −0.20 | 1.00 |
| Ala | 396 | . | . | . | . | . | . | C | −0.11 | 0.76 | . | . | F | −0.05 | 0.34 |
| Pro | 397 | . | . | . | . | . | T | C | −0.11 | 0.49 | . | . | F | 0.15 | 0.66 |
| Pro | 398 | . | . | . | . | T | T | . | −0.57 | 0.33 | . | . | F | 0.65 | 0.62 |
| Cys | 399 | . | . | . | . | T | T | . | 0.29 | 0.69 | . | . | F | 0.35 | 0.53 |
| Thr | 400 | . | . | B | . | . | T | . | 0.20 | 0.59 | . | . | F | −0.05 | 0.59 |
| Thr | 401 | . | . | B | B | . | . | . | 0.12 | 0.54 | . | . | F | −0.45 | 0.51 |
| Phe | 402 | . | . | B | B | . | . | . | −0.26 | 0.69 | . | . | . | −0.60 | 0.51 |
| Gln | 403 | . | . | B | B | . | . | . | −0.63 | 0.61 | . | . | . | −0.60 | 0.36 |
| Ser | 404 | . | . | B | B | . | . | . | 0.03 | 0.63 | * | . | . | −0.60 | 0.25 |
| Cys | 405 | A | . | . | . | . | . | . | −0.26 | 0.14 | * | * | . | −0.10 | 0.49 |
| Ala | 406 | A | . | . | . | . | . | . | 0.17 | −0.03 | * | * | . | 0.50 | 0.28 |
| Ala | 407 | A | . | . | . | . | . | . | 0.57 | −0.43 | * | * | . | 0.50 | 0.41 |
| Asp | 408 | A | . | . | . | . | T | . | −0.03 | −0.43 | * | . | . | 0.85 | 1.01 |
| Met | 409 | A | . | . | . | . | T | . | 0.27 | −0.39 | * | * | . | 0.70 | 0.99 |
| Arg | 410 | A | . | . | . | . | T | . | 1.04 | −0.49 | * | * | . | 0.85 | 1.70 |
| Ser | 411 | A | . | . | . | . | T | . | 0.93 | −0.99 | * | * | F | 1.30 | 2.00 |
| Met | 412 | A | A | . | . | . | . | . | 1.49 | −0.20 | * | * | . | 0.45 | 1.75 |
| Gln | 413 | A | A | . | . | . | . | . | 1.49 | −0.31 | * | * | . | 0.45 | 1.22 |
| Arg | 414 | A | A | . | . | . | . | . | 2.09 | 0.09 | * | * | . | −0.15 | 1.57 |
| Phe | 415 | A | A | . | . | . | . | . | 1.12 | −0.30 | * | * | . | 0.45 | 2.65 |
| His | 416 | A | A | . | . | . | . | . | 1.53 | −0.27 | * | * | . | 0.45 | 1.14 |
| Gln | 417 | . | A | B | . | . | . | . | 2.18 | −0.67 | * | * | F | 0.90 | 1.14 |
| Asp | 418 | . | A | . | . | . | T | . | 1.89 | −0.67 | * | * | F | 1.30 | 2.62 |
| Val | 419 | . | A | . | . | . | T | . | 1.78 | −0.54 | * | * | F | 1.30 | 2.03 |
| Arg | 420 | . | A | . | . | . | T | . | 2.48 | −1.04 | * | * | F | 1.30 | 1.95 |
| Lys | 421 | . | A | . | . | . | T | . | 1.62 | −1.44 | * | . | F | 1.30 | 1.95 |
| Trp | 422 | . | A | . | . | . | T | . | 1.28 | −0.76 | * | . | F | 1.30 | 1.85 |
| Asp | 423 | . | A | B | . | . | . | . | 1.03 | −0.97 | * | * | F | 0.75 | 0.93 |
| Asp | 424 | . | . | . | . | T | T | . | 1.59 | −0.21 | * | . | F | 1.25 | 0.73 |
| Ile | 425 | . | . | B | . | . | T | . | 0.78 | 0.17 | * | . | . | 0.10 | 0.93 |
| Gly | 426 | . | . | B | . | . | T | . | −0.12 | 0.04 | * | . | . | 0.10 | 0.48 |
| Tyr | 427 | . | . | B | . | . | T | . | −0.69 | 0.69 | * | . | . | −0.20 | 0.21 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 428 | . | . | B | B | . | . | . | −1.03 | 1.33 | . | . | . | −0.55 | 0.23 |
| Phe | 429 | . | . | B | B | . | . | . | −1.33 | 1.07 | . | * | . | −0.50 | 0.23 |
| Val | 430 | . | . | B | B | . | . | . | −0.44 | 1.03 | . | . | . | −0.45 | 0.19 |
| Val | 431 | . | . | B | B | . | . | . | −0.44 | 0.27 | . | . | . | −0.10 | 0.24 |
| Gly | 432 | . | . | B | . | . | T | . | −0.44 | 0.31 | . | . | F | 0.50 | 0.28 |
| Ser | 433 | . | . | . | . | T | T | . | −0.96 | 0.29 | . | . | F | 0.85 | 0.58 |
| Asp | 434 | . | . | . | . | T | T | . | −0.50 | 0.33 | . | . | F | 0.80 | 0.65 |
| Gly | 435 | . | . | . | . | T | T | . | 0.36 | 0.44 | . | . | F | 0.60 | 1.03 |
| Tyr | 436 | . | . | B | . | . | . | . | 0.87 | 0.41 | . | * | . | −0.20 | 1.33 |
| Leu | 437 | . | . | B | . | . | . | . | 1.32 | 0.46 | . | * | . | −0.40 | 0.79 |
| Tyr | 438 | . | . | B | . | . | . | . | 1.28 | 0.46 | * | . | . | −0.25 | 1.56 |
| Gln | 439 | . | . | B | . | . | . | . | 0.99 | 0.46 | * | . | F | −0.25 | 0.98 |
| Gly | 440 | . | . | . | . | T | T | . | 1.30 | 0.61 | . | . | F | 0.50 | 1.25 |
| Arg | 441 | . | . | . | . | T | T | . | 1.26 | 0.43 | . | * | F | 0.50 | 1.09 |
| Gly | 442 | . | . | . | . | T | T | . | 1.21 | 0.59 | . | . | . | 0.20 | 0.66 |
| Trp | 443 | . | . | . | . | . | T | C | 1.11 | 0.83 | . | * | . | 0.00 | 0.50 |
| His | 444 | . | . | . | B | . | . | C | 0.52 | 0.83 | . | * | . | −0.40 | 0.25 |
| Trp | 445 | . | . | B | B | . | . | . | 0.83 | 1.33 | * | . | . | −0.60 | 0.26 |
| Val | 446 | . | . | B | B | . | . | . | 0.41 | 1.40 | * | * | . | −0.60 | 0.33 |
| Gly | 447 | . | . | B | B | . | . | . | 0.87 | 0.97 | * | * | . | −0.40 | 0.35 |
| Ala | 448 | . | . | B | . | . | . | . | 0.81 | 0.47 | * | * | . | −0.40 | 0.65 |
| His | 449 | . | . | . | . | . | T | C | 0.60 | −0.01 | * | * | . | 1.20 | 0.87 |
| Thr | 450 | . | . | . | . | . | T | C | 0.89 | 0.10 | * | * | F | 1.20 | 1.38 |
| Arg | 451 | . | . | . | . | T | T | . | 1.44 | 0.07 | . | * | F | 1.70 | 2.20 |
| Gly | 452 | . | . | . | . | T | T | . | 1.90 | −0.04 | . | * | F | 2.60 | 2.17 |
| Tyr | 453 | . | . | . | . | . | T | . | 2.14 | −0.54 | . | . | F | 3.00 | 2.94 |
| Asn | 454 | . | . | . | . | T | T | C | 1.48 | −0.60 | . | . | F | 2.70 | 1.48 |
| Ser | 455 | . | . | . | . | T | T | C | 1.44 | 0.19 | . | . | F | 1.50 | 1.30 |
| Arg | 456 | . | . | . | . | T | T | . | 0.48 | 0.19 | . | . | F | 1.25 | 0.82 |
| Gly | 457 | . | . | . | . | T | T | . | 0.23 | 0.07 | . | . | F | 0.95 | 0.38 |
| Phe | 458 | . | . | B | B | . | . | . | −0.22 | 0.17 | . | . | . | −0.30 | 0.29 |
| Gly | 459 | . | . | B | B | . | . | . | −1.08 | 0.57 | . | . | . | −0.60 | 0.13 |
| Val | 460 | . | . | B | B | . | . | . | −1.12 | 1.21 | . | . | . | −0.60 | 0.09 |
| Ala | 461 | . | . | B | B | . | . | . | −1.23 | 1.21 | . | . | . | −0.60 | 0.11 |
| Phe | 462 | . | . | B | B | . | . | . | −1.13 | 0.83 | . | . | . | −0.60 | 0.18 |
| Val | 463 | . | . | B | B | . | . | . | −0.74 | 1.16 | . | . | . | −0.60 | 0.37 |
| Gly | 464 | . | . | B | B | . | . | . | −0.74 | 1.00 | . | . | . | −0.60 | 0.53 |
| Asn | 465 | . | . | . | B | T | . | . | −0.19 | 0.93 | . | * | F | −0.05 | 0.61 |
| Tyr | 466 | . | . | . | . | T | T | . | −0.41 | 0.53 | . | . | F | 0.50 | 1.09 |
| Thr | 467 | . | . | . | . | . | T | C | 0.08 | 0.57 | * | . | F | 0.15 | 0.91 |
| Gly | 468 | . | . | . | . | T | T | . | 0.93 | 0.57 | * | . | F | 0.56 | 0.88 |
| Ser | 469 | . | . | . | . | . | T | C | 1.28 | 0.57 | * | * | F | 0.57 | 0.90 |
| Leu | 470 | . | . | . | . | . | T | C | 0.69 | −0.19 | * | . | F | 1.83 | 1.08 |
| Pro | 471 | . | . | B | . | . | T | . | 0.34 | −0.17 | . | . | F | 1.84 | 1.10 |
| Asn | 472 | . | . | . | . | . | T | C | −0.16 | −0.10 | . | * | F | 2.10 | 0.83 |
| Glu | 473 | A | . | . | . | . | T | . | 0.19 | 0.20 | . | * | F | 1.09 | 0.83 |
| Ala | 474 | A | A | . | . | . | . | . | 0.18 | −0.09 | . | . | . | 0.93 | 0.86 |
| Ala | 475 | A | A | . | . | . | . | . | 0.13 | −0.03 | * | * | . | 0.72 | 0.78 |
| Leu | 476 | A | A | . | B | . | . | . | 0.46 | 0.21 | * | . | . | −0.09 | 0.33 |
| Asn | 477 | A | A | . | B | . | . | . | 0.46 | 0.21 | * | . | . | −0.30 | 0.64 |
| Thr | 478 | . | A | B | B | . | . | . | −0.13 | −0.29 | * | . | F | 0.60 | 1.07 |
| Val | 479 | . | A | B | B | . | . | . | −0.36 | −0.29 | * | . | F | 0.60 | 1.30 |
| Arg | 480 | . | A | B | B | . | . | . | 0.02 | −0.29 | * | . | F | 0.45 | 0.67 |
| Asp | 481 | . | . | . | B | T | . | . | 0.53 | −0.26 | * | . | F | 0.85 | 0.72 |
| Ala | 482 | . | . | B | . | . | . | . | −0.13 | −0.36 | * | . | F | 0.80 | 1.29 |
| Leu | 483 | . | . | B | . | . | T | . | −0.41 | −0.43 | . | * | F | 0.85 | 0.35 |
| Pro | 484 | . | . | B | . | . | T | . | −0.44 | 0.07 | . | * | . | 0.10 | 0.21 |
| Ser | 485 | . | . | B | . | . | T | . | −0.44 | 0.76 | . | * | . | −0.20 | 0.15 |
| Cys | 486 | . | . | B | . | . | T | . | −0.44 | 0.26 | * | * | . | 0.10 | 0.35 |
| Ala | 487 | . | . | B | . | . | . | . | −0.20 | −0.43 | * | * | . | 0.30 | 0.40 |
| Ile | 488 | . | A | B | . | . | . | . | −0.20 | −0.43 | * | . | . | 0.30 | 0.29 |
| Arg | 489 | . | A | B | . | . | . | . | −0.80 | −0.13 | * | * | . | 0.30 | 0.45 |
| Glu | 490 | . | A | B | . | . | . | . | −0.39 | −0.01 | * | * | F | 0.45 | 0.37 |
| Gly | 491 | . | A | B | . | . | . | . | 0.07 | −0.51 | * | * | F | 0.90 | 1.03 |
| Leu | 492 | . | A | B | . | . | . | . | 0.66 | −0.77 | * | * | F | 1.03 | 0.81 |
| Leu | 493 | . | A | B | . | . | . | . | 1.30 | −0.77 | * | * | F | 1.31 | 0.78 |
| Arg | 494 | . | . | . | . | . | T | C | 1.23 | −0.01 | * | * | F | 2.04 | 1.24 |
| Pro | 495 | A | . | . | . | . | T | . | 0.42 | −0.44 | * | * | F | 2.12 | 3.00 |
| Asp | 496 | . | . | . | . | T | T | . | −0.04 | −0.44 | * | * | F | 2.80 | 3.00 |
| Tyr | 497 | A | . | . | . | . | T | . | 0.42 | −0.44 | * | * | F | 2.12 | 1.26 |
| Lys | 498 | . | A | B | . | . | . | . | 1.20 | −0.01 | * | * | F | 1.29 | 0.81 |
| Leu | 499 | . | A | B | . | . | . | . | 1.20 | 0.06 | * | * | . | 0.26 | 0.66 |
| Leu | 500 | . | A | B | . | . | . | . | 1.41 | 0.06 | * | * | . | −0.02 | 0.82 |
| Gly | 501 | A | A | . | . | . | . | . | 0.60 | −0.30 | . | * | . | 0.30 | 0.71 |
| His | 502 | A | A | . | . | . | . | . | −0.01 | 0.39 | . | . | . | −0.30 | 0.71 |
| Arg | 503 | A | . | . | B | . | . | . | −0.87 | 0.34 | . | . | . | −0.30 | 0.64 |
| Gln | 504 | . | . | B | B | . | . | . | −0.37 | 0.34 | . | . | . | −0.30 | 0.53 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 505 | . | . | B | B | . | . | . | 0.41 | 0.40 | . | . | . | −0.30 | 0.57 |
| Val | 506 | . | . | B | B | . | . | . | 0.09 | 0.40 | . | . | . | −0.30 | 0.39 |
| Leu | 507 | . | . | B | B | . | . | . | −0.09 | 0.97 | . | . | . | −0.60 | 0.12 |
| Thr | 508 | . | . | B | B | . | . | . | −0.54 | 1.00 | . | . | . | −0.60 | 0.23 |
| His | 509 | . | . | B | B | . | . | . | −0.54 | 0.74 | . | . | . | −0.60 | 0.30 |
| Cys | 510 | . | . | B | . | . | T | . | −0.32 | 0.50 | . | . | . | −0.20 | 0.59 |
| Pro | 511 | . | . | . | . | T | T | . | −0.28 | 0.31 | . | . | F | 0.65 | 0.42 |
| Gly | 512 | . | . | . | . | T | T | . | −0.17 | 0.51 | . | * | F | 0.35 | 0.25 |
| Asn | 513 | . | . | . | . | T | T | . | 0.14 | 0.80 | * | * | F | 0.35 | 0.41 |
| Ala | 514 | . | A | B | . | . | . | . | −0.63 | 0.63 | * | * | . | −0.60 | 0.42 |
| Leu | 515 | . | A | B | . | . | . | . | −0.78 | 0.89 | * | . | . | −0.60 | 0.35 |
| Phe | 516 | . | A | B | . | . | . | . | −0.46 | 1.14 | * | . | . | −0.60 | 0.18 |
| Asn | 517 | . | A | B | . | . | . | . | −0.42 | 0.74 | * | . | . | −0.60 | 0.35 |
| Leu | 518 | . | A | B | . | . | . | . | −0.71 | 0.73 | * | . | . | −0.60 | 0.61 |
| Leu | 519 | . | A | B | . | . | . | . | −0.33 | 0.96 | * | . | . | −0.60 | 0.75 |
| Arg | 520 | . | A | . | . | T | . | . | 0.44 | 0.60 | * | . | . | −0.20 | 0.72 |
| Thr | 521 | . | . | . | . | T | . | . | 0.44 | 0.70 | * | * | . | 0.15 | 1.18 |
| Trp | 522 | . | . | . | . | . | T | C | 0.13 | 0.80 | * | . | . | 0.15 | 1.24 |
| Pro | 523 | . | . | . | . | . | T | C | 0.94 | 0.60 | * | . | . | 0.00 | 0.91 |
| His | 524 | . | . | . | . | . | T | C | 0.90 | 0.60 | * | * | . | 0.15 | 1.10 |
| Phe | 525 | . | . | . | . | . | T | C | 0.79 | 0.76 | * | . | . | 0.00 | 0.77 |
| Thr | 526 | . | A | . | . | . | . | C | 1.10 | −0.16 | . | . | . | 0.50 | 0.87 |
| Glu | 527 | A | A | . | . | . | . | . | 1.00 | −0.19 | . | . | F | 0.60 | 1.03 |
| Val | 528 | A | A | . | . | . | . | . | 0.82 | −0.26 | . | . | . | 0.45 | 1.51 |
| Glu | 529 | A | A | . | . | . | . | . | 0.47 | −0.61 | . | . | . | 0.75 | 1.34 |
| Asn | 530 | A | A | . | . | . | . | . | 0.78 | −0.67 | * | . | . | 0.60 | 0.99 |

Among highly preferred fragments in this regard are those that comprise regions of PGRP-L that combine several structural features, such as two, three, four, five, or more of the features set out above.

Other preferred fragments are biologically active PGRP-L fragments. Biologically active fragments are those exhibiting activity similar, but not necessarily identical, to an activity of the PGRP-L polypeptide. The biological activity of the fragments may include an improved desired activity, or a decreased undesirable activity.

However, many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1188 of SEQ ID NO:1, b is an integer of 15 to PGRP-L, where both a and b correspond to the positions of nucleotide residues shown in SEQ ID NO:1, and where the b is greater than or equal to a+14.

In another aspect, the invention provides peptides and polypeptides comprising epitope-bearing portions of the polypeptides of the present invention. These epitopes are immunogenic and/or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al. (1983) Proc. Natl. Acad. Sci. USA 81:3998–4002. However, antibodies can be made to any antigenic epitope, regardless of whether it is an immunogenic epitope, by using methods such as phage display. See e.g., Petersen G. et al. (1995) Mol. Gen. Genet. 249:425–431. Therefore, included in the present invention are both immunogenic epitopes and antigenic epitopes.

A list of exemplified amino acid sequences comprising immunogenic epitopes are shown in Tables I and II. The Jameson-Wolf antigenic analysis was performed using the computer program PROTEAN, using default parameters (Version 3.11 for the Power Macintosh, DNASTAR, Inc., 1228 South Park Street Madison, Wis.). Portions of polypeptides not listed in Tables I and II are not considered non-immunogenic. The immunogenic epitopes of Tables I and II are an exemplified list, not an exhaustive list, because other immunogenic epitopes are merely not recognized as such by the particular algorithm used. Amino acid residues comprising other immunogenic epitopes may be routinely determined using algorithms similar to the Jameson-Wolf analysis or by in vivo testing for an antigenic response using methods known in the art. See, e.g., Geysen et al., supra; U.S. Pat. Nos. 4,708,781; 5,194,392; 4,433,092; and 5,480, 971 (said references incorporated by reference in their entireties).

Antigenic epitope-bearing peptides and polypeptides of the invention preferably contain a sequence of at least 5, at least 6, at least 9, at least 10, at least 15, at least 20, at least 25, at least 30, and more preferably between about 30 to about 50 amino acids contained within the amino acid sequence of a polypeptide of the invention (e.g., polypeptides contained in the amino acid sequence shown in FIGS. 1A–B (SEQ ID NO:2), and polypeptides contained in the amino acid sequence shown in FIGS. 2A–C (SEQ ID NO:4). Non-limiting examples of antigenic polypeptides or peptides that can be used to generate hPGRP-L-specific antibodies include: a polypeptide comprising amino acid residues in SEQ ID NO:2 from about Gly-12 to Phe-18; from Ala-34 to Ala-47; from Gly-51 to Tyr-57; from Gln-64 to Leu-75; from Arg-80 to His-84; from Thr-96 to Tyr-133; from Gly-135 to Leu-137; from Ser-145 to Thr-154; from Ala-161 to Pro-167; and from Pro-172 to Ser-174 as depicted in FIGS. 1A–B (SEQ ID NO:2). Non-limiting examples of antigenic polypeptides or peptides that can be used to generate mPGRP-L-specific antibodies include: a polypeptide comprising amino acid residues in SEQ ID NO:4 from about Glu-18 to Ser-24; from Ala-37 to Val-45; from Ala-59 to Leu-68; from Ala-76 to Leu-93; from Ala-101 to Tyr-111; from Ala-116 to Val-122; from Leu-143 to Ala-159; from Phe-172 to Arg-197; from His-213 to Trp-229; from Asp-242 to Ser-246; from Gln-268 to Pro-275; from Val-288 to Ala-305; from Lys-325 to His-330; from Asn-335 to Gln-340; from Ala-348 to Thr-353; from Ile-362 to Leu-382; from Pro-397 to Cys-399; from Ala-406 to Gln-413; from Phe-415 to Gly-426; from Gly-432 to Gly-435; from Gly-440 to Gly-442; from His-449 to Gly-457; from Tyr-466 to Ala-475; from Thr-478 to Pro-484; from Cys-486 to Leu-499; from Pro-511 to Asn-513; and from Thr-521 to Asn-530 as depicted in FIGS. 2A–C (SEQ ID NO:4). These polypeptide fragments have been determined to bear antigenic epitopes of the PGRP-L proteins by the analysis of the Jameson-Wolf antigenic index, as shown in FIGS. 4 and 5, below.

It is particularly pointed out that the amino acid sequences of Tables I and II comprise immunogenic epitopes. Tables I and II lists only the critical residues of immunogenic epitopes determined by the Jameson-Wolf analysis. Thus, additional flanking residues on either the N-terminal, C-terminal, or both N- and C-terminal ends may be added to the sequences of Tables I and II to generate an epitope-bearing polypeptide of the present invention. Therefore, the immunogenic epitopes of Tables I and II may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences.

Polypeptides of the present invention, such as, for example, polypeptides contained in the amino acid sequence shown in FIGS. 1A–B (SEQ ID NO:2), and polypeptides contained in the amino acid sequence shown in FIGS. 2A–C (SEQ ID NO:4, comprising immunogenic and/or antigenic epitopes are at least 7 amino acids residues in length. "At least" means that a polypeptide of the present invention comprising an immunogenic and/or antigenic epitope may be 7 amino acid residues in length or any integer between 7 amino acids and the number of amino acid residues of the full length polypeptides of the invention. Preferred polypeptides comprising immunogenic and/or antigenic epitopes are at least 10, 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full-length polypeptide are included in the present invention.

The immunogenic and/or antigenic epitope-bearing fragments may be specified by either the number of contiguous amino acid residues, as described above, or further specified by N-terminal and C-terminal positions of these fragments on the amino acid sequence of SEQ ID NO:2. Every combination of a N-terminal and C-terminal position that a fragment of, for example, at least 7 or at least 15 contiguous amino acid residues in length could occupy on the amino acid sequence of SEQ ID NO:2 is included in the invention. Again, "at least 7 contiguous amino acid residues in length" means 7 amino acid residues in length or any integer between 7 amino acids and the number of amino acid residues of the full-length polypeptide of the present invention. Specifically, each and every integer between 7 and the number of amino acid residues of the full-length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., Antibodies: A Laboratory Manual, (Cold Spring Harbor Laboratory Press; 2nd Ed. 1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10–20 mgs of 248 individual and distinct 13 residue peptides representing single amino acid variants of a segment of the HA1 polypeptide, all of which were prepared and characterized (by ELISA-type binding studies) in less than four weeks (Houghten, R. A. Proc. Natl. Acad. Sci. USA 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al. (1985) Proc. Natl. Acad. Sci. 82:5131–5135 at 5134.

Epitope-bearing polypeptides of the present invention are used to induce antibodies according to methods well known in the art including, but not limited to, in vivo immunization, in vitro immunization, and phage display methods. See, e.g., Sutcliffe, et al., supra; Wilson, et al., supra, and Bittle, et al. (1985) J. Gen. Virol. 66:2347–2354. If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al. (1988) Nature 331:84–86. Fusion proteins that have a disulfide-linked dimeric structure due to the IgG portion can also be more efficient in binding and neutralizing other molecules than monomeric polypeptides or fragments thereof alone. See, e.g., Fountoulakis et al. (1995) J. Biochem. 270:3958–3964. Nucleic acids encoding the above epitopes can also be recombined with a gene of interest as an epitope tag to aid in detection and purification of the expressed polypeptide.

Polynucleotide and Polypeptide Variants

The invention also encompasses PGRP-L polypeptide variants comprising, or alternatively, consisting of, a polypeptide sequence at least 80%, 85%, 90%, 95%, 96%, 97%, 98%, or 99% identical to a polypeptide sequence disclosed herein, such as, for example, the mature polypeptide sequence disclosed in FIGS. 2A–C, or the sequence disclosed in FIGS. 1A–B, or any of the polypeptide fragments described herein. Polynucleotides encoding these polypeptides are also encompassed by the invention.

The invention also encompasses PGRP-L polynucleotide variants comprising, or alternatively, consisting of, a polynucleotide sequence at least 80%, 85%, 90%, 95%, 96%, 97%, 98%, or 99% identical to a polypeptide sequence disclosed herein, such as, for example, a nucleic acid sequence disclosed in FIGS. 1A–B, FIGS. 2A–B, the complementary strand thereto, or fragments thereof. Polypeptides encoded by these polynucleotides are also encompassed by the invention.

"Variant" refers to a polynucleotide or polypeptide differing from the PGRP-L polynucleotide or polypeptide, but retaining essential properties thereof. Generally, variants are overall closely similar, and, in many regions, identical to the PGRP-L polynucleotide or polypeptide.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the PGRP-L polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO:1, the ORF (open reading frame), or any fragment specified as described herein.

As a practical matter, whether any particular nucleic acid molecule or polypeptide is at least 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence shown in SEQ ID NO:2, the amino acid sequence shown in SEQ ID NO:4, or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

The PGRP-L variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. PGRP-L polynucleotide variants can be produced for a variety of reasons, e.g., to optimize codon expression for a particular host (change codons in the human mRNA to those preferred by a bacterial host such as $E.\ coli$).

Naturally occurring PGRP-L variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the PGRP-L polypeptides. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wildtype.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes PGRP-L polypeptide variants (e.g., variants of the PGRP-L polypeptide disclosed in FIGS. 1A–B and variants of the PGRP-L polypeptide disclosed in FIGS. 2A–C), which show substantial biological activity. Such variants include deletions, insertions, inversions, repeats, and substitutions selected according to general rules known in the art so as to have little effect on activity.

The present application is directed to nucleic acid molecules at least 80%, 85%, 90%, 95%, 96%, 97%, 98% or 99% identical to a nucleic acid sequence disclosed herein, (e.g., encoding a polypeptide having the amino acid sequence of an N and/or C terminal deletion disclosed below as m-n of SEQ ID NO:2), irrespective of whether they encode a polypeptide having PGRP-L functional activity. This is because even where a particular nucleic acid molecule does not encode a polypeptide having PGRP-L functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having PGRP-L functional activity include, inter alia, (1) isolating a PGRP-L gene or allelic or splice variants thereof in a cDNA library; (2) in situ hybridization (e.g., "FISH") to metaphase chromosomal spreads to provide precise chromosomal location of the PGRP-L gene, as described in Verma et al., Human Chromosomes: A Manual of Basic Techniques, Pergamon Press, New York (1988); and (3) Northern Blot analysis for detecting PGRP-L mRNA expression in specific tissues.

Preferred, however, are nucleic acid molecules having sequences at least 80%, 85%, 90%, 95%, 96%, 97%, 98% or 99% identical to a nucleic acid sequence disclosed herein, which do, in fact, encode a polypeptide having PGRP-L functional activity. By "a polypeptide having PGRP-L functional activity" is intended polypeptides exhibiting activity similar, but not necessarily identical, to a functional activity of the PGRP-L polypeptides of the present invention (e.g., soluble PGRP-L (e.g., having sequences contained in the extracellular domain of PGRP-L) as measured, for example, in a particular immunoassay or biological assay. For example, a PGRP-L functional activity can routinely be measured by determining the ability of a PGRP-L polypeptide to bind a PGRP-L ligand. PGRP-L functional activity may also be measured by determining the ability of a polypeptide, such as cognate ligand which is free or expressed on a cell surface, to induce cells expressing the polypeptide.

Of course, due to the degeneracy of the genetic code, one of ordinary skill in the art will immediately recognize that a large number of the nucleic acid molecules having a sequence at least 80%, 85%, 90%, 95%, 96%, 97%, 98%, or 99% identical to the nucleic acid sequence of the deposited cDNA, the nucleic acid sequence shown in FIGS. 1A–B (SEQ ID NO:1), the nucleotide sequence shown in FIGS. 2A–B (SEQ ID NO:3), or fragments thereof, will encode polypeptides "having PGRP-L functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number ill also encode a polypeptide having PGRP-L functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306–1310 (1990), wherein the authors indicate there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of PGRP-L include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, PGRP-L polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of a PGRP-L polypeptide (e.g., a polypeptide disclosed in FIGS. 1A–B (SEQ ID NO:2), a polypeptide disclosed in FIGS. 2A–C (SEQ ID NO:4)), having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of a PGRP-L polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIGS. 1A–B or fragments thereof (e.g., the mature form and/or other fragments described herein), is 1–5, 5–10, 5–25, 5–50, 10–50 or 50–150, conservative amino acid substitutions are preferable. In specific embodiments, the number of additions, substitutions, and/or deletions in the amino acid sequence of FIGS. 2A–C or fragments thereof (e.g., the mature form and/or other fragments described herein), is 1–5, 5–10, 5–25, 5–50, 10–50 or 50–150, conservative amino acid substitutions are preferable.

Antibodies

Further polypeptides of the invention relate to antibodies and T-cell antigen receptors (TCR) which immunospecifically bind a polypeptide, polypeptide fragment, or variant of SEQ ID NO:2 and/or 4, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen-binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific, or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, or by size in contiguous amino acid residues. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$M, $5 \times 10^{-7}$ M, $10^7$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{--}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7): 3170–3179 (1998); Prat et al., J. Cell. Sci. 111(Pt2): 237–247 (1998); Pitard et al., J. Imunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phages used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5) :489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or alternatively, under lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2 and/or 4.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a EDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (See e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2 and/or 4 may be fused or conjugated to the above antibody portions to increase the in vivo half life of the polypeptides or for use in immunoassays using methods known in the art. Further, the polypeptides corresponding to SEQ ID NO:2 and/or 4 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fe portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriaziny-lamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular apopulations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trayslol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^3H$ or $^{125}I$) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5): 155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contain nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitate delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993), present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Fusion Proteins

Any PGRP-L polypeptide of the invention can be used to generate fusion proteins. For example, the PGRP-L polypeptide, when fused to a second protein, can be used as an antigenic tag. Antibodies raised against the PGRP-L polypeptides of the invention can be used to indirectly detect the second protein by binding to the PGRP-L. Moreover, because secreted proteins target cellular locations based on trafficking signals, the PGRP-L polypeptides of the invention can be used as a targeting molecule once fused to other proteins.

Examples of domains that can be fused to PGRP-L polypeptides of the invention include not only heterologous signal sequences, but also other heterologous functional regions. The fusion does not necessarily need to be direct, but may occur through linker sequences.

In certain preferred embodiments, PGRP-L proteins of the invention comprise fusion proteins wherein the PGRP-L polypeptides are those described above as m-n. In preferred embodiments, the application is directed to nucleic acid molecules at least 80%, 85%, 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

Moreover, fusion proteins may also be engineered to improve characteristics of the PGRP-L polypeptide. For instance, a region of additional amino acids, particularly charged amino acids, may be added to the N-terminus of the PGRP-L polypeptide to improve stability and persistence during purification from the host cell or subsequent handling and storage. Also, peptide moieties may be added to the PGRP-L polypeptide to facilitate purification. Such regions may be removed prior to final preparation of the PGRP-L polypeptide. The addition of peptide moieties to facilitate handling of polypeptides are familiar and routine techniques in the art.

Moreover, PGRP-L polypeptides, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995)).

Moreover, the PGRP-L polypeptides can be fused to marker sequences, such as a peptide which facilitates purification of PGRP-L. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (See, Wilson et al., Cell 37:767 (1984)).

Thus, any of these above fusions can be engineered using the PGRP-L polynucleotides or the polypeptides.

Vectors, Host Cells, and Protein Production

The present invention also relates to vectors containing the PGRP-L polynucleotide, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

PGRP-L polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The PGRP-L polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that PGRP-L polypeptides may in fact be expressed by a host cell lacking a recombinant vector.

PGRP-L polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Most preferably, high performance liquid chromatography ("HPLC") is employed for purification.

PGRP-L polypeptides, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the PGRP-L polypeptides may be glycosylated or may be non-glycosylated. In addition, full-length PGRP-L polypeptides, isolated using techniques described herein, may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., PGRP-L coding sequence), and/or to include genetic material (e.g., heterologous polynucleotide sequences) that is operably associated with PGRP-L polynucleotides of the invention, and which activates, alters, and/or amplifies endogenous PGRP-L polynucleotides. For example, techniques known in the art may be used to operably associate heterologous control regions (e.g., promoter and/or enhancer) and endogenous PGRP-L polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller, M., et al., 1984, Nature 310:105–111). For example, a peptide corresponding to a fragment of the PGRP-L polypeptides of the invention can be synthesized by use of a peptide synthesizer. Furthermore, if desired, nonclassical amino acids or chemical amino acid analogs can be introduced as a substitution or addition into the PGRP-L polynucleotide sequence. Non-classical amino acids include, but are not limited to, the D-isomers of the common amino acids, 2,4-diaminobutyric acid, α-amino isobutyric acid, 4-aminobutyric acid, Abu, 2-amino butyric acid, γ-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London SerA* 317:415 (1986)).

The invention encompasses PGRP-L polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of PGRP-L which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

The PGRP-L polypeptides of the invention may be in monomers or multimers (i.e., dimers, trimers, tetramers and higher multimers). Accordingly, the present invention relates to monomers and multimers of the PGRP-L polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only PGRP-L polypeptides of the invention (including PGRP-L fragments, variants, splice variants, and fusion proteins, as described herein). These homomers may contain PGRP-L polypeptides having identical or different amino acid sequences. In a specific embodiment, a homomer of the invention is a multimer containing only PGRP-L polypeptides having an identical amino acid sequence. In another specific embodiment, a homomer of the invention is a multimer containing PGRP-L polypeptides having different amino acid sequences. In specific embodiments, the multimer of the invention is a homodimer (e.g., containing PGRP-L polypeptides having identical or different amino acid sequences) or a homotrimer (e.g., containing PGRP-L polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the PGRP-L polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the PGRP-L polypeptides of the invention. Such covalent associations may involve one or more amino acid residues contained in the polypeptide sequence (e.g., that recited in SEQ ID NO:2, or contained in the polypeptide encoded by the clone HPJEV37). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a PGRP-L fusion protein. In one example, covalent associations are between the heterologous sequence contained in a fusion protein of the invention (see, e.g., U.S. Pat. No. 5,478,925). In a specific example, the covalent associations are between the heterologous sequence contained in a PGRP-L-Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication No. WO 98/49305, the contents of which are herein incorporated by reference in its entirety). In another embodiment, two or more PGRP-L polypeptides of the invention are joined through synthetic linkers (e.g., peptide, carbohydrate or soluble polymer linkers). Examples include those peptide linkers described in U.S. Pat. No. 5,073,627 (hereby incorporated by reference). Proteins comprising multiple PGRP-L polypeptides separated by peptide linkers may be produced using conventional recombinant DNA technology.

Another method for preparing multimer PGRP-L polypeptides of the invention involves use of PGRP-L polypeptides fused to a leucine zipper polypeptide sequence. Leucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric PGRP-L proteins are those described in PCT application WO 94/10308, hereby incorporated by reference. Recombinant fusion proteins comprising a soluble PGRP-L polypeptide fused to a peptide that dimerizes or trimerizes in solution are expressed in suitable host cells, and the resulting soluble multimeric PGRP-L is recovered from the culture supernatant using techniques known in the art.

Trimeric PGRP-L may offer the advantage of enhanced biological activity. Preferred leucine zipper moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric PGRP-L.

In another example, proteins of the invention are associated by interactions between Flag® polypeptide sequence contained in Flag®-PGRP-L fusion proteins of the invention. In a further embodiment, associations proteins of the invention are associated by interactions between heterologous polypeptide sequence contained in Flag®-PGRP-L fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

Uses of the PGRP-L Polynucleotides

The PGRP-L polynucleotides of the invention have numerous uses that will be immediately apparent to those skilled in the art. The following description should be considered exemplary and utilizes known techniques.

There exists an ongoing need to identify new chromosome markers, since few chromosome marking reagents, based on actual sequence data (repeat polymorphisms), are presently available.

Briefly, sequences can be mapped to chromosomes by preparing PCR primers (preferably 15–25 bp) from the sequences shown in SEQ ID NO:1. Primers can be selected using computer analysis so that primers do not span more than one predicted exon in the genomic DNA. These primers are then used for PCR screening of somatic cell hybrids containing individual human chromosomes. Only those hybrids containing the human PGRP-L gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the PGRP-L polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the PGRP-L polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the PGRP-L polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library)). Assuming 1 megabase mapping resolution and one gene per 20 kb, a cDNA precisely localized to a chromosomal region associated with the disease could be one of 50–500 potential causative genes.

Thus, once coinheritance is established, differences in the PGRP-L polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations is ascertained. Mutations observed in some or all affected individuals, but not in normal individuals, indicates that the mutation may cause the disease. However, complete sequencing of the PGRP-L polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using PGRP-L polynucleotides. Any of these alterations (altered expression, chromosomal rearrangement, or mutation) can be used as a diagnostic or prognostic marker.

In addition to the foregoing, a PGRP-L polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

PGRP-L polynucleotides are also useful in gene therapy. One goal of gene therapy is to insert a normal gene into an organism having a defective gene, in an effort to correct the genetic defect. PGRP-L offers a means of targeting such genetic defects in a highly accurate manner. Another goal is to insert a new gene that was not present in the host genome, thereby producing a new trait in the host cell.

The PGRP-L polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The PGRP-L polynucleotides can be used as additional DNA markers for RFLP.

The PGRP-L polynucleotides can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once a unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, PGRP-L polynucleotides can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from PGRP-L sequences. Panels of such reagents can identify tissue by species and/or by organ type. In a similar fashion, these reagents can be used to screen tissue cultures for contamination.

Because PGRP-L is found expressed in liver tissue, PGRP-L polynucleotides are useful as hybridization probes for differential identification of the tissue(s) or cell type(s) present in a biological sample. Similarly, polypeptides and antibodies directed to PGRP-L polypeptides are useful to provide immunological probes for differential identification of the tissue(s) or cell type(s). In addition, for a number of disorders of the above tissues or cells, particularly of the hepatic and immune systems, significantly higher or lower levels of PGRP-L gene expression may be detected in certain tissues (e.g., liver, immune, cancerous and wounded tissues) or bodily fluids (e.g., lymph, serum, plasma, urine, synovial fluid or spinal fluid) taken from an individual having such a disorder, relative to a "standard" PGRP-L gene expression level, i.e., the PGRP-L expression level in healthy tissue from an individual not having the hepatic and/or immune system disorder(s).

Thus, the invention provides a diagnostic method of a disorder, which involves: (a) assaying PGRP-L gene expression level in cells or body fluid of an individual; (b) comparing the PGRP-L gene expression level with a standard PGRP-L gene expression level, whereby an increase or decrease in the assayed PGRP-L gene expression level compared to the standard expression level is indicative of disorder in the hepatic and/or immune systems.

In the very least, the PGRP-L polynucleotides can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of PGRP-L Polypeptides

PGRP-L polypeptides of the invention have numerous uses that will be immediately apparent to those skilled in the art. The following description should be considered exemplary and utilizes known techniques.

PGRP-L polypeptides can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $^{131}$I, $^{112}$In, $^{99m}$Tc, ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F, $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which express the polypeptide encoded by a polynucleotide of the invention. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

In one embodiment, the invention provides a method for the specific delivery of compositions of the invention to cells by administering polypeptides of the invention (e.g., polypeptides encoded by polynucleotides of the invention and/or antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention in association with toxins or cytotoxic prodrugs.

By "toxin" is meant one or more compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, 103Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label polypeptides of the invention (including antibodies). Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

Thus, the invention provides a diagnostic method of a disorder, which involves (a) assaying the expression of PGRP-L polypeptide in cells or body fluid of an individual; (b) comparing the level of gene expression with a standard gene expression level, whereby an increase or decrease in the assayed PGRP-L polypeptide gene expression level compared to the standard expression level is indicative of a disorder.

Moreover, PGRP-L polypeptides can be used to treat disease. For example, patients can be administered PGRP-L polypeptides in an effort to replace absent or decreased levels of the PGRP-L polypeptide (e.g., such as with insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to PGRP-L polypeptides can also be used to treat disease. For example, administration of an antibody directed to a PGRP-L polypeptide can bind and reduce overproduction of the polypeptide. Similarly, administration of an antibody can activate the polypeptide, such as by binding to a polypeptide bound to a membrane (receptor).

At the very least, the PGRP-L polypeptides can be used as molecular weight markers on SDS-PAGE gels or on molecular sieve gel filtration columns using methods well known to those of skill in the art. PGRP-L polypeptides can also be used to raise antibodies, which in turn are used to measure protein expression from a recombinant cell, as a way of assessing transformation of the host cell. Moreover, PGRP-L polypeptides can be used to test the following biological activities.

Gene Therapy Methods

The present invention also encompasses the use of the polynucleotides of the invention in gene therapy. This gene therapy relates to the introduction of nucleic acid (DNA, RNA and antisense DNA or RNA) sequences into an animal to achieve expression of the PGRP-L polypeptide of the present invention. This method requires a polynucleotide which codes for a PGRP-L polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a PGRP-L polynucleotide ex vivo, with the engineered cells then being provided to a patient to be treated with the polypeptide. Such methods are well known in the art. For example, see Belldegrun, A., et al., J. Natl. Cancer Inst. 85: 207–216 (1993); Ferrantini, M. et al., Cancer Research 53: 1107–1112 (1993); Ferrantini, M. et al., J. Immunology 153: 4604–4615 (1994); Kaido, T., et al., Int. J. Cancer 60: 221–229 (1995); Ogura, H., et al., Cancer Research 50: 5102–5106 (1990); Santodonato, L., et al., Human Gene Therapy 7:1–10 (1996); Santodonato, L., et al., Gene Therapy 4:1246–1255 (1997); and Zhang, J.-F. et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the PGRP-L polynucleotide constructs can be delivered by any method that delivers injectable materials to the cells of an animal, such as, injection into the interstitial space of tissues (heart, muscle, skin, lung, liver, and the like). The PGRP-L polynucleotide constructs may be delivered in a pharmaceutically acceptable liquid or aqueous carrier.

In one embodiment, the PGRP-L polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the PGRP-L polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The PGRP-L polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of PGRP-L DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the β-actin promoter; and human growth hormone promoters. The promoter also may be the native promoter for PGRP-L.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The PGRP-L polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked PGRP-L DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

As is evidenced in the Examples, naked PGRP-L nucleic acid sequences administered in vivo results in the successful expression of PGRP-L polypeptide in the femoral arteries of rabbits.

The constructs may also be delivered with delivery vehicles such as viral sequences, viral particles, liposome formulations, lipofectin, precipitating agents, etc. Such methods of delivery are known in the art.

In certain embodiments, the PGRP-L polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413–7416, which is herein incorporated by reference); mRNA (Malone et al., Proc. Natl. Acad. Sci. USA (1989) 86:6077–6081, which is herein incorporated by reference); and purified transcription factors (Debs et al., J. Biol. Chem. (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., Proc. Natl. Acad. Sci. USA 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially available dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255:10431; Szoka, F. and Papahadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589, 466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells can be engineered, ex vivo or in vivo, using a retroviral particle containing RNA which comprises a sequence encoding PGRP-L. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding PGRP-L. Such retroviral vector particles then may be employed, to transduce eukaryotic cells, either in vitro or in vivo. The transduced eukaryotic cells will express PGRP-L.

In certain other embodiments, cells are engineered, ex vivo or in vivo, with PGRP-L polynucleotide contained in an adenovirus vector. Adenovirus can be manipulated such that it encodes and expresses PGRP-L, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis.109:233–238). Finally, adenovirus mediated gene transfer has been demonstrated in a number of instances including transfer of alpha-1-antitrypsin and CFTR to the lungs of cotton rats (Rosenfeld, M. A. et al. (1991) Science 252:431–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The PGRP-L polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the PGRP-L polynucleotide construct. These viral particles are then used to transduce eukaryotic cells, either ex vivo or in vivo. The transduced cells will contain the PGRP-L polynucleotide construct integrated into its genome, and will express PGRP-L.

Another method of gene therapy involves operably associating heterologous control regions and endogenous polynucleotide sequences (e.g. encoding PGRP-L) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the PGRP-L desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous PGRP-L sequence is placed under the control of the promoter. The promoter then drives the expression of the endogenous PGRP-L sequence.

Preferably, the polynucleotide encoding PGRP-L contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotide constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities and Therapeutic Uses of PGRP-L

PGRP-L polynucleotides or polypeptides, or agonists or antagonists of PGRP-L, can be used in assays to test for one or more biological activities associated with PGRP-L, such as, for example, binding of peptidoglycan associated with innate immunity, and/or induction of apoptosis in cells (e.g. Examples 37, 38 and 39, respectively). If PGRP-L polynucleotides or polypeptides, or agonists or antagonists of PGRP-L, do exhibit activity in a particular assay, it is likely that PGRP-L may be involved in the diseases associated with the biological activity. Therefore, PGRP-L could be used to treat the associated disease.

PGRP-L polypeptides are believed to be involved in biological activities associated with immune system recognition, antigen presentation, and immune system activation. Accordingly, compositions of the invention (including polynucleotides, polypeptides and antibodies of the invention, fragments and variants thereof, and agonists and/or antagonists) may be used in the diagnosis, detection and/or treatment of diseases and/or disorders associated with the above listed biological activities. In preferred embodiments, compositions of the invention (including polynucleotides, polypeptides and antibodies of the invention, fragments and variants thereof, and agonists and/or antagonists) may be used in the diagnosis, detection and/or treatment of diseases and/or disorders relating to immune system recognition of infectious agents (e.g., microbial and viral infections, and/or as described under "Infectious Disease" below), antigen presentation (e.g., and/or as described under "Immune activity" and "Infectious Disease" below), immune system activation (e.g., autoimmune disorders, and/or as described under "Immune activity" below), apoptosis (e.g., as a cancer therapeutic, and/or as described under "Apoptosis Activity" below), osteoporosis, liver damage, neurodegenerative disorders, and aging. Thus, polynucleotides, translation products and antibodies (including agonists and/or antagonists) of the invention are useful in the diagnosis, detection and/or treatment of diseases and/or disorders associated with activities that include, but are not limited to, immune recognition of infectious agents, immune system activation, apoptosis, antigen presentation, osteoporosis, liver damage, neurodegenerative disorders, and aging.

More generally, polynucleotides, translation products and antibodies corresponding to this gene may be useful for the diagnosis, detection and/or treatment of diseases and/or disorders associated with the following systems.

Infectious Disease

As discussed in the background section, PGRP-L shares homology with human peptidoglycan recognition proteins, which are thought to play a role in peptidoglycan binding and antigen presentation, and thus mediate the immune response to bacterial infection. Accordingly, PGRP-L polynucleotides or polypeptides, or agonists or antagonists of PGRP-L, can be used to treat or detect infectious agents. For example, by mediating the immune response, particularly via peptidoglycan binding and antigen presentation to immune cells, infectious diseases may be treated. The immune response may be increased by either enhancing an existing immune response, or by initiating a new immune response. Alternatively, PGRP-L polynucleotides or polypeptides, or agonists or antagonists of PGRP-L, may also directly inhibit the infectious agent, without necessarily eliciting an immune response. It is believed that cells which express the PGRP-L polypeptide(s) mediate the recognition of pathogens (e.g., bacteria) and the processing and presentation of antigens to the immune system. By "a potent cellular response to infection" is intended any genotypic, phenotypic, and/or morphologic change to a cell, cell line, tissue, tissue culture or patient that is induced by infection from bacterial (Gram positive and negative), viral, fungal, parasitic, etc. As indicated, such cellular responses include not only normal physiological responses to infection (e.g., antigenic processing and presentation, immune response), but also diseases associated with aberrant immune system recognition, aberrant antigen processing and presentation in the immune system, aberrant immune system responses to infection, activation, survival, migration and differentiation of immune cells, as well as infections of immunocompromised individuals, and aberrant regulation of the proliferation/apoptosis of liver cells and/or other cells in the body (e.g., immune system cells).

Viruses are one example of an infectious agent that can cause disease or symptoms that can be treated or detected by PGRP-L polynucleotides or polypeptides, or agonists or antagonists of PGRP-L. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnavimidae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picomaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. PGRP-L polynucleotides or polypeptides, or agonists or antagonists of PGRP-L, can be used to treat or detect any of these symptoms or diseases.

Similarly, bacterial or fungal agents that can cause disease or symptoms and that can be treated or detected by PGRP-L polynucleotides or polypeptides, or agonists or antagonists of PGRP-L, include, but not limited to, the following Gram-Negative and Gram-positive bacterial families and fungi: Actinomycetales (e.g., *Corynebacterium, Mycobacterium, Norcardia*), Aspergillosis, Bacillaceae (e.g., *Anthrax, Clostridium*), Bacteroidaceae, *Blastomycosis, Bordetella, Borrelia,* Brucellosis, Candidiasis, *Campylobacter*, Coccidioidomycosis, Cryptococcosis, Dermatocycoses, Enterobacteriaceae (*Klebsiella, Salmonella, Serratia, Yersinia*), Erysipelothrix, *Helicobacter*, Legionellosis, Leptospirosis, *Listeria, Mycoplasmatales, Neisseriaceae* (e.g., *Acinetobacter*, Gonorrhea, Menigococcal), Pasteurellacea Infections (e.g., *Actinobacillus, Heamophilus, Pasteurella*), *Pseudomonas,* Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. PGRP-L polynucleotides or polypeptides, or agonists or antagonists of PGRP-L, can be used to treat or detect any of these symptoms or diseases.

Moreover, parasitic agents causing disease or symptoms that can be treated or detected by PGRP-L polynucleotides or polypeptides, or agonists or antagonists of PGRP-L, include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. PGRP-L polynucleotides or polypeptides, or agonists or antagonists of PGRP-L, can be used to treat or detect any of these symptoms or diseases.

Preferably, treatment using PGRP-L polynucleotides or polypeptides, or agonists or antagonists of PGRP-L, could either be by administering an effective amount of PGRP-L polypeptide to the patient, or by removing cells from the patient, supplying the cells with PGRP-L polynucleotide, and returning the engineered cells to the patient (ex vivo therapy). Moreover, the PGRP-L polypeptide or polynucleotide can be used as an antigen in a vaccine to raise an immune response against infectious disease.

Apoptosis Activity

Likewise, PGRP-L has been shown to have homology to tag7, which was shown by Kiselev et al. to induce apoptosis of murine L929 cells in vitro. Accordingly, diseases associated with increased cell survival or the inhibition of apoptosis that could be treated or detected by PGRP-L polynucleotides or polypeptides, as well as antagonists or agonists of PGRP-L, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, PGRP-L polynucleotides, polypeptides, and/or antagonists of the invention are used to inhibit growth, progression, and/or metastasis of cancers, in particular those listed above.

Additional diseases or conditions associated with increased cell survival that could be treated or detected by PGRP-L polynucleotides or polypeptides, or agonists or antagonists of PGRP-L, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by PGRP-L polynucleotides or polypeptides, as well as agonists or antagonists of PGRP-L, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Hyperproliferative diseases and/or disorders that could be detected and/or treated by PGRP-L polynucleotides or polypeptides, as well as agonists or antagonists of PGRP-L, include, but are not limited to neoplasms located in the: liver, abdomen, bone, breast, digestive system, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by PGRP-L polynucleotides or polypeptides, or agonists or antagonists of PGRP-L. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Immune Activity

Likewise, it was found that tag7 was constitutively expressed in hematopoietic and lymphoid tissues, which suggests that tag7 may be involved in normal immune system function. Accordingly, based upon the homology of PGRP-L to tag7, PGRP-L polynucleotides or polypeptides, or agonists or antagonists of PGRP-L, may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, PGRP-L polynucleotides or polypeptides, or agonists or antagonists of PGRP-L, can be used as a marker or detector of a particular immune system disease or disorder.

PGRP-L polynucleotides or polypeptides, or agonists or antagonists of PGRP-L, may be useful in treating or detecting deficiencies or disorders of hematopoietic cells. PGRP-L polynucleotides or polypeptides, or agonists or antagonists of PGRP-L, could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, DiGeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria. PGRP-L polynucleotides or polypeptides of the invention (e.g., agonistic anti-PGRP-L antibodies) and agonists or antagonists thereof, may also be useful in be treating, preventing, diagnosing, and/or prognosing autoimmune disorders. Many autoimmune disorders result from inappropriate recognition of self as foreign material by immune cells. This inappropriate recognition results in an immune response leading to the destruction of the host tissue. Therefore, the administration of polynucleotides and polypeptides of the invention that can inhibit an immune response, particularly the proliferation, differentiation, or chemotaxis of T-cells, may be an effective therapy in preventing autoimmune disorders.

Autoimmune diseases or disorders that may be treated, diagnosed, or prognosed using PGRP-L polynucleotides or polypeptides or PGRP-L agonists or antagonists (e.g., agonistic anti-PGRP-L antibodies) of the invention include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitus, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

In a specific preferred embodiment, rheumatoid arthritis is treated, prevented, prognosed and/or diagnosed using PGRP-L polypeptides, antibodies, or polynucleotides of the invention, and/or agonists or antagonists of the invention. In another specific preferred embodiment, systemic lupus erythematosus is treated, prevented, prognosed, and/or diagnosed using PGRP-L polypeptides, antibodies, or polynucleotides of the invention, and/or agonists or antagonists of the invention. In another specific preferred embodiment, idiopathic thrombocytopenia purpura is treated, prevented, prognosed, and/or diagnosed using PGRP-L polypeptides, antibodies, or polynucleotides of the invention, and/or agonists or antagonists of the invention. In another specific preferred embodiment IgA nephropathy is treated, prevented, prognosed and/or diagnosed using PGRP-L polypeptides, antibodies, or polynucleotides of the invention, and/or agonists or antagonists of the invention. In a preferred embodiment, the autoimmune diseases and disorders and/or conditions associated with the diseases and disorders recited above are treated, prevented, prognosed and/or diagnosed using anti-PGRP-L antibodies.

Similarly, allergic reactions and conditions, such as asthma (particularly allergic asthma) or other respiratory problems, may also be treated, prevented, prognosed and/or diagnosed using PGRP-L polypeptides, antibodies, or polynucleotides of the invention, and/or agonists or antagonists thereof. Moreover, these molecules can be used to treat, prevent, prognose and/or diagnose anaphylaxis, hypersensitivity to an antigenic molecule, or blood group incompatibility.

Moreover, inflammatory conditions may also be treated, diagnosed, prevented and/or prognosed with PGRP-L polypeptides, antibodies, or polynucleotides of the invention, and/or agonists or antagonists of PGRP-L (e.g., anti-PGRP-L antibodies) of the invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease, AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosis, diabetes mellitus (i.e., type 1 diabetes), and allogenic transplant rejection).

In specific embodiments, PGRP-L polypeptides, antibodies, or polynucleotides of the invention, and/or agonists or antagonists thereof, are useful to treat, diagnose, prevent, and/or prognose transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE). Organ rejection occurs by host immune cell destruction of the transplanted tissue through an immune response. Similarly, an immune response is also involved in GVHD, but, in this case, the foreign transplanted immune cells destroy the host tissues. PGRP-L polypeptides, antibodies, or polynucleotides of the invention, and/or agonists or antagonists of PGRP-L polypeptides, that inhibits an immune response, particularly the activation, proliferation, differentiation, or chemotaxis of T-cells, may be an effective therapy in preventing organ rejection or GVHD.

Similarly PGRP-L polypeptides, antibodies, or polynucleotides of the invention, and/or agonists or antagonists of the invention may also be used to modulate, diagnose, or prognose inflammation. For example, since PGRP-L polypeptides, antibodies, or polynucleotides of the invention, and/or agonists or antagonists of the invention, inhibit the activation, proliferation and/or differentiation of cells involved in an inflammatory response, these molecules can be used to treat, diagnose, or prognose, inflammatory conditions, both chronic and acute conditions, including, but not limited to, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, and resulting from over production of cytokines (e.g., TNF or IL-1).

Moreover, PGRP-L polypeptides, antibodies, or polynucleotides of the invention, and/or agonists or antagonists of the invention can also be used to modulate hemostatic (the stopping of bleeding) or thrombolytic activity (clot formation). For example, by increasing hemostatic or thrombolytic activity, PGRP-L polypeptides, antibodies, or polynucleotides of the invention, and/or agonists or antagonists of the invention could be used to treat blood coagulation disorders (e.g., afibrinogenemia, factor deficiencies), blood platelet disorders (e.g. thrombocytopenia), or wounds resulting from trauma, surgery, or other causes. Alternatively, PGRP-L polypeptides, antibodies, or polynucleotides of the invention, and/or agonists or antagonists of the invention, that can decrease hemostatic or thrombolytic activity could be used to inhibit or dissolve clotting, important in the treatment of heart attacks (infarction), strokes, or scarring.

PGRP-L polypeptides, antibodies, polynucleotides and/or agonists or antagonists can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, PGRP-L polypeptides, antibodies, polypeptides and/or agonists or antagonists may also directly inhibit the infectious agent (refer to section of application listing infectious agents, etc), without necessarily eliciting an immune response.

Additional preferred embodiments of the invention include, but are not limited to, the use of PGRP-L polypeptides, antibodies, polynucleotides and/or agonists or antagonists in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

A vaccine adjuvant that enhances immune responsiveness to specific antigen.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacterium or fungus, disease, or symptom selected from the group consisting of: tetanus, Diphtheria, botulism, and meningitis type B. In another specific embodiment, the compositions of the invention are used as an adjuvant to enhance an immune response to a bacterium or fungus, disease, or symptom selected from the group consisting of: *Vibrio cholerae, Mycobacterium leprae, Salmonella typhi, Salmonella paratyphi, Neisseria meningitidis, Streptococcus pneumoniae,* Group B streptococcus, *Shigella* spp., Enterotoxigenic *Escherichia coli,* Enterohemorrhagic *E. coli, Borrelia burgdorferi,* and *Plasmodium* spp. (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria).

As a stimulator of B cell responsiveness to pathogens.

As an activator of T cells.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell and/or T cell immunodeficient individuals. T cell deficiencies that may be ameliorated or treated by administering the PGRP-L polypeptides (e.g., PGRP-L-Fc fusion proteins containing PGRP-L polypeptides of interest, and agonistic or antagonistic anti-PGRP-L antibodies) or polynucleotides of the invention, or antagonists or agonists thereof include, but are not limited to, for example, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are ameliorated or treated by administering the PGRP-L polypeptides (e.g., PGRP-L-Fc fusion proteins containing PGRP-L polypeptides of interest, and agonistic or antagonistic anti-PGRP-L antibodies) or polynucleotides of the invention, or antagonists or agonists thereof.

Other immunodeficiencies that may be ameliorated or treated by administering the PGRP-L polypeptides ((e.g., PGRP-L-Fc fusion proteins containing PGRP-L polypeptides of interest, and agonistic or antagonistic anti-PGRP-L antibodies) or polynucleotides of the invention, or agonists or antagonists thereof, include, but are not limited to, severe combined immunodeficiency (SCID; e.g., X-linked SCID, autosomal SCID, and adenosine deaminase deficiency), ataxia-telangiectasia, Wiskott-Aldrich syndrome, short-limber dwarfism, X-linked lymphoproliferative syndrome (XLP), Nezelof syndrome (e.g., purine nucleoside phosphorylase deficiency), MHC Class II deficiency. In specific embodiments, ataxia-telangiectasia or conditions associated with ataxia-telangiectasia are ameliorated or treated by administering the PGRP-L polypeptides (e.g., PGRP-L-Fc fusion proteins containing PGRP-L polypeptides of interest, and agonistic or antagonistic anti-PGRP-L antibodies) or polynucleotides of the invention, or antagonists or agonists thereof.

As an agent to boost immunoresponsiveness among individuals having an acquired loss of B cell function. Conditions resulting in an acquired loss of B cell function that may be ameliorated or treated by administering the PGRP-L polypeptides, antibodies, polynucleotides and/or agonists or antagonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the PGRP-L polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, PGRP-L (in soluble, membrane-bound or transmembrane forms) enhances antigen presentation or antagonizes antigen presentation in vitro or in vivo. Moreover, in related embodiments, said enhancement or antagonization of antigen presentation may be useful as an anti-tumor treatment or to modulate the immune system.

As an agent to direct an individuals immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a stimulator of B cell production in pathologies such as AIDS, chronic lymphocyte disorder and/or Common Variable Immunodeficiency.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance PGRP-L mediated responses.

As a means of activating T cells.

As a means of activating monocytes/macrophages to defend against parasitic diseases that effect monocytes such as Leishmaniasis.

As pretreatment of bone marrow samples prior to transplant. Such treatment would increase B cell representation and thus accelerate recover.

As a means of regulating secreted cytokines that are elicited by PGRP-L polypeptides.

PGRP-L polypeptides or polynucleotides of the invention, or agonists may be used to modulate IgE concentrations in vitro or in vivo.

Additionally, PGRP-L polypeptides or polynucleotides of the invention, or agonists thereof, may be used to treat or prevent IgE-mediated allergic reactions. Such allergic reactions include, but are not limited to, asthma, rhinitis, and eczema.

All of the above described applications as they may apply to veterinary medicine.

Antagonists of PGRP-L include binding and/or inhibitory antibodies, antisense nucleic acids, ribozymes or soluble forms of the PGRP-L receptor(s) (e.g., a PGRP-L-Fc fusion protein) (see e.g., Example 9). These would be expected to reverse many of the activities of the ligand described above as well as find clinical or practical application as:

A means of blocking various aspects of immune responses to foreign agents or self. Examples include autoimmune disorders such as lupus, and arthritis, as well as immuno-responsiveness to skin allergies, inflammation, bowel disease, injury and pathogens. Although our current data speaks directly to the potential role of PGRP-L in B cell and T cell related pathologies, it remains possible that other cell types may gain expression or responsiveness to TR2. Thus, PGRP-L may, like CD40 and its ligand, be regulated by the status of the immune system and the microenvironment in which the cell is located.

A therapy for preventing the B cell proliferation and Ig secretion associated with autoimmune diseases such as idiopathic thrombocytopenic purpura, systemic lupus erythematosus and MS.

An inhibitor of B and/or T cell migration in endothelial cells. This activity disrupts tissue architecture or cognate responses and is useful, for example in disrupting immune responses, and blocking sepsis.

An inhibitor of graft versus host disease or transplant rejection.

A therapy for B cell and/or T cell malignancies such as ALL, Hodgkins disease, non-Hodgkin's lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

PGRP-L polypeptides, antibodies, or polynucleotides of the invention, and/or agonists or antagonists may be used to modulate IgE concentrations in vitro or in vivo.

In another embodiment, administration of PGRP-L polypeptides, antibodies, polynucleotides and/or agonists or antagonists of the invention, may be used to treat or prevent IgE-mediated allergic reactions including, but not limited to, asthma, rhinitis, and eczema.

An inhibitor of signaling pathways involving ERK1, COX2 and Cyclin D2 which have been associated with PGRP-L polypeptide induced B cell activation.

The agonists and antagonists may be employed in a composition with a pharmaceutically acceptable carrier, e.g., as described above.

The antagonists may be employed for instance to inhibit PGRP-L polypeptide chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the PGRP-L polypeptides of the present invention. The antagonists may also be employed for treating atherosclerosis, by preventing monocyte infiltration in the artery wall. The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by PGRP-L polypeptides. The antagonists may also be employed to treat cases of bone marrow failure, for example, aplastic anemia and myelodysplastic syndrome. The antagonists may also be employed to treat asthma and allergy by preventing eosinophil accumulation in the lung. The antagonists may also be employed to treat subepithelial basement membrane fibrosis which is a prominent feature of the asthmatic lung.

Antibodies against PGRP-L polypeptides may be employed to bind to and inhibit PGRP-L activity to treat ARDS, by preventing infiltration of neutrophils into the lung after injury. The antagonists and antagonists of the instant may be employed in a composition with a pharmaceutically acceptable carrier, e.g., as described hereinafter.

Agonists and antagonist of the invention also have uses in stimulating wound and tissue repair, stimulating angiogenesis, stimulating the repair of vascular or lymphatic diseases or disorders. Additionally, agonists and antagonists of the invention may be used to stimulate the regeneration of mucosal surfaces.

Moreover, PGRP-L polynucleotides or polypeptides, or agonists or antagonists of PGRP-L polynucleotides or polypeptides, can also be used to modulate hemostatic (the stopping of bleeding) or thrombolytic activity (clot formation). For example, by increasing hemostatic or thrombolytic activity, PGRP-L polynucleotides or polypeptides, or agonists or antagonists of PGRP-L polynucleotides or polypeptides, could be used to treat blood coagulation disorders (e.g., afibrinogenemia, factor deficiencies), blood platelet disorders (e.g. thrombocytopenia), or wounds resulting from trauma, surgery, or other causes. Alternatively, PGRP-L polynucleotides or polypeptides, or agonists or antagonists of PGRP-L polynucleotides or polypeptides, that can decrease hemostatic or thrombolytic activity could be used to inhibit or dissolve clotting, important in the treatment of heart attacks (infarction), strokes, or scarring.

PGRP-L polynucleotides or polypeptides, or agonists or antagonists of PGRP-L polynucleotides or polypeptides, may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of PGRP-L polynucleotides or polypeptides, or agonists or antagonists of PGRP-L polynucleotides or polypeptides, that can inhibit an immune response, particularly the proliferation, differentiation, or chemotaxis of T-cells, may be an effective therapy in preventing autoimmune disorders.

In another embodiment, PGRP-L polynucleotides or polypeptides or PGRP-L antagonists (e.g., anti-PGRP-L antibodies) of the invention are used to treat, diagnose and/or prognose an individual having common variable immunodeficiency disease ("CVID"; also known as "acquired agammaglobulinemia" and "acquired hypogammaglobulinemia") or a subset of this disease. According to this embodiment, an individual having CVID or a subset of individuals having CVID expresses aberrant levels of PGRP-L receptor on their T cells, when compared to individuals not having CVID. Any means described herein or otherwise known in the art may be applied to detect PGRP-L receptor polynucleotides or polypeptides of the invention (e.g., FACS analysis or ELISA detection of PGRP-L polypeptides of the invention and hybridization or PCR detection of PGRP-L polynucleotides of the invention) and to determine differentially the expression profile of PGRP-L polynucleotides or polypeptides of the invention in a sample containing at least T cells or some component thereof (e.g., RNA) as compared to a sample containing at least B cells or a component thereof (e.g., RNA). In the instance where a sample containing at least T cells or some component thereof (e.g., RNA) is determined to reflect PGRP-L polynucleotide or polypeptide expression and a sample containing at least B cells or a component thereof (e.g., RNA) is determined to reflect less than normal levels of PGRP-L receptor polynucleotide or polypeptide expression, the samples may be correlated with the occurrence of CVID (i.e., "acquired agammaglobulinemia" or "acquired hypogammaglobulinemia").

A subject of persons afflicted with CVID may be characterized by high levels of expression of both PGRP-L polypeptides in peripheral or circulating T cells when compared to that observed in individuals not having CVID. In contrast, persons who are not afflicted with CVID may typically be characterized by low levels of PGRP-L polypeptide expression. Thus, PGRP-L polynucleotides and/or polypeptides of the invention, and/or agonists or antagonists thereof, may be used according to the methods of the invention in the differential diagnosis of this subset of CVID. For example, a sample of peripheral T cells obtained from a person suspected of being afflicted with CVID ("the subject") may be analyzed for the relative expression level (s) of PGRP-L polynucleotides and/or polypeptides of the invention. The expression level(s) of one or more of these molecules of the invention is (are) then compared to the expression level(s) of the same molecules of the invention as expressed in a person known not to be afflicted with CVID ("the control"). A significant difference in expression level (s) of PGRP-L polynucleotides and/or polypeptides of the invention, and/or agonists and/or antagonists thereof, between samples obtained from the subject and the control suggests that the subject is afflicted with this subset of CVID.

In a specific embodiment, PGRP-L polynucleotides or polypeptides, or agonists thereof (e.g., anti-PGRP-L antibodies) are used to treat or prevent a disorder characterized by deficient serum immunoglobulin production, recurrent infections, and/or immune system dysfunction. Moreover, PGRP-L polynucleotides or polypeptides, or agonists thereof (e.g., anti-PGRP-L antibodies) may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or *Pneumocystis carnii*.

In another embodiment, PGRP-L polynucleotides or polypeptides or PGRP-L antagonists (e.g., anti-PGRP-L antibodies) of the invention are used to treat, diagnose, or prognose an individual having an autoimmune disease or disorder. According to this embodiment, an individual having an autoimmune disease or disorder expresses aberrantly high levels of PGRP-L when compared to an individual not having an autoimmune disease or disorder. Any means described herein or otherwise known in the art may be applied to detect PGRP-L polynucleotides or polypeptides of the invention (e.g., FACS analysis or ELISA detection of PGRP-L polypeptides of the invention and hybridization or PCR detection of PGRP-L polynucleotides of the invention) and to determine the expression profile of PGRP-L polynucleotides and/or polypeptides of the invention in a biological sample.

PGRP-L polynucleotides or polypeptides, or agonists or antagonists of PGRP-L polynucleotides or polypeptides, can be used in assays to test for one or more biological activities. If PGRP-L polynucleotides or polypeptides, or agonists or antagonists of PGRP-L polynucleotides or polypeptides, do exhibit activity in a particular assay, it is likely that PGRP-L polynucleotides or polypeptides may be involved in the diseases associated with the biological activity. Therefore, PGRP-L polynucleotides or polypeptides could be used to treat the associated disease.

In a specific embodiment, PGRP-L polynucleotides or polypeptides, or agonists or antagonists of PGRP-L polynucleotides or polypeptides may be used to treat, diagnose, prevent, and/or prognose acute myelogenous leukemia. In a preferred embodiment, PGRP-L polynucleotides or polypeptides, or agonists or antagonists of PGRP-L polynucleotides or polypeptides conjugated to a toxin or a radioactive isotope, as described herein, may be used to treat, diagnose, prevent, and/or prognose acute myelogenous leukemia. In a further preferred embodiment, PGRP-L polynucleotides or polypeptides, or agonists or antagonists of PGRP-L polynucleotides or polypeptides conjugated to a toxin or a radioactive isotope, as described herein, may be used to treat, diagnose, prevent, and/or prognose chronic myelogenous leukemia, multiple myeloma, non-Hodgkin's lymphoma, and/or Hodgkin's disease.

In another specific embodiment, PGRP-L polynucleotides or polypeptides, or agonists or antagonists of PGRP-L polynucleotides or polypeptides may be used to treat, diagnose, prognose, and/or prevent T cell deficiencies. T cell deficiencies include, but are not limited to, for example, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity.

In another specific embodiment, PGRP-L polynucleotides or polypeptides, or agonists or antagonists of PGRP-L polynucleotides or polypeptides may be used to treat, diagnose, prognose, and/or prevent selective IgA deficiency, myeloperoxidase deficiency, C2 deficiency, ataxia-telangiectasia, DiGeorge anomaly, common variable immunodeficiency (CVI), X-linked agammaglobulinemia, severe combined immunodeficiency (SCID), chronic granulomatous disease (CGD), and Wiskott-Aldrich syndrome.

Examples of autoimmune disorders that can be treated or detected include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Additional autoimmune disorders (that are highly probable) that may be treated, prevented, and/or diagnosed with the compositions of the invention include, but are not limited to, autoimmune thyroiditis (i.e., Hashimoto's thyroiditis) (often characterized, e.g., by cell-mediated and humoral thyroid cytotoxicity), systemic lupus erythematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders (that are probable) that may be treated, prevented, and/or diagnosed with the compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes mellitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using PGRP-L antibodies and/or anti-PGRP-L antibodies and/or a soluble PGRP-L polypeptide of the invention.

Similarly, allergic reactions and conditions, such as asthma (particularly allergic asthma) or other respiratory problems, may also be treated by PGRP-L polynucleotides or polypeptides, or agonists or antagonists of PGRP-L polynucleotides or polypeptides. Moreover, these molecules can be used to treat anaphylaxis, hypersensitivity to an antigenic molecule, or blood group incompatibility.

In specific embodiments, PGRP-L antibodies and/or anti-PGRP-L antibodies and/or soluble PGRP-L polypeptides of the invention are useful to treat, diagnose, prevent, and/or prognose autoimmune and inflammatory diseases, transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE).

Moreover, inflammatory conditions may also be treated, diagnosed, prevented and/or prognosed with PGRP-L polynucleotides or polypeptides, or agonists or antagonists of PGRP-L polynucleotides or polypeptides (e.g., anti-PGRP-L antibodies) of the invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease, AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosis, diabetes mellitus (i.e., type 1 diabetes), and allogenic transplant rejection).

PGRP-L polynucleotides or polypeptides, or agonists or antagonists of PGRP-L polynucleotides or polypeptides, may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of PGRP-L polynucleotides or polypeptides, or agonists or antagonists of PGRP-L polynucleotides or polypeptides, that inhibits an immune response, particularly the proliferation, differentiation, or chemotaxis of T-cells, maybe an effective therapy in preventing organ rejection or GVHD.

Similarly, PGRP-L polynucleotides or polypeptides, or agonists or antagonists of PGRP-L polynucleotides or polypeptides, may also be used to modulate inflammation. For example, PGRP-L polynucleotides or polypeptides, or agonists or antagonists of PGRP-L polynucleotides or polypeptides, may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1).

In specific embodiments, the compositions of the invention are used as an adjuvant to enhance an immune response to a parasite. In another specific embodiment, the compositions of the invention are used as an adjuvant to enhance an immune response to Plasmodium (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell immunodeficient individuals, such as, for example, an individual who has undergone a partial or complete splenectomy. B cell immunodeficiencies that may be ameliorated or treated by administering the PGRP-L polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVI) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymophoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

Anti-Angiogenesis Activity

The naturally occurring balance between endogenous stimulators and inhibitors of angiogenesis is one in which inhibitory influences predominate. Rastinejad et al., Cell 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al, Biotech. 9:630–634 (1991); Folkman et al., N. Engl. J. Med., 333:1757–1763 (1995); Auerbach et al., J. Microvasc. Res. 29:401–411 (1985); Folkman, Advances in Cancer Research, eds. Klein and Weinhouse, Academic Press, New York, pp. 175–203 (1985); Patz, Am. J. Opthalmol. 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, Science 235:442–447 (1987).

The present invention provides for treatment of diseases or disorders associated with neovascularization by administration of the PGRP-L polynucleotides and/or polypeptides of the invention, as well as agonists or antagonists of PGRP-L. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)):

Ocular disorders associated with neovascularization which can be treated with the PGRP-L polynucleotides and polypeptides of the present invention (including PGRP-L agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704–710 (1978) and Gartner et al., Surv. Ophthal. 22:291–312 (1978).

Additionally, disorders which can be treated with the PGRP-L polynucleotides and polypeptides of the present invention (including PGRP-L agonist and/or antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with be treated with the PGRP-L polynucleotides and polypeptides of the present invention (including PGRP-L agonist and/or antagonists) include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uveitis, delayed wound healing, endometriosis, vasculogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (*Helicobacter pylori*), Bartonellosis and bacillary angiomatosis.

Wound Healing and Epithelial Cell Proliferation

In accordance with yet a further aspect of the present invention, there is provided a process for utilizing PGRP-L polynucleotides or polypeptides, as well as agonists or antagonists of PGRP-L, for therapeutic purposes, for example, to stimulate epithelial cell proliferation and basal keratinocytes for the purpose of wound healing, and to stimulate hair follicle production and healing of dermal wounds. PGRP-L polynucleotides or polypeptides, as well as agonists or antagonists of PGRP-L, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. PGRP-L polynucleotides or polypeptides, as well as agonists or antagonists of PGRP-L, could be used to promote dermal reestablishment subsequent to dermal loss.

PGRP-L polynucleotides or polypeptides, as well as agonists or antagonists of PGRP-L, could be used to increase the adherence of skin grafts to a wound bed and to stimulate re-epithelialization from the wound bed. The following are types of grafts that PGRP-L polynucleotides or polypeptides, agonists or antagonists of PGRP-L, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. PGRP-L polynucleotides or polypeptides, as well as agonists or antagonists of PGRP-L, can be used to promote skin strength and to improve the appearance of aged skin.

It is believed that PGRP-L polynucleotides or polypeptides, as well as agonists or antagonists of PGRP-L, will also produce changes in hepatocyte proliferation, and epithelial cell proliferation in the lung, breast, pancreas, stomach, small intestine, and large intestine. PGRP-L polynucleotides or polypeptides, as well as agonists or antagonists of PGRP-L, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. PGRP-L polynucleotides or polypeptides, agonists or antagonists of PGRP-L, may promote proliferation of endothelial cells, keratinocytes, and basal keratinocytes.

PGRP-L polynucleotides or polypeptides, as well as agonists or antagonists of PGRP-L, could also be used to reduce the side effects of gut toxicity that result from radiation, chemotherapy treatments or viral infections. PGRP-L polynucleotides or polypeptides, as well as agonists or antagonists of PGRP-L, may have a cytoprotective effect on the small intestine mucosa. PGRP-L polynucleotides or polypeptides, as well as agonists or antagonists of PGRP-L, may also stimulate healing of mucositis (mouth ulcers) that result from chemotherapy and viral infections.

PGRP-L polynucleotides or polypeptides, as well as agonists or antagonists of PGRP-L, could further be used in full regeneration of skin in full and partial thickness skin defects, including burns, (i.e., repopulation of hair follicles, sweat glands, and sebaceous glands), treatment of other skin defects such as psoriasis. PGRP-L polynucleotides or polypeptides, as well as agonists or antagonists of PGRP-L, could be used to treat epidermolysis bullosa, a defect in adherence of the epidermis to the underlying dermis which results in frequent, open and painful blisters by accelerating reepithelialization of these lesions. PGRP-L polynucleotides or polypeptides, as well as agonists or antagonists of PGRP-L, could also be used to treat gastric and doudenal ulcers and help heal by scar formation of the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, PGRP-L polynucleotides or polypeptides, as well as agonists or antagonists of PGRP-L, could be used to promote the resurfacing of the mucosal surface to aid more rapid healing and to prevent progression of inflammatory bowel disease. Treatment with PGRP-L polynucleotides or polypeptides, agonists or antagonists of PGRP-L, is expected to have a significant effect on the production of mucus throughout the gastrointestinal tract and could be used to protect the intestinal mucosa from injurious substances that are ingested or following surgery. PGRP-L polynucleotides or polypeptides, as well as agonists or antagonists of PGRP-L, could be used to treat diseases associate with the under expression of PGRP-L.

Moreover, PGRP-L polynucleotides or polypeptides, as well as agonists or antagonists of PGRP-L, could be used to prevent and heal damage to the lungs due to various pathological states. A growth factor such as PGRP-L polynucleotides or polypeptides, as well as agonists or antagonists of PGRP-L, which could stimulate proliferation and differentiation and promote the repair of alveoli and bronchiolar epithelium to prevent or treat acute or chronic lung damage. For example, emphysema, which results in the progressive loss of alveoli, and inhalation injuries, i.e., resulting from smoke inhalation and burns, that cause necrosis of the bronchiolar epithelium and alveoli could be effectively treated using PGRP-L polynucleotides or polypeptides, agonists or antagonists of PGRP-L. Also, PGRP-L polynucleotides or polypeptides, as well as agonists or antagonists of PGRP-L, could be used to stimulate the proliferation of and differentiation of type II pneumocytes, which may help treat or prevent disease such as hyaline membrane diseases, such as infant respiratory distress syndrome and bronchopulmonary dysplasia, in premature infants.

PGRP-L polynucleotides or polypeptides, as well as agonists or antagonists of PGRP-L, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetracholoride and other hepatotoxins known in the art).

In addition, PGRP-L polynucleotides or polypeptides, as well as agonists or antagonists of PGRP-L, could be used treat or prevent the onset of diabetes mellitus. In patients with newly diagnosed Types I and II diabetes, where some islet cell function remains, PGRP-L polynucleotides or polypeptides, as well as agonists or antagonists of PGRP-L, could be used to maintain the islet function so as to alleviate, delay or prevent permanent manifestation of the disease.

Also, PGRP-L polynucleotides or polypeptides, as well as agonists or antagonists of PGRP-L, could be used as an auxiliary in islet cell transplantation to improve or promote islet cell function.

Regeneration

PGRP-L polynucleotides or polypeptides, or agonists or antagonists of PGRP-L, can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteoarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, PGRP-L polynucleotides or polypeptides, or agonists or antagonists of PGRP-L, may increase regeneration of tissues difficult to heal. For example, increased tendon/ligament regeneration would quicken recovery time after damage. PGRP-L polynucleotides or polypeptides, or agonists or antagonists of PGRP-L, of the present invention could also be used prophylactically in an effort to avoid damage. Specific diseases that could be treated include of tendonitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using PGRP-L polynucleotides or polypeptides, or agonists or antagonists of PGRP-L, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the PGRP-L polynucleotides or polypeptides, or agonists or antagonists of PGRP-L.

Chemotaxis

PGRP-L polynucleotides or polypeptides, or agonists or antagonists of PGRP-L, may have chemotaxis activity. A chemotactic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

PGRP-L polynucleotides or polypeptides, or agonists or antagonists of PGRP-L, may increase chemotactic activity of particular cells. These chemotactic molecules can then be used to treat inflammation, infection, hyperproliferative disorders, or any immune system disorder by increasing the number of cells targeted to a particular location in the body. For example, chemotactic molecules can be used to treat wounds and other trauma to tissues by attracting immune cells to the injured location. As a chemotactic molecule, PGRP-L could also attract fibroblasts, which can be used to treat wounds.

It is also contemplated that PGRP-L polynucleotides or polypeptides, or agonists or antagonists of PGRP-L, may inhibit chemotactic activity. These molecules could also be used to treat disorders. Thus, PGRP-L polynucleotides or polypeptides, or agonists or antagonists of PGRP-L, could be used as an inhibitor of chemotaxis.

Binding Activity

PGRP-L polypeptides may be used to screen for molecules that bind to PGRP-L or for molecules to which PGRP-L binds. The binding of PGRP-L and the molecule may activate (agonist), increase, inhibit (antagonist), or decrease activity of the PGRP-L or the molecule bound. Examples of such molecules include antibodies, oligonucleotides, proteins (e.g., receptors), or small molecules.

Preferably, the molecule is closely related to the natural ligand of PGRP-L, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which PGRP-L binds, or at least, a fragment of the receptor capable of being bound by PGRP-L (e.g., active site). In either case, the molecule can be rationally designed using known techniques.

Preferably, the screening for these molecules involves producing appropriate cells which express PGRP-L, either as a secreted protein or on the cell membrane. Preferred cells include cells from mammals, yeast, *Drosophila*, or *E. coli*. Cells expressing PGRP-L (or cell membrane containing the expressed polypeptide) are then preferably contacted with a test compound potentially containing the molecule to observe binding, stimulation, or inhibition of activity of either PGRP-L or the molecule.

The assay may simply test binding of a candidate compound to PGRP-L, wherein binding is detected by a label, or in an assay involving competition with a labeled competitor. Further, the assay may test whether the candidate compound results in a signal generated by binding to PGRP-L.

Alternatively the assay can be carried out using cell-free preparations, polypeptide/molecule affixed to a solid support, chemical libraries, or natural product mixtures. The assay may also simply comprise the steps of mixing a candidate compound with a solution containing PGRP-L, measuring PGRP-L/molecule activity or binding, and comparing the PGRP-L/molecule activity or binding to a standard.

Preferably, an ELISA assay can measure PGRP-L level or activity in a sample (e.g., biological sample) using a monoclonal or polyclonal antibody. The antibody can measure PGRP-L level or activity by either binding, directly or indirectly, to PGRP-L or by competing with PGRP-L for a substrate.

Additionally, the receptor to which PGRP-L binds can be identified by numerous methods known to those of skill in the art, for example, ligand panning and FACS sorting (Coligan, et al., Current Protocols Immun. 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of PGRP-L thereby effectively generating agonists and antagonists of PGRP-L. See generally, U.S. Pat. Nos. 5,605,793, 5,811,238, 5,830, 721, 5,834,252, and 5,837,458, and Patten, P. A., et al., *Curr. Opinion Biotechnol.* 8:724–33 (1997); Harayama, S. *Trends Biotechnol.* 16(2):76–82 (1998); Hansson, L. O., et al., *J. Mol. Biol.* 287:265–76 (1999); and Lorenzo, M. M. and Blasco, R. *Biotechniques* 24(2):308–13 (1998) (each of these patents and publications are hereby incorporated by reference). In one embodiment, alteration of PGRP-L polynucleotides and corresponding polypeptides may be achieved by DNA shuffling. DNA shuffling involves the assembly of two or more DNA segments into a desired PGRP-L molecule by homologous, or site-specific, recombination. In another embodiment, PGRP-L polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of PGRP-L may be recombined with one or more components, motifs, sections, parts, domains, fragments, etc. of one or more heterologous molecules. In preferred embodiments, the heterologous molecules are PGRP-L family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic (dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active PGRP-L fragments. Biologically active fragments are those exhibiting activity similar, but not necessarily identical, to an activity of the PGRP-L polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3$[H] thymidine in each case. The amount of fibroblast cell proliferation is measured by liquid scintillation chromatography which measures the incorporation of $^3$[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the PGRP-L receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the PGRP-L/molecule. Moreover, the assays can discover agents which may inhibit or enhance the production of PGRP-L from suitably manipulated cells or tissues.

Therefore, the invention includes a method of identifying compounds which bind to PGRP-L comprising the steps of: (a) incubating a candidate binding compound with PGRP-L; and (b) determining if binding has occurred. Moreover, the invention includes a method of identifying agonists/antagonists comprising the steps of: (a) incubating a candidate compound with PGRP-L, (b) assaying a biological activity, and (b) determining if a biological activity of PGRP-L has been altered.

Antisense and Ribozyme (Antagonists)

In specific embodiments, antagonists according to the present invention are nucleic acids corresponding to the sequences contained in SEQ ID NO:1, or the complementary strand thereof, and/or to nucleotide sequences contained in the deposited clone HPJEV37. In one embodiment, antisense sequence is generated internally by the organism, in another embodiment, the antisense sequence is separately administered (see, for example, O'Connor, J., Neurochem. 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the PGRP-L antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the PGRP-L antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding PGRP-L, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a PGRP-L gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded PGRP-L antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a PGRP-L RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of PGRP-L shown in FIGS. 1A–B could be used in an antisense approach to inhibit translation of endogenous PGRP-L mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of PGRP-L mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the PGRP-L coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site-specific recognition sequences can be used to destroy PGRP-L mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of PGRP-L (FIGS. 1A–B). Preferably, the ribozyme is engineered so that the cleavage recognition site is located near the 5' end of the PGRP-L mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells which express PGRP-L in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous PGRP-L messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to treat the diseases described herein.

Other Activities

Cells which express the human PGRP-L polypeptides are believed to have a potent cellular response to infection include, for example, liver tissue, and tissues of the immune, and endocrine systems. Furthermore, Thus, it is believed that certain tissues in mammals with certain diseases and infections (e.g., bacterial infection of immuno-compromised individuals), diseases associated with increased or decreased cell survival, secretion, activation, migration, differentiation, and proliferation; diseases associated with the defects of liver cell proliferation and function, cellular immunity, immune dysfunction, and endocrine dysfunction; express significantly altered (e.g., enhanced or decreased) levels of the PGRP-L polypeptide(s) and mRNA encoding the PGRP-L polypeptide(s) when compared to a corresponding "standard" mammal, i.e., a mammal of the same species not having the disease. Diseases associated with defects in the proliferation and/or function of liver tissues, include, for example, hepatomas, hepatoblastoma, jaundice, hepatitis, liver metabolic diseases and conditions that are attributable to the differentiation of hepatocyte progenitor cells. Diseases associated with immune dysfunction and decreased cellular immunity include, for example, bacterial infections (e.g., cutaneous infection due to *Mycobacterium gordonae* in an AIDS patient) and diseases associated with bacterial infection of the skin (e.g., boils, cellulitis, erysipelas, impetigo). Further, it is believed that altered levels of PGRP-L polypeptide can be detected in certain body fluids (e.g., lymph, sera, plasma, urine, and spinal fluid) from mammals with the disorder when compared to sera from mammals of the same species not having the disorder. Thus, the invention provides a diagnostic method useful during diagnosis, which involves assaying the expression level of the gene encoding the PGRP-L polypeptide(s) in mammalian cells or body fluid and comparing the gene expression level with a standard PGRP-L gene expression level, whereby an increase or decrease in the gene expression level over the standard is indicative of the disease.

By "assaying" the expression level of the gene encoding the "PGRP-L polypeptide" is intended qualitatively or quantitatively measuring or estimating the level of the PGRP-L polypeptide(s) or the level of the mRNA encoding the PGRP-L polypeptide(s) in a first biological sample either directly (e.g., by determining or estimating absolute polypeptide or mRNA level) or relatively (e.g., by comparing to the PGRP-L polypeptide(s) level or mRNA level in a second biological sample). Preferably, the PGRP-L protein level or mRNA level in the first biological sample is measured or estimated and compared to a standard PGRP-L protein level or mRNA level, the standard being taken from a second biological sample obtained from an individual not having the disease state. As will be appreciated in the art, once a standard PGRP-L protein level or mRNA level is known, it can be used repeatedly as a standard for comparison.

By "biological sample" is intended any biological sample obtained from an individual, cell line, tissue culture, or other source which contains PGRP-L protein or mRNA. Biological samples include mammalian body fluids (such as lymph, sera, plasma, urine, synovial fluid and spinal fluid), and liver tissue, and other tissues. Methods for obtaining tissue biopsies and body fluids from mammals are well known in the art. Where the biological sample is to include mRNA, a tissue biopsy is the preferred source. Where a diagnosis has already been made according to conventional methods, the present invention is useful as a prognostic indicator, whereby patients exhibiting altered PGRP-L gene expression will experience a worse clinical outcome relative to patients expressing the gene at a normal level. Nucleic acids for diagnosis may be obtained from a biological sample of a subject, such as from blood, urine, saliva, tissue biopsy or autopsy material, using techniques known in the art. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled PGRP-L nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers et al., Science 230:1242 (1985)). Sequence changes at specific locations may also be revealed by nuclease protection assays, such as RNase and S1 protection or the chemical cleavage method (see Cotton et al., Proc. Natl. Acad. Sci. USA 85:4397–4401 (1985)). In another embodiment, an array of oligonucleotide probes comprising PGRP-L polynucleotide sequences or fragments thereof, can be constructed to conduct efficient screening of e.g., genetic mutations. Array technology methods are well known and have general applicability and can be used to address a variety of questions in molecular genetics including gene expression, genetic linkage, and genetic variability (see e.g., Chee et al., Science 274:610–613 (1996)). The diagnostic assays offer a process for diagnosing or determining a susceptibility to specific diseases through detection of mutations in the PGRP-L gene(s) by the methods described herein or otherwise known in the art.

In addition, specific diseases can be diagnosed by methods comprising determining from a sample derived from a subject an abnormally decreased or increased level of PGRP-L polypeptide(s) or mRNA. Decreased or increased expression can be measured at the RNA level using any of the methods well known in the art, which include, but are not limited to, Northern blot analysis, (Harada et al., Cell 63:303–312 (1990)), S1 nuclease mapping (Fijita et al., Cell 49:357–367 (1987)), RNAse protection, the polymerase chain reaction (PCR), reverse transcription in combination with the polymerase chain reaction (RT-PCR) (Makino et al., Technique 2:295–301 (1990), reverse transcription in combination with the ligase chain reaction (RT-LCR) and other hybridization methods.

Assaying PGRP-L polypeptide levels in a biological sample can be by any techniques known in the art, which include, but are not limited to, radioimmunoassays, competitive-binding assays, Western Blot analysis and enzyme linked immunosorbent assays (ELISAs) and other antibody-based techniques. For example, PGRP-L polypeptide expression in tissues can be studied with classical immunohistological methods (Jalkanen et al., J. Cell. Biol. 101:976–985 (1985); Jalkanen et al., J. Cell. Biol. 105:3087–3096 (1987)). Suitable labels are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin. The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptides may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat and prevent neuronal damage which occurs in certain neuronal disorders or neurodegenerative conditions such as Alzheimer's disease, Parkinson's disease, and AIDS-related complex. PGRP-L may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The PGRP-L polypeptide may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The PGRP-L polypeptide may also be employed to maintain organs before transplantation or for supporting cell culture of primary tissues.

The polypeptide of the present invention may also be employed for inducing tissue of mesodermal origin to differentiate in early embryos.

PGRP-L polynucleotides or polypeptides, or agonists or antagonists of PGRP-L, may also increase or decrease the differentiation or proliferation of embryonic stem cells, besides, as discussed above, hematopoietic lineage.

PGRP-L polynucleotides or polypeptides, or agonists or antagonists of PGRP-L, may also be used to modulate mammalian characteristics, such as body height, weight, hair color, eye color, skin, percentage of adipose tissue, pigmentation, size, and shape (e.g., cosmetic surgery). Similarly, PGRP-L polynucleotides or polypeptides, or agonists or antagonists of PGRP-L, may be used to modulate mammalian metabolism affecting catabolism, anabolism, processing, utilization, and storage of energy.

PGRP-L polynucleotides or polypeptides, or agonists or antagonists of PGRP-L, may be used to change a mammal's mental state or physical state by influencing biorhythms, circadian rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

PGRP-L polynucleotides or polypeptides, or agonists or antagonists of PGRP-L, may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

Having generally described the invention, the same will be more readily understood by reference to the following examples, which are provided by way of illustration and are not intended as limiting.

EXAMPLES

Example 1

Isolation of the PGRP-L cDNA Clone from the Deposited Sample

The cDNA for PGRP-L is inserted into the EcoRI/XhoI multiple cloning site of pBluescript. (Stratagene, La Jolla, Calif.) pBluescript contains an ampicillin resistance gene and may be transformed into *E. coli* strain DH10B, available from Life Technologies. (See, for instance, Gruber, C. E., et al., Focus 15:59- (1993)).

Two approaches can be used to isolate PGRP-L from the deposited sample. First, the deposited clone is transformed into a suitable host (such as XL-1 Blue (Stratagene)) using techniques known to those of skill in the art, such as those provided by the vector supplier or in related publications or patents. The transformants are plated on 1.5% agar plates (containing the appropriate selection agent, e.g., ampicillin) to a density of about 150 transformants (colonies) per plate. A single colony is then used to generate DNA using nucleic acid isolation techniques well known to those skilled in the art. (e.g., Sambrook et al., Molecular Cloning: A Laboratory Manual, 2nd Edit., (1989), Cold Spring Harbor Laboratory Press).

Alternatively, two primers of 17–20 nucleotides derived from both ends of the SEQ ID NO:1 (i.e., within the region of SEQ ID NO:1 bounded by the 5' NT and the 3' NT of the clone) are synthesized and used to amplify the PGRP-L cDNA using the deposited cDNA plasmid as a template. The polymerase chain reaction is carried out under routine conditions, for instance, in 25 μl of reaction mixture with 0.5 ug of the above cDNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of the PGRP-L gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7) :1683–1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the PGRP-L gene of interest is used to PCR amplify the 5' portion of the PGRP-L full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the PGRP-L gene.

Example 2

Isolation of PGRP-L Genomic Clones

A human genomic P1 library (Genomic Systems, Inc.) is screened by PCR using primers selected for the cDNA sequence corresponding to SEQ ID NO:1., according to the method described in Example 1. (See also, Sambrook et al.).

Example 3

Tissue Distribution of PGRP-L Polypeptides

Tissue distribution of mRNA expression of PGRP-L is determined using protocols for Northern blot analysis, described by, among others, Sambrook et al. For example, a PGRP-L probe produced by the method described in Example 1 is labeled with $^{32}P$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70 degree C. overnight, and the films developed according to standard procedures.

Example 4

Chromosomal Mapping of PGRP-L

An oligonucleotide primer set is designed according to the sequence at the 5' end of SEQ ID NO:1. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of PGRP-L

PGRP-L polynucleotide encoding a PGRP-L polypeptide invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Amp$^r$), a bacterial origin of replication (ori), an IPTG-regulatable promoter/operator (P/O), a ribosome binding site (RBS), a 6-histidine tag (6-His), and restriction enzyme cloning sites.

Specifically, to clone the PGRP-L protein of FIG. 1A in a bacterial vector, the 5' primer has the sequence 5' GCAGCA CATATGCGCGGCTGGCACTGGGTG 3' (SEQ ID NO:15) containing the underlined NdeI restriction site followed a number of nucleotides of the amino terminal coding sequence of the PGRP-L sequence in SEQ ID NO:1. One of ordinary skill in the art would appreciate, of course, that the point in the protein coding sequence where the 5' primer begins may be varied to amplify a DNA segment encoding any desired portion of the complete PGRP-L protein shorter than the protein. The 3' primer has the sequence 5' GCAGCAGGTACCTTAGGAGCTGGG GAAAG 3' (SEQ ID NO:16) containing the underlined Asp718 restriction site followed by a number nucleotides complementary to the 3' end of the coding sequence of the PGRP-L DNA sequence of SEQ ID NO:1.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 μg/ml) and Kan (25 μg/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalactopyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified PGRP-L protein is then renatured by dialyzing it against phosphate-buffered saline (PBS) or 50 mM Na-acetate, pH 6 buffer plus 200 mM NaCl. Alternatively, the PGRP-L protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified PGRP-L protein is stored at 4 degree C. or frozen at −80 degree C.

In addition to the above expression vector, the present invention further includes an expression vector comprising phage operator and promoter elements operatively linked to a PGRP-L polynucleotide, called pHE4a. (ATCC Accession Number 209645, deposited Feb. 25, 1998.) This vector contains: 1) a neomycin phosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of PGRP-L Polypeptide from an Inclusion Body

The following alternative method can be used to purify PGRP-L polypeptide expressed in *E coli* when it is present in the form of inclusion bodies. Unless otherwise specified, all of the following steps are conducted at 4–10 degree C.

Upon completion of the production phase of the *E. coli* fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the PGRP-L polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant PGRP-L polypeptide should exhibit greater than 95% purity after the above refolding and purification steps. No major contaminant bands should be observed from Coomassie blue stained 16% SDS-PAGE gel when 5 μg of purified protein is loaded. The purified PGRP-L protein can also be tested for endotoxin/LPS contamination, and typically the LPS content is less than 0.1 ng/ml according to LAL assays.

Example 7

Cloning and Expression of PGRP-L in a Baculovirus Expression System

In this example, the plasmid shuttle vector pA2 is used to insert PGRP-L polynucleotide into a baculovirus to express PGRP-L. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned PGRP-L polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the PGRP-L cDNA sequence contained in the deposited clone, including the AUG initiation codon and any naturally associated leader sequence, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

More specifically, the cDNA sequence encoding the full length PGRP-L protein in the deposited clone, including the AUG initiation codon and the naturally associated leader sequence shown in SEQ ID NO:1, is amplified using PCR oligonucleotide primers corresponding to the 5' and 3' sequences of the gene. The 5' primer has the sequence 5' GCAGCAA GGATCCGCCATCCGCGGCTGGCACTGGGTGGGCGCC 3' (SEQ ID NO:17) containing the BamHI restriction enzyme site, an efficient signal for initiation of translation in eukaryotic cells (Kozak, M., J. Mol. Biol. 196:947–950 (1987)), followed by a number of nucleotides of the sequence of the complete PGRP-L protein shown in FIG. 1, beginning with the AUG initiation codon. The 3' primer has the sequence 5' GCAGCA GGTACCTTAGGAGCTGGGGAAAGGACAGGCTGG 3' (SEQ ID NO:18) containing the KpnI restriction site followed by a number of nucleotides complementary to the 3' noncoding sequence in FIG. 1.

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five μg of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., Proc. Natl. Acad.

Sci. USA 84:7413–7417 (1987). One µg of BaculoGold™ virus DNA and 5 µg of the plasmid are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced PGRP-L protein.

Example 8

Expression of PGRP-L in Mammalian Cells

PGRP-L polypeptide can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2DHFR (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, PGRP-L polypeptide can be expressed in stable cell lines containing the PGRP-L polynucleotide integrated into a chromosome. The co-transfection with a selectable marker such as DHFR, gpt, neomycin, hygromycin allows the identification and isolation of the transfected cells.

The transfected PGRP-L gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-DHFR (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of PGRP-L. The vectors also contain the 3' intron, the polyadenylation and termination signal of the rat pre-pro-insulin gene, and the mouse DHFR gene under control of the SV40 early promoter.

Specifically, the plasmid pC4 is digested with BamHI and KpnI and then dephosphorylated using calf intestinal phosphates by procedures known in the art. The vector is then isolated from a 1% agarose gel.

The cDNA sequence encoding the PGRP-L protein in the deposited clone is amplified using PCR oligonucleotide primers corresponding to the 5' and 3' sequences of the gene. The 5' primer has the sequence 5' GCAGCAA GGATCCGCCATCCGCGGCTGGCACTGGGTGGGC GCC 3' (SEQ ID NO:17) containing the BamHI restriction enzyme site, an efficient signal for initiation of translation in eukaryotic cells (Kozak, M., J. Mol. Biol. 196:947–950 (1987)), followed by a number of nucleotides of the sequence of the complete PGRP-L protein shown in FIG. 1, beginning with the AUG initiation codon. The 3' primer has the sequence 5' GCAGCAGGTACCTTAGGAGCTGGG-GAAAGGACAGGCTGG 3' (SEQ ID NO:18) containing the KpnI restriction site followed by a number of nucleotides complementary to the 3' noncoding sequence in FIG. 1.

If a naturally occurring signal sequence is used to produce a secreted protein, the vector does not need a second signal peptide. Alternatively, if a naturally occurring signal sequence is not used, the vector can be modified to include a heterologous signal sequence in an effort to secrete the protein from the cell. (See, e.g., WO 96/34891.)

The amplified fragment is then digested with the BamHI and KpnI and purified on a 1% agarose gel using a commercially available kit ("Geneclean," BIO 101 Inc., La Jolla, Calif.). The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene is used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of PGRP-L is analyzed, for instance, by SDS-PAGE and Western blot or by reversed phase HPLC analysis.

Example 9

Construction of N-Terminal and/or C-Terminal Deletion Mutants

The following general approach may be used to clone a N-terminal or C-terminal deletion PGRP-L deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired PGRP-L polynucleotide fragment. An initiation and stop codon are added to the 5' and 3' primers respectively, if necessary, to express the PGRP-L polypeptide fragment encoded by the polynucleotide fragment. Preferred PGRP-L polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the PGRP-L polynucleotide fragment in a desired vector may also be added to the 5' and 3' primer sequences. The PGRP-L polynucleotide fragment is amplified from genomic DNA or from the deposited cDNA clone using the appropriate PCR oligonucleotide primers and conditions discussed herein or know in the art. The PGRP-L polypeptide fragments encoded by the PGRP-L polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the PGRP-L polypeptide fragment A-35 to S-174 is amplified and cloned as follows: A 5' primer is generated comprising a restriction enzyme site followed by an initiation codon in frame with the polynucleotide sequence encoding the N-terminal portion of the polypeptide fragment beginning with A-35. A complementary 3' primer is generated comprising a restriction enzyme site followed by a stop codon in frame with the polynucleotide sequence encoding C-terminal portion of the PGRP-L polypeptide fragment ending with S-174.

The amplified polynucleotide fragment and the expression vector are digested with restriction enzymes which recognize the sites in the primers. The digested polynucleotides are then ligated together. The PGRP-L polynucleotide fragment is inserted into the restricted expression vector, preferably in a manner which places the PGRP-L polypeptide fragment coding region downstream from the promoter. The ligation mixture is transformed into competent *E. coli* cells using standard procedures and as described in the Examples herein. Plasmid DNA is isolated from resistant colonies and the identity of the cloned DNA confirmed by restriction analysis, PCR and DNA sequencing.

Example 10

Protein Fusions of PGRP-L

PGRP-L polypeptides are preferably fused to other proteins. These fusion proteins can be used for a variety of applications. For example, fusion of PGRP-L polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the half-life time in vivo. Nuclear localization signals fused to PGRP-L polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and PGRP-L polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891).

Human IgG Fc region:

(SEQ ID NO:5)
GGGATCCGGAGCCCAAATCTTCTGACAAAACTCACACATGCCCACCGTGCCCAGCACCTGAATTCGAGGGTG

CACCGTCAGTCTTCCTCTTCCCCCCAAAACCCAAGGACACCCTCATGATCTCCCGGACTCCTGAGGTCACAT

GCGTGGTGGTGGACGTAAGCCACGAAGACCCTGAGGTCAAGTTCAACTGGTACGTGGACGGCGTGGAGGTGC

ATAATGCCAAGACAAAGCCGCGGGAGGAGCAGTACAACAGCACGTACCGTGTGGTCAGCGTCCTCACCGTCC

TGCACCAGGACTGGCTGAATGGCAAGGAGTACAAGTGCAAGGTCTCCAACAAAGCCCTCCCAACCCCCATCG

AGAAAACCATCTCCAAAGCCAAAGGGCAGCCCCGAGAACCACAGGTGTACACCCTGCCCCCATCCCGGGATG

AGCTGACCAAGAACCAGGTCAGCCTGACCTGCCTGGTCAAAGGCTTCTATCCAAGCGACATCGCCGTGGAGT

GGGAGAGCAATGGGCAGCCGGAGAACAACTACAAGACCACGCCTCCCGTGCTGGACTCCGACGGCTCCTTCT

TCCTCTACAGCAAGCTCACCGTGGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCGGGTAAATGAGTGCGACGGCCGC

GACTCTAGAGGAT

Example 11

Production of an Antibody a) Hybridoma Technology

The antibodies of the present invention can be prepared by a variety of methods. (See, Current Protocols, Chapter 2.) As one example of such methods, cells expressing polypeptide(s) of the invention are administered to an animal to induce the production of sera containing polyclonal antibodies. In a preferred method, a preparation of polypeptide(s) of the invention is prepared and purified to render it substantially free of natural contaminants. Such a preparation is then introduced into an animal in order to produce polyclonal antisera of greater specific activity.

Monoclonal antibodies specific for polypeptide(s) of the invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with polypeptide(s) of the invention or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the polypeptide(s) of the invention.

Alternatively, additional antibodies capable of binding to polypeptide(s) of the invention can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by polypeptide(s) of the invention. Such antibodies comprise anti-idiotypic antibodies to the protein-specific antibody and are used to immunize an animal to induce formation of further protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985)).

b) Isolation of Antibody Fragments Directed against Polypeptide(s) from a Library of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library

A library of scFvs is constructed from the RNA of human PBLs as described in PCT publication WO 92/01047. To rescue phage displaying antibody fragments, approximately $10^9$ E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×$10^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 µg/ml kanamycin and grown overnight. Phages are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately $10^{13}$ transducing units/ml (ampicillin-resistant clones).

Panning of the Library

Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect *E. coli* HB 2151 and soluble scFv is produced (Marks, et al., 1991) from single colonies for assay. ELISAs are performed with microtiter plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 12

Production of PGRP-L Protein for High-Throughput Screening Assays

The following protocol produces a supernatant containing PGRP-L polypeptide to be tested. This supernatant can then be used in the Screening Assays described in Examples 14–21.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 µg/ml. Add 200 µl of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2 \times 10^5$ cells/well in 0.5 ml DMEM (Dulbecco's Modified Eagle Medium)(with 4.5 G/L glucose and L-glutamine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 µl Lipofectamine (18324-012 Gibco/BRL) and 5 ml Optimem I (31985070 Gibco/BRL)/96-well plate. With a small volume multi-channel pipetter, aliquot approximately 2 µg of an expression vector containing a polynucleotide insert, produced by the methods described in Examples 8–10, into an appropriately labeled 96-well round bottom plate. With a multi-channel pipetter, add 50 µl of the Lipofectamine/Optimem I mixture to each well. Pipette up and down gently to mix. Incubate at RT 15–45 minutes. After about 20 minutes, use a multi-channel pipetter to add 150 µl Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipettor with tips on every other channel, adds the 200 ul of DNA/Lipofectamine/Optimem I complex to the odd wells first, then to the even wells, to each row on the 24-well plates. Incubate at 37 degree C. for 6 hours.

While cells are incubating, prepare appropriate media, either 1%BSA in DMEM with 1×penstrep, or HGS CHO-5 media (116.6 mg/L of $CaCl_2$ (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of KCl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2HPO_4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCl-$H_2O$; 31.29 mg/ml of L-Cystine-2HCl; 7.35 mg/ml of L-Glutamic Acid; 365.0 mg/ml of L-Glutamine; 18.75 mg/ml of Glycine; 52.48 mg/ml of L-Histidine-HCl-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2$H_2O$; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCl; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1×penstrep. (BSA (81-068-3 Bayer) 100 gm dissolved in 1L DMEM for a 10% BSA stock solution). Filter the media and collect 50 µl for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degree C. for 45 or 72 hours depending on the media used: 1%BSA for 45 hours or CHO-5 for 72 hours.

On day four, using a 300 µl multichannel pipettor, aliquot 600 µl in one 1 ml deep well plate and the remaining supernatant into a 2 ml deep well. The supernatants from each well can then be used in the assays described in Examples 14–21.

It is specifically understood that when activity is obtained in any of the assays described below using a supernatant, the activity originates from either the PGRP-L polypeptide directly (e.g., as a secreted protein) or by PGRP-L inducing expression of other proteins, which are then secreted into the supernatant. Thus, the invention further provides a method of identifying the protein in the supernatant characterized by an activity in a particular assay.

Example 13

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table III below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xaa-Trp-Ser (SEQ ID NO:6)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table III below.) Thus, by using GAS elements linked to reporter molecules, activators of the Jaks-STATs pathway can be identified.

TABLE III

| Ligand | JAKs | | | | STATS | GAS (elements) or ISRE |
| --- | --- | --- | --- | --- | --- | --- |
|  | tyk2 | Jak1 | Jak2 | Jak3 |  |  |
| IFN family |  |  |  |  |  |  |
| IFN-a/B | + | + | − | − | 1,2,3 | ISRE |
| IFN-g |  | + | + | − | 1 | GAS (IRF1 > Lys6 > IFP) |
| Il-10 | + | ? | ? | − | 1,3 |  |
| gp130 family |  |  |  |  |  |  |
| IL-6 (Pleiotrophic) | + | + | + | ? | 1,3 | GAS (IRF1 > Lys6 > IFP) |
| Il-11 (Pleiotrophic) | ? | + | ? | ? | 1,3 |  |
| OnM (Pleiotrophic) | ? | + | + | ? | 1,3 |  |
| LIF (Pleiotrophic) | ? | + | + | ? | 1,3 |  |
| CNTF (Pleiotrophic) | −/+ | + | + | ? | 1,3 |  |
| G-CSF (Pleiotrophic) | ? | + | ? | ? | 1,3 |  |
| IL-12 (Pleiotrophic) | + | − | + | + | 1,3 |  |
| g-C family |  |  |  |  |  |  |
| IL-2 (lymphocytes) | − | + | − | + | 1,3,5 | GAS |

TABLE III-continued

| | | JAKs | | | | |
| Ligand | tyk2 | Jak1 | Jak2 | Jak3 | STATS | GAS (elements) or ISRE |
|---|---|---|---|---|---|---|
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS (B − CAS > IRF1 = IFP >> Ly6) |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 14–15, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is: 5':GCGCCTC-GAGATTTCCCCGAAATCTAGATTTC-CCCGAAATGATTTCCCCGAAATGATTTC-CCCGAAATATCTGCCATCTCAATTAG:3' (SEQ ID NO:7)

The downstream primer is complementary to the SV40 promoter and is flanked with a Hind III site: 5':GCG-GCAAGCTTTTTGCAAAGCCTAGGC:3' (SEQ ID NO:8)

PCR amplification is performed using the SV40 promoter template present in the β-gal promoter plasmid obtained from Clontech. The resulting PCR fragment is digested with XhoI/Hind III and subcloned into BLSK2-. (Stratagene.) Sequencing with forward and reverse primers confirms that the insert contains the following sequence: 5' CTCGAGATTTCCCCGAAATCTAGATTTCCCCGAAA TGATTTCCCCGAAATGATTTC-CCCGAAATATCTGCCATCTCAATTAGT-CAGCAACCATAGTCCCGCCCCTAACTC-CGCCCATCCCGCCCCTAACTCCGCCCAGTTCCG CCCATTCTCCGCCCATGGCTGAC-TAATTTTTTTATTTATGCAGAGGC-CGAGGCCGCCTCGGCCTCTGAGCTATTC-CAGAAGTAGTGAGGAGGCTTTTTTGGAGGCCTAG GCTTTTGCAAAAAGCTT:3' (SEQ ID NO:9)

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, β-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 14–15.

Other constructs can be made using the above description and replacing GAS with a different promoter sequence. For example, construction of reporter molecules containing NFK-B and EGR promoter sequences are described in Examples 16 and 17. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, I1-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 14

High-Throughput Screening Assay for T-cell Activity

The following protocol is used to assess T-cell activity of PGRP-L by determining whether PGRP-L supernatant proliferates and/or differentiates T-cells. T-cell activity is assessed using the GAS/SEAP/Neo construct produced in Example 13. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 µl of cells. Thus, it is either scaled up, or performed in multiple to generate sufficient cells for multiple 96 well plates. Jurkat cells are maintained in RPMI+10% serum with 1%Pen-Strep. Combine 2.5 ml of OPTI-MEM (Life Technologies) with 10 µg of plasmid DNA in a T25 flask. Add 2.5 ml OPTI-MEM containing 50 µl of DMRIE-C and incubate at room temperature for 15–45 mm.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37 degree C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing PGRP-L polypeptides or PGRP-L induced polypeptides as produced by the protocol described in Example 12.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 µl of cells into each well (therefore adding 100, 000 cells per well).

After all the plates have been seeded, 50 µl of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 µl samples from each well are then transferred to an opaque 96 well plate using a 12 channel pipette. The opaque plates should be covered (using sellophene covers) and stored at −20 degree C. until SEAP assays are performed according to Example 18. The plates containing the remaining treated cells are placed at 4 degree C. and serve as a source of material for repeating the assay on a specific well if desired.

As a positive control, 100 Unit/ml interferon gamma can be used which is known to activate Jurkat T cells. Over 30 fold induction is typically observed in the positive control wells.

Example 15

High-Throughput Screening Assay Identifying Myeloid Activity

The following protocol is used to assess myeloid activity of PGRP-L by determining whether PGRP-L proliferates and/or differentiates myeloid cells. Myeloid cell activity is assessed using the GAS/SEAP/Neo construct produced in Example 13. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/ Neo construct produced in Example 13, a DEAE-Dextran method (Kharbanda et. al., 1994, Cell Growth & Differentiation, 5:259–265) is used. First, harvest $2 \times 10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 µg GAS-SEAP2 plasmid DNA, 140 mM NaCl, 5 mM KCl, 375 µM $Na_2HPO_4.7H_2O$, 1 mM $MgCl_2$, and 675 µM $CaCl_2$. Incubate at 37 degree C. for for 45 min.

Wash the cells with RPMI 1640 medium containing 10% FBS and then resuspend in 10 ml complete medium and incubate at 37 degree C. for 36 hr.

The GAS-SEAP/U937 stable cells are obtained by growing the cells in 400 µg/ml G418. The G418-free medium is used for routine growth but every one to two months, the cells should be re-grown in 400 µg/ml G418 for a couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 µl cells per well in the 96-well plate (or $1 \times 10^5$ cells/well).

Add 50 µl of the supernatant prepared by the protocol described in Example 12. Incubate at 37 degree C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 18.

Example 16

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by PGRP-L.

Particularly, the following protocol is used to assess neuronal activity in PC12 cell lines. $PCl_2$ cells (rat phaeochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by PGRP-L can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers: 5' GCGCTCGAGGGATGACAGCGATAGAACCCCGG-3' (SEQ ID NO:10) and 5' GCGAAGCTTCGCGACTCCCCGGATCCGCCTC-3' (SEQ ID NO:11)

Using the GAS:SEAP/Neo vector produced in Example 13, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two ml of a coating solution (1:30 dilution of collagen type I (Upstate Biotech Inc. Cat#08–115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 μg/ml streptomycin on a precoated 10 cm tissue culture dish. One to four split is done every three to four days. Cells are removed from the plates by scraping and resuspended by trituration, pipetting up and down for more than 15 times.

Transfect the EGR/SEAP/Neo construct into PC12 using the Lipofectamine protocol described in Example 12. EGR-SEAP/PC12 stable cells are obtained by growing the cells in 300 μg/ml G418. The G418-free medium is used for routine growth but every one to two months, the cells should be re-grown in 300 μg/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 μl of the cell suspension to each well of 96-well plate (equivalent to $1 \times 10^5$ cells/well). Add 50 μl supernatant produced by Example 12, 37 degree C. for 48 to 72 hr. As a positive control, a growth factor known to activate PC12 cells through EGR can be used, such as 50 ng/μl of Neuronal Growth Factor (NGF). Over fifty-fold induction of SEAP is typically seen in the positive control wells. SEAP assay the supernatant according to Example 18.

Example 17

High-Throughput Screening Assay for T-cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 12. Activators or inhibitors of NF-KB would be useful in treating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:12), 18 bp of sequence complementary to the 5' end of the SV40 early promoter sequence, and is flanked with an XhoI site: 5' GCGGCCTCGAGGGGACTTTCCCGGG-GACTTTCCGGGGACTTTCCGGGACTTTC-CATCCTGCCATCTCAATTAG 3' (SEQ ID NO:13).

The downstream primer is complementary to the 3' end of the SV40 promoter and is flanked with a Hind III site: 5' GCGGCAAGCTTTTTGCAAAGCCTAGGC 3' (SEQ ID NO:8).

PCR amplification is performed using the SV40 promoter template present in the pβ-gal:promoter plasmid obtained from Clontech. The resulting PCR fragment is digested with XhoI and Hind III and subcloned into BLSK2. (Stratagene) Sequencing with the T7 and T3 primers confirms the insert contains the following sequence: 5' CTCGAGGG-GACTTTCCCGGGGACTTTCCGGG-GACTTTCCGGGACTTTCCATCTGC-CATCTCAATTAGTCAGCAACCATAGTCCCGCCCCT AACTCCGCCCATCCCGCCCTAACTC-CGCCCAGTTCCGCCCATTCTCCGC-CCCATGGCTGACTAATTTTTTTATT-TATGCAGAGGCCGAGGCCGCCTCGGCCTCTGAGC TATTCCAGAAGTAGTGAGGAG-GCTTTTTTGGAGGCCTAGGCTTTTG-CAAAAAGCTT:3' (SEQ ID NO:14).

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 14. Similarly, the method for assaying supernatants with these stable Jurkat T-cells is also described in Example 14. As a positive control, exogenous TNF alpha (0.1,1, 10 ng) is added to wells H9, H10, and H11, with a 5–10 fold activation typically observed.

Example 18

Assay for SEAP Activity

As a reporter molecule for the assays described in Examples 14–17, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 μl of 2.5×dilution buffer into Optiplates containing 35 μl of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see Table IV below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

TABLE IV

Reaction Buffer Formulation

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 19

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 μl of HBSS (Hank's Balanced Salt Solution) leaving 100 μl of buffer after the final wash.

A stock solution of 1 mg/ml fluo-3 is made in 10% pluronic acid DMSO. To load the cells with fluo-3, 50 μl of 12 μg/ml fluo-3 is added to each well. The plate is incubated at 37 degree C. in a $CO_2$ incubator for 60 min. The plate is washed four times in the Biotek washer with HBSS leaving 100 μl of buffer.

For non-adherent cells, the cells are spun down from culture media. Cells are re-suspended to $2-5 \times 10^6$ cells/ml with HBSS in a 50-ml conical tube. 4 μl of 1 mg/ml fluo-3 solution in 10% pluronic acid DMSO is added to each ml of cell suspension. The tube is then placed in a 37 degree C. water bath for 30–60 min. The cells are washed twice with HBSS, resuspended to $1 \times 10^6$ cells/ml, and dispensed into a microplate, 100 μl/well. The plate is centrifuged at 1000 rpm for 5 min. The plate is then washed once in Denley CellWash with 200 μl, followed by an aspiration step to 100 μl final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 μl. Increased emission at 530 nm indicates an extracellular signaling event caused by the a molecule, either PGRP-L or a molecule induced by PGRP-L, which has resulted in an increase in the intracellular $Ca^{++}$ concentration.

Example 20

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether PGRP-L or a molecule induced by PGRP-L is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or poly L-lysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamar Blue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 μl of the supernatant produced in Example 12, the medium was removed and 100 ml of extraction buffer ((20 mM HEPES pH 7.5, 0.15 M NaCl, 1% Triton X-100, 0.1% SDS, 2 mM $Na_3VO_4$, 2 mM $Na4P_2O_7$ and a cocktail of protease inhibitors (#1836170) obtained from Boehringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degree C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 μl of 5 μM Biotinylated Peptide, then 10 μATP/$Mg^{2+}$ (5 mM ATP/50 mM $MgCl_2$), then 10 μl of 5×Assay Buffer (40 mM imidazole hydrochloride, pH7.3, 40 mM β-glycerophosphate, 1 mM EGTA, 100 mM $MgCl_2$, 5 mM $MnCl_2$, 0.5 mg/ml BSA), then 5 μl of Sodium Vanadate (1 mM), and then 5 μl of water. Mix the components gently and pre-incubate the reaction mix at 30 degree C. for 2 min. Initiate the reaction by adding 10 μl of the control enzyme or the filtered supernatant.

The tyrosine kinase assay reaction is then terminated by adding 10 μl of 120 mM EDTA and place the reactions on ice.

Tyrosine kinase activity is determined by transferring 50 μl aliquot of reaction mixture to a microtiter plate (MTP) module and incubating at 37 degree C. for 20 min. This allows the streptavidin coated 96 well plate to associate with the biotinylated peptide. Wash the MTP module with 300 μl/well of PBS four times. Next add 75 μl of anti-phosphotyrosine antibody conjugated to horse radish peroxidase (anti-P-Tyr-POD(0.5 μg/ml)) to each well and incubate at 37 degree C. for one hour. Wash the well as above.

Next add 100 μl of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 21

High-Throughput Screening Assay Identifying Phosphorylation Activity

As a potential alternative and/or compliment to the assay of protein tyrosine kinase activity described in Example 20, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phospho-serine, phosphotyrosine, or phospho-threonine molecule, can be detected by substituting these molecules for Erk-1 or Erk-2 in the following assay.

Specifically, assay plates are made by coating the wells of a 96-well ELISA plate with 0.1 ml of protein G (1 μg/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degree C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 μl of the supernatants obtained in Example 12 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 µg/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by PGRP-L or a molecule induced by PGRP-L.

Example 22

Method of Determining Alterations in the PGRP-L Gene

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degree C. for 30 seconds; 60–120 seconds at 52–58 degree C.; and 60–120 seconds at 70 degree C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of PGRP-L is also determined and genomic PCR products analyzed to confirm the results. PCR products harboring suspected mutations in PGRP-L are then cloned and sequenced to validate the results of the direct sequencing.

PCR products of PGRP-L are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in PGRP-L not present in unaffected individuals.

Genomic rearrangements are also observed as a method of determining alterations in the PGRP-L gene. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the PGRP-L genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of PGRP-L (hybridized by the probe) are identified as insertions, deletions, and translocations. These PGRP-L alterations are used as a diagnostic marker for an associated disease.

Example 23

Method of Detecting Abnormal Levels of PGRP-L in a Biological Sample

PGRP-L polypeptides can be detected in a biological sample, and if an increased or decreased level of PGRP-L is detected, this polypeptide is a marker for a particular phenotype. Methods of detection are numerous, and thus, it is understood that one skilled in the art can modify the following assay to fit their particular needs.

For example, antibody-sandwich ELISAs are used to detect PGRP-L in a sample, preferably a biological sample. Wells of a microtiter plate are coated with specific antibodies to PGRP-L, at a final concentration of 0.2 to 10 ug/ml. The antibodies are either monoclonal or polyclonal and are produced by the method described in Example 11. The wells are blocked so that non-specific binding of PGRP-L to the well is reduced.

The coated wells are then incubated for >2 hours at RT with a sample containing PGRP-L. Preferably, serial dilutions of the sample should be used to validate results. The plates are then washed three times with deionized or distilled water to remove unbound PGRP-L.

Next, 50 µl of specific antibody-alkaline phosphatase conjugate, at a concentration of 25–400 ng, is added and incubated for 2 hours at room temperature. The plates are again washed three times with deionized or distilled water to remove unbound conjugate.

Add 75 µl of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot PGRP-L polypeptide concentration on the X-axis (log scale) and fluorescence or absorbance of the Y-axis (linear scale). Interpolate the concentration of the PGRP-L in the sample using the standard curve.

Example 24

Formulating a Polypeptide

The PGRP-L composition will be formulated and dosed in a fashion consistent with good medical practice, taking into account the clinical condition of the individual patient (especially the side effects of treatment with the PGRP-L polypeptide alone), the site of delivery, the method of administration, the scheduling of administration, and other factors known to practitioners. The "effective amount" for purposes herein is thus determined by such considerations.

As a general proposition, the total pharmaceutically effective amount of PGRP-L administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, PGRP-L is typically administered at a dose rate of about 1 ug/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing PGRP-L are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intracisternal, subcutaneous and intraarticular injection and infusion.

PGRP-L is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(−)-3-hydroxybutyric acid (EP 133,988). Sustained-release compositions also include liposomally entrapped PGRP-L polypeptides. Liposomes containing the PGRP-L are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, PGRP-L is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting PGRP-L uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

PGRP-L is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

PGRP-L used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

PGRP-L polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous PGRP-L polypeptide solution, and the resulting mixture is lyophilized. The infusion solution is prepared by reconstituting the lyophilized PGRP-L polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, PGRP-L may be employed in conjunction with other therapeutic compounds.

The compositions of the invention may be administered alone or in combination with other therapeutic agents. Therapeutic agents that may be administered in combination with the compositions of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6

(International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

Conventional nonspecific immunosuppressive agents, that may be administered in combination with the compositions of the invention include, but are not limited to, steroids, cyclosporine, cyclosporine analogs, cyclophosphamide methyl-prednisone, prednisone, azathioprine, FK-506, 15-deoxyspergualin, and other immunosuppressive agents that act by suppressing the function of responding T cells.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In an additional embodiment, the compositions of the invention are administered in combination with angeogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

Example 25

Method of Treating Decreased Levels of PGRP-L

The present invention relates to a method for treating an individual in need of a decreased level of PGRP-L activity in the body comprising, administering to such an individual a composition comprising a therapeutically effective amount of PGRP-L antagonist. Preferred antagonists for use in the present invention are PGRP-L-specific antibodies.

Moreover, it will be appreciated that conditions caused by a decrease in the standard or normal expression level of PGRP-L in an individual can be treated by administering PGRP-L, preferably in the secreted form. Thus, the invention also provides a method of treatment of an individual in need of an increased level of PGRP-L polypeptide comprising administering to such an individual a pharmaceutical composition comprising an amount of PGRP-L to increase the activity level of PGRP-L in such an individual.

For example, a patient with decreased levels of PGRP-L polypeptide receives a daily dose 0.1–100 µg/kg of the polypeptide for six consecutive days. Preferably, the polypeptide is in the secreted form. The exact details of the dosing scheme, based on administration and formulation, are provided in Example 24.

Example 26

Method of Treating Increased Levels of PGRP-L

The present invention also relates to a method for treating an individual in need of an increased level of PGRP-L activity in the body comprising administering to such an individual a composition comprising a therapeutically effective amount of PGRP-L or an agonist thereof.

Antisense technology is used to inhibit production of PGRP-L. This technology is one example of a method of decreasing levels of PGRP-L polypeptide, preferably a secreted form, due to a variety of etiologies, such as cancer.

For example, a patient diagnosed with abnormally increased levels of PGRP-L is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 24.

Example 27

Method of Treatment Using Gene Therapy—Ex Vivo

One method of gene therapy transplants fibroblasts, which are capable of expressing PGRP-L polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding PGRP-L can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted PGRP-L.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the PGRP-L gene is then added to the media and the packaging cells transduced with the vector. The packaging cells now produce infectious viral particles containing the PGRP-L gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether PGRP-L protein is produced.

The engineered fibroblasts are then transplanted onto the host, either alone or after having been grown to confluence on cytodex 3 microcarrier beads.

Example 28

Gene Therapy Using Endogenous PGRP-L Gene

Another method of gene therapy according to the present invention involves operably associating the endogenous PGRP-L sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous PGRP-L, flanking the promoter. The targeting sequence will be sufficiently near the 5' end of PGRP-L so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous PGRP-L sequence. This results in the expression of PGRP-L in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the PGRP-L locus, plasmid pUC 18 (MBI Fermentas, Amherst, N.Y.) is digested with HindIII. The CMV promoter is amplified by PCR with an XbaI site on the 5' end and a BamHI site on the 3'end. Two PGRP-L non-coding sequences are amplified via PCR: one PGRP-L non-coding sequence (PGRP-L fragment 1) is amplified with a HindIII site at the 5' end and an Xba site at the 3'end; the other PGRP-L non-coding sequence (PGRP-L fragment 2) is amplified with a BamHI site at the 5'end and a HindIII site at the 3'end. The CMV promoter and PGRP-L fragments are digested with the appropriate enzymes (CMV promoter—XbaI and BamHI; PGRP-L fragment 1—baI; PGRP-L fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 $\mu$g/ml. 0.5 ml of the cell suspension (containing approximately $1.5.\times10^6$ cells) is then added to the cuvette, and the cell suspension and DNA solutions are gently mixed. Electroporation is performed with a Gene-Pulser apparatus (Bio-Rad). Capacitance and voltage are set at 960 $\mu$F and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 29

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) PGRP-L sequences into an animal to increase or decrease the expression of the PGRP-L polypeptide. The PGRP-L polynucleotide may be operatively linked to a promoter or any other genetic elements necessary for the expression of the PGRP-L polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The PGRP-L polynucleotide constructs may be delivered by any method that delivers injectable materials to the cells of an animal, such as, injection into the interstitial space of tissues (heart, muscle, skin, lung, liver, intestine and the like). The PGRP-L polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the PGRP-L polynucleotides may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The PGRP-L polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The PGRP-L polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked PGRP-L polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked PGRP-L polynucleotide constructs can be delivered to arteries during angioplasty by the catheter used in the procedure.

The dose response effects of injected PGRP-L polynucleotide in muscle in vivo is determined as follows. Suitable PGRP-L template DNA for production of mRNA coding for PGRP-L polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The PGRP-L template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for PGRP-L protein expression. A time course for PGRP-L protein expression may be done in a similar fashion except that quadriceps from different mice are harvested at different times. Persistence of PGRP-L DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using PGRP-L naked DNA.

Example 30

PGRP-L Transgenic Animals

The PGRP-L polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pluripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campbell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of PGRP-L polypeptides, studying conditions and/or disorders associated with aberrant PGRP-L expression, and in screening for compounds effective in ameliorating such conditions and/or disorders.

Example 31

PGRP-L Knock-Out Animals

Endogenous PGRP-L gene expression can also be reduced by inactivating or "knocking out" the PGRP-L gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the PGRP-L polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of PGRP-L polypeptides, studying conditions and/or disorders associated with aberrant PGRP-L expression, and in screening for compounds effective in ameliorating such conditions and/or disorders.

Example 32

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay

Purified PGRP-L protein, or truncated forms thereof, is assessed for its ability to induce activation, proliferation, differentiation or inhibition and/or death in B-cell populations and their precursors. The activity of PGRP-L protein on purified human tonsillar B cells, measured qualitatively over the dose range from 0.1 to 10,000 ng/ml, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2-ME, 100 U/ml penicillin, 10 µg/ml streptomycin, and $10^{-5}$ dilution of SAC) in a total volume of 150 µl. Proliferation or inhibition is quantitated by a 20 h pulse (1 µCi/well) with $^3$H-thymidine (6.7 Ci/mM) beginning 72 h post factor addition. The positive and negative controls are IL2 and medium respectively.

In Vivo Assay

BALB/c mice are injected (i.p.) twice per day with buffer only, or 2 mg/Kg of PGRP-L protein, or truncated forms thereof. Mice receive this treatment for 4 consecutive days, at which time they are sacrificed and various tissues and serum collected for analyses. Comparison of H&E sections from normal and PGRP-L protein-treated spleens identify the results of the activity of PGRP-L protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from PGRP-L protein-treated mice is used to indicate whether PGRP-L protein specifically increases the proportion of ThB+, CD45R(B220) dull B cells over that which is observed in control mice.

Likewise, a predicted consequence of increased mature B-cell representation in vivo is a relative increase in serum Ig titers. Accordingly, serum IgM and IgA levels are compared between buffer and PGRP-L protein-treated mice.

The studies described in this example tested activity in PGRP-L protein. However, one skilled in the art could easily modify the exemplified studies to test the activity of PGRP-L polynucleotides (e.g., gene therapy), agonists, and/or antagonists of PGRP-L.

Example 33

T Cell Proliferation Assay

A CD3-induced proliferation assay is performed on PBMCs and is measured by the uptake of $^3$H-thymidine. The assay is performed as follows. Ninety-six well plates are coated with 100 µl/well of mAb to CD3 (HIT3a, Pharmingen) or isotype-matched control mAb (B33.1) overnight at 4° C. (1 µg/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of PGRP-L protein (total volume 200 µl). Relevant protein buffer and medium alone are controls. After 48 hr. culture at 37° C., plates are spun for 2 min. at 1000 rpm and 100 µl of supernatant is removed and stored –20° C. for measurement of IL-2 (or other cytokines) if effect on proliferation is observed. Wells are supplemented with 100 µl of medium containing 0.5 µCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of PGRP-L proteins.

The studies described in this example tested activity in PGRP-L protein. However, one skilled in the art could easily modify the exemplified studies to test the activity of PGRP-L polynucleotides (e.g., gene therapy), agonists, and/or antagonists of PGRP-L.

Example 34

Effect of PGRP-L on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD 1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of PGRP-L or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of PGRP-L for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the Expression of MHC Class II, Costimulatory and Adhesion Molecules

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of PGRP-L or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte Activation and/or Increased Survival

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. PGRP-L, agonists, or antagonists of PGRP-L can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay

Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2 \times 10^6$/ml in PBS containing PI at a final concentration of 5 µg/ml, and then incubated at room temperature for 5 minutes before FACScan analysis. PI uptake has been demonstrated to correlate with DNA fragmentation in this experimental paradigm.

Effect on Cytokine Release

An important function of monocytes/macrophages is their regulatory activity on other cellular populations of the immune system through the release of cytokines after stimulation. An ELISA to measure cytokine release is performed as follows. Human monocytes are incubated at a density of $5 \times 10^5$ cells/ml with increasing concentrations of PGRP-L and under the same conditions, but in the absence of PGRP-L. For IL-12 production, the cells are primed overnight with IFN (100 U/ml) in presence of PGRP-L. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g., R & D Systems (Minneapolis, Minn.)) and applying the standard protocols provided with the kit.

Oxidative Burst

Purified monocytes are plated in 96-w plate at $2\text{-}1 \times 10^5$ cell/well. Increasing concentrations of PGRP-L are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 µl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in PGRP-L protein. However, one skilled in the art could easily modify the exemplified studies to test the activity of PGRP-L polynucleotides (e.g., gene therapy), agonists, and/or antagonists of PGRP-L.

Example 35

PGRP-L Biological Effects

Astrocyte and Neuronal Assays

Recombinant PGRP-L, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate PGRP-L's activity on these cells.

Moreover, previous reports describing the biological effects of FGF-2 (basic FGF) on cortical or hippocampal neurons in vitro have demonstrated increases in both neuron survival and neurite outgrowth (Walicke, P. et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of PGRP-L to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or PGRP-L with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or PGRP-L with or without IL-1α for 24 hours. The supernatants are collected and assayed for IL-6 by ELISA kit (Endogen, Cambridge, Mass.).

Human lung fibroblasts are cultured with FGF-2 or PGRP-L for 3 days in basal medium before the addition of Alamar Blue to assess effects on growth of the fibroblasts. FGF-2 should show a stimulation at 10–2500 ng/ml which can be used to compare stimulation with PGRP-L.

Parkinson Models

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, PGRP-L can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of PGRP-L is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyomithine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopaminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if PGRP-L acts to prolong the survival of dopaminergic neurons, it would suggest that PGRP-L may be involved in Parkinson's Disease.

The studies described in this example tested activity in PGRP-L protein. However, one skilled in the art could easily modify the exemplified studies to test the activity of PGRP-L polynucleotides (e.g., gene therapy), agonists, and/or antagonists of PGRP-L.

Example 36

Suppression of TNF Alpha-induced Adhesion Molecule Expression by PGRP-L

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of PGRP-L to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% $CO_2$. HUVECs are seeded in 96-well plates at concentrations of $1\times10^4$ cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 μl of 199 Medium (10% FBS). Samples for testing and positive or negative controls are added to the plate in triplicate (in 10 μl volumes). Plates are incubated at 37 degree C. for either 5 h (selectin and integrin expression) or 24 h (integrin expression only). Plates are aspirated to remove medium and 100 μl of 0.1% paraformaldehyde-PBS(with $Ca^{++}$ and $Mg^{++}$) is added to each well. Plates are held at 4° C. for 30 min.

Fixative is then removed from the wells and wells are washed 1× with PBS(+Ca, Mg)+0.5% BSA and drained. Do not allow the wells to dry. Add 10 μl of diluted primary antibody to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed×3 with PBS(+Ca, Mg)+0.5% BSA.

Then add 20 μl of diluted ExtrAvidin-Alkaline Phosphatase (1:5,000 dilution) to each well and incubated at 37° C. for 30 min. Wells are washed×3 with PBS(+Ca, Mg)+0.5% BSA. 1 tablet of p-Nitrophenol Phosphate (pNPP) is dissolved in 5 ml of glycine buffer (pH 10.4). 100 μl of pNPP substrate in glycine buffer is added to each test well. Standard wells in triplicate are prepared from the working dilution of the ExtrAvidin-Alkaline Phosphatase in glycine buffer: 1:5,000 ($10^0$)>$10^{-0.5}$>$10^{-1}$>$10^{-1.5}$. 5 μl of each dilution is added to triplicate wells and the resulting AP content in each well is 5.50 ng, 1.74 ng, 0.55 ng, 0.18 ng. 100 μl of pNNP reagent must then be added to each of the standard wells. The plate must be incubated at 37° C. for 4 h. A volume of 50 μl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity in PGRP-L protein. However, one skilled in the art could easily modify the exemplified studies to test the activity of PGRP-L polynucleotides (e.g., gene therapy), agonists, and/or antagonists of PGRP-L.

Example 37

Peptidoglycan Binding Assay

Insoluble peptidoglycan is prepared from *Micrococcus luteus* as has been described in the art (Araki, Y., Nakatani, T., Nakayama, K. and Ito, E., 1972, J. Biol. Chem., 247:6312–632, which is herein incorporated by reference in its entirety).

The peptidoglycan binding assay is performed by incubating 0.32 mgs of peptidoglycan in 280 μl of 10 mM maleate buffer, pH 6.5/0.15 M NaCl with 3–6 μg of a PGRP in 40 μl of 1 M imidazole/0.5 M NaCl/20 mM Tris-HCl, pH 7.9, for 30 min. at 4° C. One-sixteenth of the supernatant and of the pellet was removed for analysis. The protein was separated for the peptidoglycan by boiling in 2% SDS/PAGE loading buffer, subjected to electrophoresis on an SDS/15% polyacrylamide gel, and stained with Coomassie brilliant blue.

It can be appreciated by those skilled in the art that the above assay may be altered and/or refined to a degree to enhance visualization of the binding, while essentially maintaining the general scheme of the assay. Further peptidoglycan binding assays are described by Yoshida et al., JBC, 271 (23): 13854 (1996), which is herein incorporated by reference in its entirety.

Example 38

Measurement of Apoptosis Ability of PGRP-L

In a first incubation step, anti-histone antibody is fixed adsorptively on the wall of a microtiter plate module. Subsequently, non-specific binding sites on the wall are saturated by treatment with incubation buffer (e.g., blocking solution). During the second incubation step, the nucleosomes contained in the appropriate cell (e.g., WEHI 164 cells) sample treated with the PGRP-L bind via their histone components to the immobilized anti-histone antibody. In the third incubation step, anti-DNA-peroxidase reacts with the DNA-part of the nucleosomes. After removal of all unbound peroxidase conjugate by a washing step, the amount of peroxidase retained in the immunocomplex is determined photometrically with ABTS (2,2'-azino-di-[3-ethylbenzthiazoline sulfonate]), as a substrate. Anti-histone antibody reacts with the histones H1, H2A, $H_2B$, H3 and H4 from the sample. Anti-DNA POD antibody binds to single- and double-stranded DNA. Therefore, the ELISA allows the detection on mono- and oligonucleosomes and may be applied to measure apoptotic cell death. The level of cell death is measured by the amount of cytoplasmic histone-associated DNA fragments which are indicated as the absorbance A405 nm/A490. (See Boehringer Mannheim Catalogue, 0990 C 93 2 1541170).

Example 39

Apoptosis Assays

A.) Cell Death Assay

Assays known in the art can be used or routinely modified, including the following alamar blue assay. Alamar blue is an oxidation-reduction indicator that both fluoresces and changes color in response to chemical reduction of growth medium resulting from cell growth. As cells grow in culture, innate metabolic activity results in a chemical reduction of the immediate surrounding environment. Reduction related to growth causes the indicator to change from oxidized (non-fluorescent blue) form to reduced (fluorescent red) form. i.e. stimulated proliferation will produce a stronger signal and inhibited proliferation will produce a weaker signal and the total signal is proportional to the total number of cells as well as their metabolic activity. The background level of activity is observed with the starvation medium alone. This is compared to the output observed from the positive control samples (sFasL in growth medium), negative control samples (medium only) and protein dilutions.

Jurkat cells (ATCC Accession No. TIB-152) are grown in RPMI 1640 (Hyclone #SH30027.01), 10% FBS (Hyclone #AHK9040), 1% P/S (Biowhittaker #17-602E), and 1% L-Glutamine (Biowhittaker #17-905C). Alternatively, L929 cells (ATCC Accession No. CCL-1) are grown in DMEM (Hyclone #AKD11647), 10% FBS (Hyclone #AHK9040), 1% P/S (Biowhittaker #17-602E), and 1% L-Glutamine (Biowhittaker #17-905C). Cells are washed with serum free medium or PBS, and harvested by centrifugation (5 mins at 200×g). Cells are aliquoted into 96 well plates with 50,000 cells/well in a total of 100 μl 5% FBS media.

Purified polypeptides of the invention are serially diluted in 5% FBS media to final concentrations of 1000, 100, 10, 1, and 0.1 ng/ml. 100 μl of polypeptide dilutions are added to each well, and positive controls (sFasL (Fisher #NC9542546) in growth medium) and negative control samples (medium only) are prepared. The plates are incubated for 16 hrs. at 37° C.

100 μl of supernatant is removed from each well, and 100 μl of 20% Alamar blue is added to each well (Alamar blue Diluted with PBS). Plates are incubated for 5 hrs at 37° C. and then read on an Elisa reader (O.D. 570 nm–630 nm). Readings having weaker signals than the negative control, and preferably a signal comparable to the positive control, are indicative of apoptotic activity due to the assayed polypeptide.

B.) Apoptosis Assay

Assays known in the art can be used or routinely modified, including the following Annexin V staining assay. Annexin V is a cell surface protein which can be detected through Annexin-V-FLUOS staining, and loss of detection of Annexin V due to membrane changes is indicative of apoptosis in the following assay. The background level of activity is observed with the starvation medium alone. This is compared to the output observed from the positive control samples (sFasL in growth medium), negative control samples (medium only) and protein dilutions.

Jurkat cells (ATCC Accession No. TIB-152) are grown in RPMI 1640 (Hyclone #SH30027.01), 10% FBS (Hyclone #AHK9040), 1% P/S (Biowhittaker #17-602E), and 1% L-Glutamine (Biowhittaker #17-905C). Alternatively, L929 cells (ATCC Accession No. CCL-1) are grown in DMEM (Hyclone #AKD11647), 10% FBS (Hyclone #AHK9040), 1% P/S (Biowhittaker 17-602E), and 1% L-Glutamine (Biowhittaker #17-905C). Cells are washed with serum free medium or PBS, and harvested by centrifugation (5 mins at 200×g). Cells are aliquoted into 96 well plates with 1,000,000 cells/well in a total of 100 μl 5% FBS media.

Purified polypeptides of the invention are serially diluted in 5% FBS media to final concentrations of 1000, 100, 10, 1, and 0.1 ng/ml. 100 μl of polypeptide dilutions are added to each well, and positive controls (sFasL (Fisher #NC9542546) in growth medium) and negative control samples (medium only) are prepared. The plates are incubated for 16 hrs. at 37° C.

Cells are washed with PBS and harvested by centrifugation (5 mins at 200×g). Cells are resuspended in 100 μl of staining solution (Annexin-V-FLUOS Staining Kit (Roche #1858777)), and incubated for 15 min. Samples are analyzed using a flow cytometer. Readings having reduced values compared to the negative control, and preferably those having values comparable to the positive controls are indicative of apoptotic activity due to the assayed polypeptide.

The PGRP-L polynucleotides and polypeptides of the present invention, including antibodies, were disclosed in U.S. provisional application serial No. 60/149,715, which is herein incorporated by reference in its entirety.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the Sequence Listing submitted herewith, in both computer and paper forms, are hereby incorporated by reference in their entireties.

What is claimed is:

1. An isolated antibody or fragment thereof that specifically binds to a protein selected from the group consisting of:
   (a) a protein consisting of amino acid residues 1 to 174 of SEQ ID NO:2;
   (b) a protein consisting of a portion of SEQ ID NO:2, wherein said portion comprises at least 30 contiguous amino acid residues of SEQ ID NO:2; and
   (c) a protein consisting of a portion of SEQ ID NO:2, wherein said portion comprises at least 50 contiguous amino acid residues of SEQ ID NO:2.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 which is a human antibody.

6. The antibody or fragment thereof of claim 1 which is a polyclonal antibody.

7. The antibody or fragment thereof of claim 1 which is a monoclonal antibody.

8. The antibody or fragment thereof of claim 1 which is selected from the group consisting of:
   (a) a chimeric antibody;
   (b) a humanized antibody;
   (c) a single chain antibody; and
   (d) a Fab fragment.

9. The antibody or fragment thereof of claim 1 which is labeled.

10. The antibody or fragment thereof of claim 9 wherein the label is selected from the group consisting of:
    (a) an enzyme;
    (b) a fluorescent label;
    (c) a luminescent label; and
    (d) a bioluminescent label.

11. The antibody or fragment thereof of claim 1 wherein said antibody or fragment thereof specifically binds to said protein in a Western blot.

12. The antibody or fragment thereof of claim 1 wherein said antibody or fragment thereof specifically binds to said protein in an ELISA.

13. A hybridoma that produces the antibody or fragment thereof of claim 1.

14. A method of detecting PGRP-L protein in a biological sample comprising:
    (a) contacting the biological sample with the antibody or fragment thereof of claim 1; and
    (b) detecting the PGRP-L protein in the biological sample.

15. The method of claim 14 wherein the antibody or fragment thereof is a polyclonal antibody.

* * * * *

SEQUENCE LISTING

<160> NUMBER OF SEQ ID NOS: 18

<210> SEQ ID NO 1
<211> LENGTH: 1200
<212> TYPE: DNA
<213> ORGANISM: human

<400> SEQUENCE: 1

```
gacgcggctg gcactgggtg ggcgcccaca cgctcggcca caactcccgg ggcttcggcg      60
tggccatagt gggcaactac accgcggcgc tgcccaccga ggccgctctg cgcacggtgc     120
gcgacacgct cccgagttgt gcggtgcgcg ccggcctcct gcggccagac tacgcgctgc     180
tgggccaccg ccagctggtg cgcaccgact gccccggcga cgcgctcttc gacctgctgc     240
gcacctggcc gcacttcacc gcggtgagtc ttcgcagcct gcactacacg gcccgccgcc     300
cctccgtcta cacaagctcc acgaggcccc tgcccctgc ctgtaacagc tgtgcccgca     360
cagcctcagc caggccccca acttcccggc ggcacgtcta ttcaggaaac ctaggcccag     420
cctttgcggg tcactctgcg ggcaacatcc ctgatcctgt gacttctgcc tatgcagcct     480
cagctcagcc ccagacccag ccagcctgtc ctttccccag ctcctaatac ctctaccttt     540
ccagccaagg catggaccct gacacctgcc aacagcccct ctgccctcac aacctcagcc     600
tggccttcat gacttctcta cccaagtcac aacctgtcag gctgcaccac ctcatcctgg     660
```

-continued

```
cccgccgaac cttgacctca cccctgcccc tacccgaagg ctctctgtcc acacaacatg      720
aacctaggct gtgacctttt gccttcacaa cctctgtcca gtccttaatc ctgtgttgca      780
attctctgtc cagacaatct caactctgag gttgcttgtt tcgtccctga ctccttaacc      840
cctgatgaca actcttatgc cagcacaact ttgacctgat gacctcatcc cagcccttga      900
tcgccatcac taaaacaatt ttagaatcac acctggacaa tctcgtgcta cctacatact      960
gccactccat ttcattaagc tattgactag cacatccatc tcggcctata gttggctttg     1020
tcctcactct ctcactttgg gccactgtcc cctccctgat aaaggggata tcaccaccga     1080
tcccacagaa atacaaacta ccatcagaga atactataaa cacctctatg caaataaact     1140
agaaaatcta aagaaatgg ataaattcct caacacccac taccaaaaaa aaaaaaaaaa      1200
```

```
<210> SEQ ID NO 2
<211> LENGTH: 174
<212> TYPE: PRT
<213> ORGANISM: human

<400> SEQUENCE: 2

Arg Gly Trp His Trp Val Gly Ala His Thr Leu Gly His Asn Ser Arg
1               5                   10                  15

Gly Phe Gly Val Ala Ile Val Gly Asn Tyr Thr Ala Ala Leu Pro Thr
            20                  25                  30

Glu Ala Leu Arg Thr Val Arg Asp Thr Leu Pro Ser Cys Ala Val
        35                  40                  45

Arg Ala Gly Leu Leu Arg Pro Asp Tyr Ala Leu Leu Gly His Arg Gln
    50                  55                  60

Leu Val Arg Thr Asp Cys Pro Gly Asp Ala Leu Phe Asp Leu Arg
65                  70                  75                  80

Thr Trp Pro His Phe Thr Ala Val Ser Leu Arg Ser Leu His Tyr Thr
                85                  90                  95

Ala Arg Arg Pro Ser Val Tyr Thr Ser Ser Thr Arg Pro Leu Pro Pro
            100                 105                 110

Ala Cys Asn Ser Cys Ala Arg Thr Ala Ser Ala Arg Pro Pro Thr Ser
        115                 120                 125

Arg Arg His Val Tyr Ser Gly Asn Leu Gly Pro Ala Phe Ala Gly His
    130                 135                 140

Ser Ala Gly Asn Ile Pro Asp Pro Val Thr Ser Ala Tyr Ala Ala Ser
145                 150                 155                 160

Ala Gln Pro Gln Thr Gln Pro Ala Cys Pro Phe Pro Ser Ser
                165                 170
```

```
<210> SEQ ID NO 3
<211> LENGTH: 1876
<212> TYPE: DNA
<213> ORGANISM: human

<400> SEQUENCE: 3
gccgttatgt gaggtaagca gctttctcca acagaagttc ctctctcctc aaaggcccag       60
agtgtccagg ccaaccaact gaccaagaat tacaactgct gaaactggcc tccgaggttc      120
tctgctgggt ctgtgccctg gaactggaga cccaccatga aggcctgggg tgccctctgg      180
atcgtgcttg gattgctgct gtggccagag ccaggggcag cctcctcctt gcctctgctc      240
atggactcca tcatccaggc ccttgctgaa cttgagcaaa aggtaccagt gactgaggcc      300
agcatcactg cctctgcatg gattctgtca gccaagaact ccagcaccca caattccctt      360
```

-continued

```
caccagcgct tgctgctgaa ggcaccaagc cacaacacta cagagccaga tcctcactct    420
ctcagcccgg agcttcaagc actgatttct gaggtggctc aacacgatgt acagaatggg    480
cgggaatatg gagtggtgct ggcacctgat ggctccaccg tagctgtgaa gcctctgctg    540
tttgggctag aggccggtct acaggcacac agcgttgcta acttgccttc agattgtctg    600
gctatcccct gtgatactgg agacaccttg gccaatatta gagccacctg gccaggactc    660
atggatgctt ttccaaatgc ctcttctcca gatgttggag ccactttacc aaacgacaaa    720
gccaagactc ccaccactgt ggacagactc ctggcaatca ccttggctgg tgacttaggt    780
ctgaccttcc tccacaggtc ccagacttgg agtcctccag actgggaac tgagggctgc     840 tgggaccagc ttactgcccc cagggtcttc acactgttgg accccaggc atccaggctc     900 accatggctt tcctcaatgg tgccttagat ggagctctcc ttgggaacca cttgagccaa    960
atccctaggc ccacccacc cctcagccac ctgctaagag agtactatgg agctggggtg     1020
aatggagatc cggtgttccg aagtaacttc cgaaggcaga acggtgctgc tttgacttca    1080
gcccctaccc tggcccagca ggtatgggag gccttgtcc tgttacagaa actggagcca     1140
gaacacctac agttgcagaa cattagccaa gagcagctgg ctcaggtagc caccttggct    1200
accaaggagt tcactgaggc tttcctggga tgcccagcca ttcaccccg ctgccgttgg     1260 ggagcggctc cctaccgagg ccacccaaca ccactccggc tgccacttgg attcttatat    1320
gtgcatcaca catacgtgcc agcgccaccc tgcaccacct tccagagctg cgccgccgat    1380
atgcgctcca tgcagcgttt ccaccaggat gtgcgcaagt gggatgacat cggctacagt    1440
ttcgtggtag gctccgacgg ctatctgtac cagggccgtg gctggcactg gtaggtgcg     1500 cacacacgcg gctacaactc ccgcggcttc ggtgtggcct tcgtgggcaa ctacactggg    1560
tcactgccca acgaagctgc gctgaacacg gtgcgcgacg cgctcccgag ctgcgcaatt    1620
cgcgaaggtc tcttgcggcc agactacaag ctgcttggcc accgccagct agtgctcacc    1680
cactgccccg ggaacgcgct cttcaacttg ctgcgcacct ggcctcactt cacagaggtt    1740
gaaaactaag aactcctttg agagacccctt gaagatccag gaggtattat ccctgatgat    1800
cctttgagca accacagacc tccaataaag ggaccactga aggaaaaaa aaaaaaaaaa    1860 aaaaaaaaaa aaaaaa                                                    1876
```

<210> SEQ ID NO 4
<211> LENGTH: 530
<212> TYPE: PRT
<213> ORGANISM: human

<400> SEQUENCE: 4

```
Met Lys Ala Trp Gly Ala Leu Trp Ile Val Leu Gly Leu Leu Leu Trp
1               5                   10                  15

Pro Glu Pro Gly Ala Ala Ser Ser Leu Pro Leu Leu Met Asp Ser Ile
                20                  25                  30

Ile Gln Ala Leu Ala Glu Leu Glu Gln Lys Val Pro Val Thr Glu Ala
            35                  40                  45

Ser Ile Thr Ala Ser Ala Trp Ile Leu Ser Ala Lys Asn Ser Ser Thr
        50                  55                  60

His Asn Ser Leu His Gln Arg Leu Leu Leu Lys Ala Pro Ser His Asn
    65                  70                  75                  80

Thr Thr Glu Pro Asp Pro His Ser Leu Ser Pro Glu Leu Gln Ala Leu
                85                  90                  95

Ile Ser Glu Val Ala Gln His Asp Val Gln Asn Gly Arg Glu Tyr Gly
```

-continued

```
                100                 105                 110
Val Val Leu Ala Pro Asp Gly Ser Thr Val Ala Val Lys Pro Leu Leu
            115                 120                 125

Phe Gly Leu Glu Ala Gly Leu Gln Ala His Ser Val Ala Asn Leu Pro
        130                 135                 140

Ser Asp Cys Leu Ala Ile Pro Cys Asp Thr Gly Asp Thr Leu Ala Asn
145                 150                 155                 160

Ile Arg Ala Thr Trp Pro Gly Leu Met Asp Ala Phe Pro Asn Ala Ser
                165                 170                 175

Ser Pro Asp Val Gly Ala Thr Leu Pro Asn Asp Lys Ala Lys Thr Pro
            180                 185                 190

Thr Thr Val Asp Arg Leu Leu Ala Ile Thr Leu Ala Gly Asp Leu Gly
        195                 200                 205

Leu Thr Phe Leu His Arg Ser Gln Thr Trp Ser Pro Pro Gly Leu Gly
    210                 215                 220

Thr Glu Gly Cys Trp Asp Gln Leu Thr Ala Pro Arg Val Phe Thr Leu
225                 230                 235                 240

Leu Asp Pro Gln Ala Ser Arg Leu Thr Met Ala Phe Leu Asn Gly Ala
                245                 250                 255

Leu Asp Gly Ala Leu Leu Gly Asn His Leu Ser Gln Ile Pro Arg Pro
            260                 265                 270

His Pro Pro Leu Ser His Leu Leu Arg Glu Tyr Tyr Gly Ala Gly Val
        275                 280                 285

Asn Gly Asp Pro Val Phe Arg Ser Asn Phe Arg Arg Gln Asn Gly Ala
    290                 295                 300

Ala Leu Thr Ser Ala Pro Thr Leu Ala Gln Gln Val Trp Glu Ala Leu
305                 310                 315                 320

Val Leu Leu Gln Lys Leu Glu Pro Glu His Leu Gln Leu Gln Asn Ile
                325                 330                 335

Ser Gln Glu Gln Leu Ala Gln Val Ala Thr Leu Ala Thr Lys Glu Phe
            340                 345                 350

Thr Glu Ala Phe Leu Gly Cys Pro Ala Ile His Pro Arg Cys Arg Trp
        355                 360                 365

Gly Ala Ala Pro Tyr Arg Gly His Pro Thr Pro Leu Arg Leu Pro Leu
    370                 375                 380

Gly Phe Leu Tyr Val His His Thr Tyr Val Pro Ala Pro Pro Cys Thr
385                 390                 395                 400

Thr Phe Gln Ser Cys Ala Ala Asp Met Arg Ser Met Gln Arg Phe His
                405                 410                 415

Gln Asp Val Arg Lys Trp Asp Asp Ile Gly Tyr Ser Phe Val Val Gly
            420                 425                 430

Ser Asp Gly Tyr Leu Tyr Gln Gly Arg Gly Trp His Trp Val Gly Ala
        435                 440                 445

His Thr Arg Gly Tyr Asn Ser Arg Gly Phe Gly Val Ala Phe Val Gly
    450                 455                 460

Asn Tyr Thr Gly Ser Leu Pro Asn Glu Ala Ala Leu Asn Thr Val Arg
465                 470                 475                 480

Asp Ala Leu Pro Ser Cys Ala Ile Arg Glu Gly Leu Leu Arg Pro Asp
                485                 490                 495

Tyr Lys Leu Leu Gly His Arg Gln Leu Val Leu Thr His Cys Pro Gly
            500                 505                 510

Asn Ala Leu Phe Asn Leu Leu Arg Thr Trp Pro His Phe Thr Glu Val
        515                 520                 525
```

Glu Asn
    530

<210> SEQ ID NO 5
<211> LENGTH: 733
<212> TYPE: DNA
<213> ORGANISM: human

<400> SEQUENCE: 5

```
gggatccgga gcccaaatct tctgacaaaa ctcacacatg cccaccgtgc ccagcacctg      60
aattcgaggg tgcaccgtca gtcttcctct tccccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agcccctccca accccatcg    360
agaaaaccat ctccaaagcc aaagggcagc ccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733
```

<210> SEQ ID NO 6
<211> LENGTH: 5
<212> TYPE: PRT
<213> ORGANISM: human
<220> FEATURE:
<221> NAME/KEY: MISC_FEATURE
<222> LOCATION: (3)..(3)
<223> OTHER INFORMATION: Xaa equals any amino acid

<400> SEQUENCE: 6

Trp Ser Xaa Trp Ser
1               5

<210> SEQ ID NO 7
<211> LENGTH: 86
<212> TYPE: DNA
<213> ORGANISM: human

<400> SEQUENCE: 7

```
gcgcctcgag atttccccga atctagatt tccccgaaat gatttccccg aaatgatttc      60
cccgaaatat ctgccatctc aattag                                         86
```

<210> SEQ ID NO 8
<211> LENGTH: 27
<212> TYPE: DNA
<213> ORGANISM: human

<400> SEQUENCE: 8

```
gcggcaagct ttttgcaaag cctaggc                                        27
```

<210> SEQ ID NO 9
<211> LENGTH: 271
<212> TYPE: DNA

<213> ORGANISM: human

<400> SEQUENCE: 9

| | | | | | |
|---|---|---|---|---|---|
| ctcgagattt | ccccgaaatc | tagatttccc | cgaaatgatt | tccccgaaat | gatttccccg | 60 |
| aaatatctgc | catctcaatt | agtcagcaac | catagtcccg | ccctaactc | cgcccatccc | 120 |
| gcccctaact | ccgcccagtt | ccgcccattc | tccgcccat | ggctgactaa | ttttttttat | 180 |
| ttatgcagag | gccgaggccg | cctcggcctc | tgagctattc | cagaagtagt | gaggaggctt | 240 |
| ttttggaggc | ctaggctttt | gcaaaaagct | t | | | 271 |

<210> SEQ ID NO 10
<211> LENGTH: 32
<212> TYPE: DNA
<213> ORGANISM: human

<400> SEQUENCE: 10
gcgctcgagg gatgacagcg atagaacccc gg       32

<210> SEQ ID NO 11
<211> LENGTH: 31
<212> TYPE: DNA
<213> ORGANISM: human

<400> SEQUENCE: 11
gcgaagcttc gcgactcccc ggatccgcct c        31

<210> SEQ ID NO 12
<211> LENGTH: 12
<212> TYPE: DNA
<213> ORGANISM: human

<400> SEQUENCE: 12
ggggactttc cc                             12

<210> SEQ ID NO 13
<211> LENGTH: 73
<212> TYPE: DNA
<213> ORGANISM: human

<400> SEQUENCE: 13

| | | | | | |
|---|---|---|---|---|---|
| gcggcctcga | ggggactttc | ccggggactt | tccggggact | ttccgggact | ttccatcctg | 60 |
| ccatctcaat | tag | | | | | 73 |

<210> SEQ ID NO 14
<211> LENGTH: 256
<212> TYPE: DNA
<213> ORGANISM: human

<400> SEQUENCE: 14

| | | | | | |
|---|---|---|---|---|---|
| ctcgagggga | ctttcccggg | gactttccgg | ggactttccg | ggactttcca | tctgccatct | 60 |
| caattagtca | gcaaccatag | tcccgcccct | aactccgccc | atcccgcccc | taactccgcc | 120 |
| cagttccgcc | cattctccgc | cccatggctg | actaattttt | tttatttatg | cagaggccga | 180 |
| ggccgcctcg | gcctctgagc | tattccagaa | gtagtgagga | ggcttttttg | gaggcctagg | 240 |
| cttttgcaaa | aagctt | | | | | 256 |

<210> SEQ ID NO 15
<211> LENGTH: 30
<212> TYPE: DNA
<213> ORGANISM: human

```
<400> SEQUENCE: 15
gcagcacata tgcgcggctg gcactgggtg                                           30

<210> SEQ ID NO 16
<211> LENGTH: 28
<212> TYPE: DNA
<213> ORGANISM: human

<400> SEQUENCE: 16
cagcaggtac cttaggagct ggggaaag                                             28

<210> SEQ ID NO 17
<211> LENGTH: 43
<212> TYPE: DNA
<213> ORGANISM: human

<400> SEQUENCE: 17
gcagcaagga tccgccatcc gcggctggca ctgggtgggc gcc                            43

<210> SEQ ID NO 18
<211> LENGTH: 39
<212> TYPE: DNA
<213> ORGANISM: human

<400> SEQUENCE: 18
gcagcaggta ccttaggagc tggggaaagg acaggctgg                                 39
```